US012325733B2

(12) United States Patent
Bulek et al.

(10) Patent No.: US 12,325,733 B2
(45) Date of Patent: Jun. 10, 2025

(54) BINDING DOMAIN

(71) Applicant: AUTOLUS LIMITED, London (GB)

(72) Inventors: Anna Bulek, London (GB); Martin Pulé, London (GB); Shaun Cordoba, London (GB); Simon Thomas, London (GB); Shimobi Onuoha, London (GB); Mathieu Ferrari, London (GB); Vania Baldan, London (GB)

(73) Assignee: AUTOLUS LIMITED, London (GB)

( * ) Notice: Subject to any disclaimer, the term of this patent is extended or adjusted under 35 U.S.C. 154(b) by 1045 days.

(21) Appl. No.: 17/290,188

(22) PCT Filed: Oct. 31, 2019

(86) PCT No.: PCT/GB2019/053100

§ 371 (c)(1),
(2) Date: Apr. 29, 2021

(87) PCT Pub. No.: WO2020/089644

PCT Pub. Date: May 7, 2020

(65) Prior Publication Data

US 2022/0041718 A1 Feb. 10, 2022

(30) Foreign Application Priority Data

Oct. 31, 2018 (GB) ...................................... 1817822

(51) Int. Cl.

| | |
|---|---|
| ***A61P 35/00*** | (2006.01) |
| ***A61K 47/68*** | (2017.01) |
| ***C07K 14/705*** | (2006.01) |
| ***C07K 14/725*** | (2006.01) |
| ***C07K 16/28*** | (2006.01) |
| ***G01N 33/574*** | (2006.01) |

(52) U.S. Cl.

CPC ...... *C07K 14/7051* (2013.01); *A61K 47/6849* (2017.08); *C07K 14/70517* (2013.01); *C07K 16/2809* (2013.01); *G01N 33/57407* (2013.01); *G01N 33/57426* (2013.01); *C07K 2317/56* (2013.01); *C07K 2319/03* (2013.01)

(58) Field of Classification Search

None

See application file for complete search history.

(56) References Cited

U.S. PATENT DOCUMENTS

| | | | |
|---|---|---|---|
| 7,052,906 | B1 | 5/2006 | Lawson et al. |
| 2017/0066827 | A1 | 3/2017 | Pule et al. |
| 2017/0334998 | A1 | 11/2017 | Pule et al. |
| 2019/0209612 | A1 | 7/2019 | Pule et al. |
| 2020/0140549 | A1 | 5/2020 | Cordoba et al. |
| 2020/0200756 | A1 | 6/2020 | Pule et al. |

FOREIGN PATENT DOCUMENTS

| | | | |
|---|---|---|---|
| JP | 2006315964 | A | 11/2006 |
| RU | 2014120629 | A | 12/2015 |
| WO | WO-2015/132598 | A1 | 9/2015 |
| WO | WO-2016/151315 | A1 | 9/2016 |
| WO | WO-2018/224844 | A1 | 12/2018 |
| WO | WO-2020/025928 | A1 | 2/2020 |
| WO | WO-2020/084290 | A1 | 4/2020 |

OTHER PUBLICATIONS

Vajdos et al. (J Mol Biol. Jul. 5, 2002;320(2):415-28). (Year: 2002).*
Bedouelle et al. (FEBS J. Jan. 2006;273(1):34-46). (Year: 2006).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Chothia et al., "Canonical Structures for the Hypervariable Regions of Immunoglobulins," J Mol Biol 196:901-17 (1987).
International Search Report and Written Opinion from International Application No. PCT/GB2019/053100 dated Feb. 4, 2020.
Kabat et al., Sequences of Proteins of Immunological Interest, 5th Ed., NIH Publication No. 91-3242, Bethesda, MD (1991).
Maciocia et al., "Targeting the T cell receptor B-chain constant region for immunotherapy of T cell malignancies," Nature Medicine, 23(12):1416-1423 (2017).
Onuoha et al., "Structure Guided Engineering of Highly Specific Chimeric Antigen Receptors for the Treatment of T Cell Lymphomas," Blood, 132(Suppl 1):1661-1661 (2018).
Viney et al., "Generation of Monoclonal Antibodies Against a Human T Cell Receptor B Chain Expressed in Transgenic Mice," Hybridome, 11(6):701-713 (1992).
Baylot et al., "Chapter 13 TCTP Has a Crucial Role in the Different Stages of Prostate Cancer Malignant Progression", Results and Problems in Cell Differentiation, 64:255-261 (2017).
Colman, "Effects of Amino Acid Sequence Changes on Antibody-Antigen Interactions," Biomolecular Research Institute, 145(1):33-36 (1994).
Roitt et al., "Immunology", Moscow, Mir, pp. 110-111 (2000).
Rudikoff et al., "Single Amino Acid Substitution Altering Antigen-Binding Specificity", Immunology, Proceedings of the National Academy of Sciences, 79:1979-1983 (1982).
Singer et al., "Genes and Genomes", Moscow, Mir, 1:63-64 (1998).

* cited by examiner

*Primary Examiner* — Zachary S Skelding
(74) *Attorney, Agent, or Firm* — MARSHALL, GERSTEIN & BORUN LLP

(57) ABSTRACT

The present invention provides a variant antigen-binding domain which comprises at least one mutation in the VH domain compared to a reference antibody and which displays an increased affinity for TRBC2 over the reference antibody. It further provides an antibody, a chimeric antigen receptor (CAR), and a bispecific T-cell engager (BiTE), a cell which comprises said CAR, and a conjugate comprising said variant antigen-binding domain or said antibody. Additionally, it provides medical uses, diagnostic methods and methods of personalised medicine that exploit the products of the invention.

15 Claims, 11 Drawing Sheets

Specification includes a Sequence Listing.

B) scFv - FC (2x)

SEQUENCE LISTING

<160> NUMBER OF SEQ ID NOS: 36

<210> SEQ ID NO 1
<211> LENGTH: 124
<212> TYPE: PRT
<213> ORGANISM: Artificial Sequence
<220> FEATURE:
<223> OTHER INFORMATION: VH (heavy chain) domain of hJOVI-1, a humanised JOVI-1 antibody

<400> SEQUENCE: 1

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Val Met His Trp Val Arg Gln Ala Pro Gly Gln Gly Leu Glu Trp Met
35 40 45

Gly Phe Ile Asn Pro Tyr Asn Asp Asp Ile Gln Ser Asn Glu Arg Phe
50 55 60

Arg Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Ala Gly Tyr Asn Phe Asp Gly Ala Tyr Arg Phe Phe Asp
100 105 110

Phe Trp Gly Gln Gly Thr Met Val Thr Val Ser Ser
115 120

<210> SEQ ID NO 2
<211> LENGTH: 112
<212> TYPE: PRT
<213> ORGANISM: Artificial Sequence
<220> FEATURE:
<223> OTHER INFORMATION: VL (light chain) domain of hJOVI-1, a humanised JOVI-1 antibody

<400> SEQUENCE: 2

Asp Ile Val Met Thr Gln Ser Pro Leu Ser Leu Pro Val Thr Pro Gly
1 5 10 15

Glu Pro Ala Ser Ile Ser Cys Arg Ser Ser Gln Arg Leu Val His Ser
20 25 30

Asn Gly Asn Thr Tyr Leu His Trp Tyr Leu Gln Lys Pro Gly Gln Ser
35 40 45

Pro Arg Leu Leu Ile Tyr Arg Val Ser Asn Arg Phe Pro Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser

```
            85                  90                  95

Thr His Val Pro Tyr Thr Phe Gly Gln Gly Thr Lys Leu Glu Ile Lys
            100                 105                 110


<210> SEQ ID NO 3
<211> LENGTH: 21
<212> TYPE: PRT
<213> ORGANISM: Artificial Sequence
<220> FEATURE:
<223> OTHER INFORMATION: signal peptide

<400> SEQUENCE: 3

Met Gly Thr Ser Leu Leu Cys Trp Met Ala Leu Cys Leu Leu Gly Ala
1               5                   10                  15

Asp His Ala Asp Gly
            20


<210> SEQ ID NO 4
<211> LENGTH: 21
<212> TYPE: PRT
<213> ORGANISM: Artificial Sequence
<220> FEATURE:
<223> OTHER INFORMATION: signal peptide derived from IgG1

<400> SEQUENCE: 4

Met Ser Leu Pro Val Thr Ala Leu Leu Leu Pro Leu Ala Leu Leu Leu
1               5                   10                  15

His Ala Ala Arg Pro
            20


<210> SEQ ID NO 5
<211> LENGTH: 20
<212> TYPE: PRT
<213> ORGANISM: Artificial Sequence
<220> FEATURE:
<223> OTHER INFORMATION: signal peptide derived from CD8

<400> SEQUENCE: 5

Met Ala Val Pro Thr Gln Val Leu Gly Leu Leu Leu Leu Trp Leu Thr
1               5                   10                  15

Asp Ala Arg Cys
            20


<210> SEQ ID NO 6
<211> LENGTH: 234
<212> TYPE: PRT
<213> ORGANISM: Artificial Sequence
<220> FEATURE:
<223> OTHER INFORMATION: spacer sequence, hinge-CH2CH3 of human IgG1

<400> SEQUENCE: 6

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
```

-continued

```
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230


<210> SEQ ID NO 7
<211> LENGTH: 46
<212> TYPE: PRT
<213> ORGANISM: Artificial Sequence
<220> FEATURE:
<223> OTHER INFORMATION: spacer sequence, human CD8 stalk

<400> SEQUENCE: 7

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45


<210> SEQ ID NO 8
<211> LENGTH: 20
<212> TYPE: PRT
<213> ORGANISM: Artificial Sequence
<220> FEATURE:
<223> OTHER INFORMATION: spacer sequence, human IgG1 hinge

<400> SEQUENCE: 8

Ala Glu Pro Lys Ser Pro Asp Lys Thr His Thr Cys Pro Pro Cys Pro
1               5                   10                  15

Lys Asp Pro Lys
            20


<210> SEQ ID NO 9
<211> LENGTH: 185
<212> TYPE: PRT
<213> ORGANISM: Artificial Sequence
<220> FEATURE:
<223> OTHER INFORMATION: spacer sequence, CD2 ectodomain

<400> SEQUENCE: 9

Lys Glu Ile Thr Asn Ala Leu Glu Thr Trp Gly Ala Leu Gly Gln Asp
1               5                   10                  15

Ile Asn Leu Asp Ile Pro Ser Phe Gln Met Ser Asp Asp Ile Asp Asp
            20                  25                  30
```

-continued

Ile Lys Trp Glu Lys Thr Ser Asp Lys Lys Lys Ile Ala Gln Phe Arg
35 40 45

Lys Glu Lys Glu Thr Phe Lys Glu Lys Asp Thr Tyr Lys Leu Phe Lys
50 55 60

Asn Gly Thr Leu Lys Ile Lys His Leu Lys Thr Asp Asp Gln Asp Ile
65 70 75 80

Tyr Lys Val Ser Ile Tyr Asp Thr Lys Gly Lys Asn Val Leu Glu Lys
85 90 95

Ile Phe Asp Leu Lys Ile Gln Glu Arg Val Ser Lys Pro Lys Ile Ser
100 105 110

Trp Thr Cys Ile Asn Thr Thr Leu Thr Cys Glu Val Met Asn Gly Thr
115 120 125

Asp Pro Glu Leu Asn Leu Tyr Gln Asp Gly Lys His Leu Lys Leu Ser
130 135 140

Gln Arg Val Ile Thr His Lys Trp Thr Thr Ser Leu Ser Ala Lys Phe
145 150 155 160

Lys Cys Thr Ala Gly Asn Lys Val Ser Lys Glu Ser Ser Val Glu Pro
165 170 175

Val Ser Cys Pro Glu Lys Gly Leu Asp
180 185

<210> SEQ ID NO 10
<211> LENGTH: 259
<212> TYPE: PRT
<213> ORGANISM: Artificial Sequence
<220> FEATURE:
<223> OTHER INFORMATION: spacer sequence, CD34 ectodomain

<400> SEQUENCE: 10

Ser Leu Asp Asn Asn Gly Thr Ala Thr Pro Glu Leu Pro Thr Gln Gly
1 5 10 15

Thr Phe Ser Asn Val Ser Thr Asn Val Ser Tyr Gln Glu Thr Thr Thr
20 25 30

Pro Ser Thr Leu Gly Ser Thr Ser Leu His Pro Val Ser Gln His Gly
35 40 45

Asn Glu Ala Thr Thr Asn Ile Thr Glu Thr Thr Val Lys Phe Thr Ser
50 55 60

Thr Ser Val Ile Thr Ser Val Tyr Gly Asn Thr Asn Ser Ser Val Gln
65 70 75 80

Ser Gln Thr Ser Val Ile Ser Thr Val Phe Thr Thr Pro Ala Asn Val
85 90 95

Ser Thr Pro Glu Thr Thr Leu Lys Pro Ser Leu Ser Pro Gly Asn Val
100 105 110

Ser Asp Leu Ser Thr Thr Ser Thr Ser Leu Ala Thr Ser Pro Thr Lys
115 120 125

Pro Tyr Thr Ser Ser Ser Pro Ile Leu Ser Asp Ile Lys Ala Glu Ile
130 135 140

Lys Cys Ser Gly Ile Arg Glu Val Lys Leu Thr Gln Gly Ile Cys Leu
145 150 155 160

Glu Gln Asn Lys Thr Ser Ser Cys Ala Glu Phe Lys Lys Asp Arg Gly
165 170 175

Glu Gly Leu Ala Arg Val Leu Cys Gly Glu Glu Gln Ala Asp Ala Asp
180 185 190

Ala Gly Ala Gln Val Cys Ser Leu Leu Leu Ala Gln Ser Glu Val Arg
195 200 205

-continued

Pro Gln Cys Leu Leu Leu Val Leu Ala Asn Arg Thr Glu Ile Ser Ser
    210                 215                 220

Lys Leu Gln Leu Met Lys Lys His Gln Ser Asp Leu Lys Lys Leu Gly
225                 230                 235                 240

Ile Leu Asp Phe Thr Glu Gln Asp Val Ala Ser His Gln Ser Tyr Ser
                245                 250                 255

Gln Lys Thr

<210> SEQ ID NO 11
<211> LENGTH: 21
<212> TYPE: PRT
<213> ORGANISM: Artificial Sequence
<220> FEATURE:
<223> OTHER INFORMATION: CD8a transmembrane domain

<400> SEQUENCE: 11

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 12
<211> LENGTH: 24
<212> TYPE: PRT
<213> ORGANISM: Artificial Sequence
<220> FEATURE:
<223> OTHER INFORMATION: TYRP-1 transmembrane domain

<400> SEQUENCE: 12

Ile Ile Ala Ile Ala Val Val Gly Ala Leu Leu Leu Val Ala Leu Ile
1               5                   10                  15

Phe Gly Thr Ala Ser Tyr Leu Ile
            20

<210> SEQ ID NO 13
<211> LENGTH: 140
<212> TYPE: PRT
<213> ORGANISM: Artificial Sequence
<220> FEATURE:
<223> OTHER INFORMATION: sequence comprising CD28 transmembrane domain
      and CD3zeta endodomain

<400> SEQUENCE: 13

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Arg Val Lys Phe
            20                  25                  30

Ser Arg Ser Ala Asp Ala Pro Ala Tyr Gln Gln Gly Gln Asn Gln Leu
        35                  40                  45

Tyr Asn Glu Leu Asn Leu Gly Arg Arg Glu Glu Tyr Asp Val Leu Asp
    50                  55                  60

Lys Arg Arg Gly Arg Asp Pro Glu Met Gly Gly Lys Pro Arg Arg Lys
65                  70                  75                  80

Asn Pro Gln Glu Gly Leu Tyr Asn Glu Leu Gln Lys Asp Lys Met Ala
                85                  90                  95

Glu Ala Tyr Ser Glu Ile Gly Met Lys Gly Glu Arg Arg Arg Gly Lys
            100                 105                 110

Gly His Asp Gly Leu Tyr Gln Gly Leu Ser Thr Ala Thr Lys Asp Thr
        115                 120                 125

```
Tyr Asp Ala Leu His Met Gln Ala Leu Pro Pro Arg
    130                 135                 140


<210> SEQ ID NO 14
<211> LENGTH: 180
<212> TYPE: PRT
<213> ORGANISM: Artificial Sequence
<220> FEATURE:
<223> OTHER INFORMATION: sequence comprising CD28 transmembrane domain
      and CD28 and CD3zeta endodomains

<400> SEQUENCE: 14

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser Arg Val Lys Phe Ser Arg Ser Ala Asp Ala Pro Ala
65                  70                  75                  80

Tyr Gln Gln Gly Gln Asn Gln Leu Tyr Asn Glu Leu Asn Leu Gly Arg
                85                  90                  95

Arg Glu Glu Tyr Asp Val Leu Asp Lys Arg Arg Gly Arg Asp Pro Glu
            100                 105                 110

Met Gly Gly Lys Pro Arg Arg Lys Asn Pro Gln Glu Gly Leu Tyr Asn
        115                 120                 125

Glu Leu Gln Lys Asp Lys Met Ala Glu Ala Tyr Ser Glu Ile Gly Met
    130                 135                 140

Lys Gly Glu Arg Arg Arg Gly Lys Gly His Asp Gly Leu Tyr Gln Gly
145                 150                 155                 160

Leu Ser Thr Ala Thr Lys Asp Thr Tyr Asp Ala Leu His Met Gln Ala
                165                 170                 175

Leu Pro Pro Arg
            180


<210> SEQ ID NO 15
<211> LENGTH: 216
<212> TYPE: PRT
<213> ORGANISM: Artificial Sequence
<220> FEATURE:
<223> OTHER INFORMATION: sequence comprising CD28 transmembrane domain
      and CD28, OX40 and CD3zeta endodomains

<400> SEQUENCE: 15

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser Arg Asp Gln Arg Leu Pro Pro Asp Ala His Lys Pro
65                  70                  75                  80

Pro Gly Gly Gly Ser Phe Arg Thr Pro Ile Gln Glu Glu Gln Ala Asp
                85                  90                  95
```

-continued

```
Ala His Ser Thr Leu Ala Lys Ile Arg Val Lys Phe Ser Arg Ser Ala
            100                 105                 110

Asp Ala Pro Ala Tyr Gln Gln Gly Gln Asn Gln Leu Tyr Asn Glu Leu
        115                 120                 125

Asn Leu Gly Arg Arg Glu Glu Tyr Asp Val Leu Asp Lys Arg Arg Gly
    130                 135                 140

Arg Asp Pro Glu Met Gly Gly Lys Pro Arg Arg Lys Asn Pro Gln Glu
145                 150                 155                 160

Gly Leu Tyr Asn Glu Leu Gln Lys Asp Lys Met Ala Glu Ala Tyr Ser
                165                 170                 175

Glu Ile Gly Met Lys Gly Glu Arg Arg Arg Gly Lys Gly His Asp Gly
            180                 185                 190

Leu Tyr Gln Gly Leu Ser Thr Ala Thr Lys Asp Thr Tyr Asp Ala Leu
        195                 200                 205

His Met Gln Ala Leu Pro Pro Arg
    210                 215


<210> SEQ ID NO 16
<211> LENGTH: 136
<212> TYPE: PRT
<213> ORGANISM: Artificial Sequence
<220> FEATURE:
<223> OTHER INFORMATION: sequence comprising CD8a transmembrane domain
      and CD3zeta endodomain

<400> SEQUENCE: 16

Ile Tyr Ile Trp Ala Pro Leu Ala Gly Thr Cys Gly Val Leu Leu Leu
1               5                   10                  15

Ser Leu Val Ile Thr Arg Val Leu Tyr Cys Lys Phe Ser Arg Ser Ala
            20                  25                  30

Asp Ala Pro Ala Tyr Gln Gln Gly Gln Asn Gln Leu Tyr Asn Glu Leu
        35                  40                  45

Asn Leu Gly Arg Arg Glu Glu Tyr Asp Val Leu Asp Lys Arg Arg Gly
    50                  55                  60

Arg Asp Pro Glu Met Gly Gly Lys Pro Arg Arg Lys Asn Pro Gln Glu
65                  70                  75                  80

Gly Leu Tyr Asn Glu Leu Gln Lys Asp Lys Met Ala Glu Ala Tyr Ser
                85                  90                  95

Glu Ile Gly Met Lys Gly Glu Arg Arg Arg Gly Lys Gly His Asp Gly
            100                 105                 110

Leu Tyr Gln Gly Leu Ser Thr Ala Thr Lys Asp Thr Tyr Asp Ala Leu
        115                 120                 125

His Met Gln Ala Leu Pro Pro Arg
    130                 135


<210> SEQ ID NO 17
<211> LENGTH: 178
<212> TYPE: PRT
<213> ORGANISM: Artificial Sequence
<220> FEATURE:
<223> OTHER INFORMATION: sequence comprising CD8a transmembrane domain
      and 4-1BB and CD3zeta endodomain

<400> SEQUENCE: 17

Ile Tyr Ile Trp Ala Pro Leu Ala Gly Thr Cys Gly Val Leu Leu Leu
1               5                   10                  15

Ser Leu Val Ile Thr Leu Tyr Cys Lys Arg Gly Arg Lys Lys Leu Leu
            20                  25                  30
```

-continued

```
Tyr Ile Phe Lys Gln Pro Phe Met Arg Pro Val Gln Thr Thr Gln Glu
        35                  40                  45

Glu Asp Gly Cys Ser Cys Arg Phe Pro Glu Glu Glu Glu Gly Gly Cys
    50                  55                  60

Glu Leu Arg Val Lys Phe Ser Arg Ser Ala Asp Ala Pro Ala Tyr Gln
65                  70                  75                  80

Gln Gly Gln Asn Gln Leu Tyr Asn Glu Leu Asn Leu Gly Arg Arg Glu
                85                  90                  95

Glu Tyr Asp Val Leu Asp Lys Arg Arg Gly Arg Asp Pro Glu Met Gly
            100                 105                 110

Gly Lys Pro Arg Arg Lys Asn Pro Gln Glu Gly Leu Tyr Asn Glu Leu
        115                 120                 125

Gln Lys Asp Lys Met Ala Glu Ala Tyr Ser Glu Ile Gly Met Lys Gly
    130                 135                 140

Glu Arg Arg Arg Gly Lys Gly His Asp Gly Leu Tyr Gln Gly Leu Ser
145                 150                 155                 160

Thr Ala Thr Lys Asp Thr Tyr Asp Ala Leu His Met Gln Ala Leu Pro
                165                 170                 175

Pro Arg


<210> SEQ ID NO 18
<211> LENGTH: 178
<212> TYPE: PRT
<213> ORGANISM: Artificial Sequence
<220> FEATURE:
<223> OTHER INFORMATION: sequence comprising TYRP-1 transmembrane domain
      and 4-1BB and CD3zeta endodomains

<400> SEQUENCE: 18

Ile Ile Ala Ile Ala Val Val Gly Ala Leu Leu Leu Val Ala Leu Ile
1               5                   10                  15

Phe Gly Thr Ala Ser Tyr Leu Ile Lys Arg Gly Arg Lys Lys Leu Leu
            20                  25                  30

Tyr Ile Phe Lys Gln Pro Phe Met Arg Pro Val Gln Thr Thr Gln Glu
        35                  40                  45

Glu Asp Gly Cys Ser Cys Arg Phe Pro Glu Glu Glu Glu Gly Gly Cys
    50                  55                  60

Glu Leu Arg Val Lys Phe Ser Arg Ser Ala Asp Ala Pro Ala Tyr Gln
65                  70                  75                  80

Gln Gly Gln Asn Gln Leu Tyr Asn Glu Leu Asn Leu Gly Arg Arg Glu
                85                  90                  95

Glu Tyr Asp Val Leu Asp Lys Arg Arg Gly Arg Asp Pro Glu Met Gly
            100                 105                 110

Gly Lys Pro Arg Arg Lys Asn Pro Gln Glu Gly Leu Tyr Asn Glu Leu
        115                 120                 125

Gln Lys Asp Lys Met Ala Glu Ala Tyr Ser Glu Ile Gly Met Lys Gly
    130                 135                 140

Glu Arg Arg Arg Gly Lys Gly His Asp Gly Leu Tyr Gln Gly Leu Ser
145                 150                 155                 160

Thr Ala Thr Lys Asp Thr Tyr Asp Ala Leu His Met Gln Ala Leu Pro
                165                 170                 175

Pro Arg


<210> SEQ ID NO 19
<211> LENGTH: 45
<212> TYPE: PRT
```

-continued

<213> ORGANISM: Artificial Sequence
<220> FEATURE:
<223> OTHER INFORMATION: spacer sequence, COMP

<400> SEQUENCE: 19

Asp Leu Gly Pro Gln Met Leu Arg Glu Leu Gln Glu Thr Asn Ala Ala
1 5 10 15

Leu Gln Asp Val Arg Glu Leu Leu Arg Gln Gln Val Arg Glu Ile Thr
20 25 30

Phe Leu Lys Asn Thr Val Met Glu Cys Asp Ala Cys Gly
35 40 45

<210> SEQ ID NO 20
<211> LENGTH: 5
<212> TYPE: PRT
<213> ORGANISM: Artificial Sequence
<220> FEATURE:
<223> OTHER INFORMATION: truncated COMP, 5 C-terminal amino acids

<400> SEQUENCE: 20

Cys Asp Ala Cys Gly
1 5

<210> SEQ ID NO 21
<211> LENGTH: 20
<212> TYPE: PRT
<213> ORGANISM: Artificial Sequence
<220> FEATURE:
<223> OTHER INFORMATION: truncated COMP, C terminus 20 amino acids

<400> SEQUENCE: 21

Gln Gln Val Arg Glu Ile Thr Phe Leu Lys Asn Thr Val Met Glu Cys
1 5 10 15

Asp Ala Cys Gly
20

<210> SEQ ID NO 22
<211> LENGTH: 252
<212> TYPE: PRT
<213> ORGANISM: Artificial Sequence
<220> FEATURE:
<223> OTHER INFORMATION: single-chain variable fragment, scFv

<400> SEQUENCE: 22

Gln Val Gln Leu Val Gln Ser Gly Ala Glu Val Lys Lys Pro Gly Ala
1 5 10 15

Ser Val Lys Val Ser Cys Lys Ala Ser Gly Tyr Lys Phe Thr Gly Phe
20 25 30

Val Met His Trp Val Arg Gln Ala Pro Gly Gln Gly Leu Glu Trp Met
35 40 45

Gly Phe Ile Asn Pro Tyr Asn Asp Asp Ile Gln Ser Asn Glu Arg Phe
50 55 60

Arg Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Asn Gly Leu Met Phe Asp Gly Ala Tyr Arg Phe Phe Asp
100 105 110

Phe Trp Gly Gln Gly Thr Met Val Thr Val Ser Ser Gly Gly Gly Gly
115 120 125

Ser Gly Gly Gly Gly Ser Gly Gly Gly Gly Ser Asp Ile Val Met Thr

-continued

```
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Arg Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg
                245                 250


<210> SEQ ID NO 23
<211> LENGTH: 486
<212> TYPE: PRT
<213> ORGANISM: Artificial Sequence
<220> FEATURE:
<223> OTHER INFORMATION: scFv-Fc

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Leu Met Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Arg Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Arg
```

```
                245                 250                 255

Gly Pro Thr Ile Lys Pro Cys Pro Pro Cys Lys Cys Pro Ala Pro Asn
            260                 265                 270

Leu Leu Gly Gly Pro Ser Val Phe Ile Phe Pro Pro Lys Ile Lys Asp
        275                 280                 285

Val Leu Met Ile Ser Leu Ser Pro Ile Val Thr Cys Val Val Val Asp
    290                 295                 300

Val Ser Glu Asp Asp Pro Asp Val Gln Ile Ser Trp Phe Val Asn Asn
305                 310                 315                 320

Val Glu Val His Thr Ala Gln Thr Gln Thr His Arg Glu Asp Tyr Asn
                325                 330                 335

Ser Thr Leu Arg Val Val Ser Ala Leu Pro Ile Gln His Gln Asp Trp
            340                 345                 350

Met Ser Gly Lys Glu Phe Lys Cys Lys Val Asn Asn Lys Asp Leu Pro
        355                 360                 365

Ala Pro Ile Glu Arg Thr Ile Ser Lys Pro Lys Gly Ser Val Arg Ala
    370                 375                 380

Pro Gln Val Tyr Val Leu Pro Pro Pro Glu Glu Glu Met Thr Lys Lys
385                 390                 395                 400

Gln Val Thr Leu Thr Cys Met Val Thr Asp Phe Met Pro Glu Asp Ile
                405                 410                 415

Tyr Val Glu Trp Thr Asn Asn Gly Lys Thr Glu Leu Asn Tyr Lys Asn
            420                 425                 430

Thr Glu Pro Val Leu Asp Ser Asp Gly Ser Tyr Phe Met Tyr Ser Lys
        435                 440                 445

Leu Arg Val Glu Lys Lys Asn Trp Val Glu Arg Asn Ser Tyr Ser Cys
    450                 455                 460

Ser Val Val His Glu Gly Leu His Asn His His Thr Thr Lys Ser Phe
465                 470                 475                 480

Ser Arg Thr Pro Gly Lys
                485


<210> SEQ ID NO 24
<211> LENGTH: 338
<212> TYPE: PRT
<213> ORGANISM: Artificial Sequence
<220> FEATURE:
<223> OTHER INFORMATION: scFv-COMP

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Leu Met Phe Asp Gly Ala Tyr Arg Phe Phe Asp
            100                 105                 110

Phe Trp Gly Gln Gly Thr Met Val Thr Val Ser Ser Gly Gly Gly Gly
```

```
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Arg Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Gly Gly Gly
                245                 250                 255

Gly Ser Gly Gly Gly Gly Ser Gly Gly Gly Gly Ser Ala Gly Ser Asp
            260                 265                 270

Leu Gly Pro Gln Met Leu Arg Glu Leu Gln Glu Thr Asn Ala Ala Leu
        275                 280                 285

Gln Asp Val Arg Glu Leu Leu Arg Gln Gln Val Arg Glu Ile Thr Phe
    290                 295                 300

Leu Lys Asn Thr Val Met Glu Cys Asp Ala Cys Gly Ser Gly Lys Lys
305                 310                 315                 320

Asp Pro Lys Ser Gly Gly Gly Gly Ser Tyr Pro Tyr Asp Val Pro Asp
                325                 330                 335

Tyr Ala


<210> SEQ ID NO 25
<211> LENGTH: 454
<212> TYPE: PRT
<213> ORGANISM: Artificial Sequence
<220> FEATURE:
<223> OTHER INFORMATION: CAR comprising T28K, Y32F, A100N mutations in
      the VH domain, N35K mutation in the VL domain, IgG1 hinge spacer,
      TYRP-1 transmembrane domain, and 4-1BB and CD3zeta endodomains

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Asn Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125
```

-continued

```
Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Lys Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Ala
                245                 250                 255

Glu Pro Lys Ser Pro Asp Lys Thr His Thr Cys Pro Pro Cys Pro Lys
            260                 265                 270

Asp Pro Lys Ile Ile Ala Ile Ala Val Val Gly Ala Leu Leu Leu Val
        275                 280                 285

Ala Leu Ile Phe Gly Thr Ala Ser Tyr Leu Ile Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450
```

<210> SEQ ID NO 26
<211> LENGTH: 454
<212> TYPE: PRT
<213> ORGANISM: Artificial Sequence
<220> FEATURE:
<223> OTHER INFORMATION: CAR comprising T28K, Y32F, A100N mutations in the VH domain, IgG1 hinge spacer, TYRP-1 transmembrane domain, and 4-1BB and CD3zeta endodomains

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
```

-continued

```
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Asn Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Asn Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Ala
                245                 250                 255

Glu Pro Lys Ser Pro Asp Lys Thr His Thr Cys Pro Pro Cys Pro Lys
            260                 265                 270

Asp Pro Lys Ile Ile Ala Ile Ala Val Val Gly Ala Leu Leu Leu Val
        275                 280                 285

Ala Leu Ile Phe Gly Thr Ala Ser Tyr Leu Ile Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445
```

-continued

Gln Ala Leu Pro Pro Arg
    450

<210> SEQ ID NO 27
<211> LENGTH: 454
<212> TYPE: PRT
<213> ORGANISM: Artificial Sequence
<220> FEATURE:
<223> OTHER INFORMATION: CAR comprising T28K, Y32F, A100N, N103L
      mutations in the VH domain, IgG1 hinge spacer, TYRP-1
      transmembrane domain, and 4-1BB and CD3zeta endodomains

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Leu Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Asn Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Ala
                245                 250                 255

Glu Pro Lys Ser Pro Asp Lys Thr His Thr Cys Pro Pro Cys Pro Lys
            260                 265                 270

Asp Pro Lys Ile Ile Ala Ile Ala Val Val Gly Ala Leu Leu Leu Val
        275                 280                 285

Ala Leu Ile Phe Gly Thr Ala Ser Tyr Leu Ile Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335
```

-continued

```
Gly Gly Cys Glu Leu Arg Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450


<210> SEQ ID NO 28
<211> LENGTH: 454
<212> TYPE: PRT
<213> ORGANISM: Artificial Sequence
<220> FEATURE:
<223> OTHER INFORMATION: CAR comprising T28K, Y32F, A100N, N103M
      mutations in the VH domain, N35Y mutation in the VL domain, IgG1
      hinge spacer, TYRP-1 transmembrane domain, and 4-1BB and CD3zeta
      endodomains

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Met Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Tyr Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220
```

-continued

Glu Asp Val Gly Val Tyr Tyr Cys Ser Gln Ser Thr His Val Pro Tyr
225 230 235 240

Thr Phe Gly Gln Gly Thr Lys Leu Glu Ile Lys Arg Ser Asp Pro Ala
245 250 255

Glu Pro Lys Ser Pro Asp Lys Thr His Thr Cys Pro Pro Cys Pro Lys
260 265 270

Asp Pro Lys Ile Ile Ala Ile Ala Val Val Gly Ala Leu Leu Leu Val
275 280 285

Ala Leu Ile Phe Gly Thr Ala Ser Tyr Leu Ile Lys Arg Gly Arg Lys
290 295 300

Lys Leu Leu Tyr Ile Phe Lys Gln Pro Phe Met Arg Pro Val Gln Thr
305 310 315 320

Thr Gln Glu Glu Asp Gly Cys Ser Cys Arg Phe Pro Glu Glu Glu Glu
325 330 335

Gly Gly Cys Glu Leu Arg Arg Val Lys Phe Ser Arg Ser Ala Asp Ala
340 345 350

Pro Ala Tyr Gln Gln Gly Gln Asn Gln Leu Tyr Asn Glu Leu Asn Leu
355 360 365

Gly Arg Arg Glu Glu Tyr Asp Val Leu Asp Lys Arg Arg Gly Arg Asp
370 375 380

Pro Glu Met Gly Gly Lys Pro Arg Arg Lys Asn Pro Gln Glu Gly Leu
385 390 395 400

Tyr Asn Glu Leu Gln Lys Asp Lys Met Ala Glu Ala Tyr Ser Glu Ile
405 410 415

Gly Met Lys Gly Glu Arg Arg Arg Gly Lys Gly His Asp Gly Leu Tyr
420 425 430

Gln Gly Leu Ser Thr Ala Thr Lys Asp Thr Tyr Asp Ala Leu His Met
435 440 445

Gln Ala Leu Pro Pro Arg
450

<210> SEQ ID NO 29
<211> LENGTH: 454
<212> TYPE: PRT
<213> ORGANISM: Artificial Sequence
<220> FEATURE:
<223> OTHER INFORMATION: CAR comprising T28K, Y32F, A100N, N103M mutations in the VH domain, N35R mutation in the VL domain, IgG1 hinge spacer, TYRP-1 transmembrane domain, and 4-1BB and CD3zeta endodomains

<400> SEQUENCE: 29

Gln Val Gln Leu Val Gln Ser Gly Ala Glu Val Lys Lys Pro Gly Ala
1 5 10 15

Ser Val Lys Val Ser Cys Lys Ala Ser Gly Tyr Lys Phe Thr Gly Phe
20 25 30

Val Met His Trp Val Arg Gln Ala Pro Gly Gln Gly Leu Glu Trp Met
35 40 45

Gly Phe Ile Asn Pro Tyr Asn Asp Asp Ile Gln Ser Asn Glu Arg Phe
50 55 60

Arg Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Asn Gly Phe Met Phe Asp Gly Ala Tyr Arg Phe Phe Asp
100 105 110

```
Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Arg Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Ala
                245                 250                 255

Glu Pro Lys Ser Pro Asp Lys Thr His Thr Cys Pro Pro Cys Pro Lys
            260                 265                 270

Asp Pro Lys Ile Ile Ala Ile Ala Val Val Gly Ala Leu Leu Leu Val
        275                 280                 285

Ala Leu Ile Phe Gly Thr Ala Ser Tyr Leu Ile Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450
```

<210> SEQ ID NO 30
<211> LENGTH: 454
<212> TYPE: PRT
<213> ORGANISM: Artificial Sequence
<220> FEATURE:
<223> OTHER INFORMATION: CAR comprising T28K, Y32F, A100N, Y102L, N103M mutations in the VH domain, N35R mutation in the VL domain, IgG1 hinge spacer, TYRP-1 transmembrane domain, and 4-1BB and CD3zeta endodomains

<400> SEQUENCE: 30

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Leu Met Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Arg Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Ala
                245                 250                 255

Glu Pro Lys Ser Pro Asp Lys Thr His Thr Cys Pro Pro Cys Pro Lys
            260                 265                 270

Asp Pro Lys Ile Ile Ala Ile Ala Val Val Gly Ala Leu Leu Leu Val
        275                 280                 285

Ala Leu Ile Phe Gly Thr Ala Ser Tyr Leu Ile Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
```

420 425 430

Gln Gly Leu Ser Thr Ala Thr Lys Asp Thr Tyr Asp Ala Leu His Met
435 440 445

Gln Ala Leu Pro Pro Arg
450

<210> SEQ ID NO 31
<211> LENGTH: 480
<212> TYPE: PRT
<213> ORGANISM: Artificial Sequence
<220> FEATURE:
<223> OTHER INFORMATION: CAR comprising T28K, Y32F, A100N mutations in the VH domain, CD8 stalk spacer, TYRP-1 transmembrane domain, and 4-1BB and CD3zeta endodomains

<400> SEQUENCE: 31

Gln Val Gln Leu Val Gln Ser Gly Ala Glu Val Lys Lys Pro Gly Ala
1 5 10 15

Ser Val Lys Val Ser Cys Lys Ala Ser Gly Tyr Lys Phe Thr Gly Phe
20 25 30

Val Met His Trp Val Arg Gln Ala Pro Gly Gln Gly Leu Glu Trp Met
35 40 45

Gly Phe Ile Asn Pro Tyr Asn Asp Asp Ile Gln Ser Asn Glu Arg Phe
50 55 60

Arg Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Asn Gly Tyr Asn Phe Asp Gly Ala Tyr Arg Phe Phe Asp
100 105 110

Phe Trp Gly Gln Gly Thr Met Val Thr Val Ser Ser Gly Gly Gly Gly
115 120 125

Ser Gly Gly Gly Gly Ser Gly Gly Gly Gly Ser Asp Ile Val Met Thr
130 135 140

Gln Ser Pro Leu Ser Leu Pro Val Thr Pro Gly Glu Pro Ala Ser Ile
145 150 155 160

Ser Cys Arg Ser Ser Gln Arg Leu Val His Ser Asn Gly Asn Thr Tyr
165 170 175

Leu His Trp Tyr Leu Gln Lys Pro Gly Gln Ser Pro Arg Leu Leu Ile
180 185 190

Tyr Arg Val Ser Asn Arg Phe Pro Gly Val Pro Asp Arg Phe Ser Gly
195 200 205

Ser Gly Ser Gly Thr Asp Phe Thr Leu Lys Ile Ser Arg Val Glu Ala
210 215 220

Glu Asp Val Gly Val Tyr Tyr Cys Ser Gln Ser Thr His Val Pro Tyr
225 230 235 240

Thr Phe Gly Gln Gly Thr Lys Leu Glu Ile Lys Arg Ser Asp Pro Thr
245 250 255

Thr Thr Pro Ala Pro Arg Pro Pro Thr Pro Ala Pro Thr Ile Ala Ser
260 265 270

Gln Pro Leu Ser Leu Arg Pro Glu Ala Cys Arg Pro Ala Ala Gly Gly
275 280 285

Ala Val His Thr Arg Gly Leu Asp Phe Ala Cys Asp Ile Ile Ile Ala
290 295 300

Ile Ala Val Val Gly Ala Leu Leu Leu Val Ala Leu Ile Phe Gly Thr
305 310 315 320

-continued

Ala Ser Tyr Leu Ile Lys Arg Gly Arg Lys Lys Leu Leu Tyr Ile Phe
325 330 335

Lys Gln Pro Phe Met Arg Pro Val Gln Thr Thr Gln Glu Glu Asp Gly
340 345 350

Cys Ser Cys Arg Phe Pro Glu Glu Glu Glu Gly Gly Cys Glu Leu Arg
355 360 365

Arg Val Lys Phe Ser Arg Ser Ala Asp Ala Pro Ala Tyr Gln Gln Gly
370 375 380

Gln Asn Gln Leu Tyr Asn Glu Leu Asn Leu Gly Arg Arg Glu Glu Tyr
385 390 395 400

Asp Val Leu Asp Lys Arg Arg Gly Arg Asp Pro Glu Met Gly Gly Lys
405 410 415

Pro Arg Arg Lys Asn Pro Gln Glu Gly Leu Tyr Asn Glu Leu Gln Lys
420 425 430

Asp Lys Met Ala Glu Ala Tyr Ser Glu Ile Gly Met Lys Gly Glu Arg
435 440 445

Arg Arg Gly Lys Gly His Asp Gly Leu Tyr Gln Gly Leu Ser Thr Ala
450 455 460

Thr Lys Asp Thr Tyr Asp Ala Leu His Met Gln Ala Leu Pro Pro Arg
465 470 475 480

<210> SEQ ID NO 32
<211> LENGTH: 479
<212> TYPE: PRT
<213> ORGANISM: Artificial Sequence
<220> FEATURE:
<223> OTHER INFORMATION: CAR comprising T28K, Y32F, A100N mutations in the VH domain, CD8 stalk spacer, TYRP-1 transmembrane domain, and CD28 and CD3zeta endodomains

<400> SEQUENCE: 32

Gln Val Gln Leu Val Gln Ser Gly Ala Glu Val Lys Lys Pro Gly Ala
1 5 10 15

Ser Val Lys Val Ser Cys Lys Ala Ser Gly Tyr Lys Phe Thr Gly Phe
20 25 30

Val Met His Trp Val Arg Gln Ala Pro Gly Gln Gly Leu Glu Trp Met
35 40 45

Gly Phe Ile Asn Pro Tyr Asn Asp Asp Ile Gln Ser Asn Glu Arg Phe
50 55 60

Arg Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Asn Gly Tyr Asn Phe Asp Gly Ala Tyr Arg Phe Phe Asp
100 105 110

Phe Trp Gly Gln Gly Thr Met Val Thr Val Ser Ser Gly Gly Gly Gly
115 120 125

Ser Gly Gly Gly Gly Ser Gly Gly Gly Gly Ser Asp Ile Val Met Thr
130 135 140

Gln Ser Pro Leu Ser Leu Pro Val Thr Pro Gly Glu Pro Ala Ser Ile
145 150 155 160

Ser Cys Arg Ser Ser Gln Arg Leu Val His Ser Asn Gly Asn Thr Tyr
165 170 175

Leu His Trp Tyr Leu Gln Lys Pro Gly Gln Ser Pro Arg Leu Leu Ile
180 185 190

Tyr Arg Val Ser Asn Arg Phe Pro Gly Val Pro Asp Arg Phe Ser Gly
195 200 205

Ser Gly Ser Gly Thr Asp Phe Thr Leu Lys Ile Ser Arg Val Glu Ala
210 215 220

Glu Asp Val Gly Val Tyr Tyr Cys Ser Gln Ser Thr His Val Pro Tyr
225 230 235 240

Thr Phe Gly Gln Gly Thr Lys Leu Glu Ile Lys Arg Ser Asp Pro Thr
245 250 255

Thr Thr Pro Ala Pro Arg Pro Pro Thr Pro Ala Pro Thr Ile Ala Ser
260 265 270

Gln Pro Leu Ser Leu Arg Pro Glu Ala Cys Arg Pro Ala Ala Gly Gly
275 280 285

Ala Val His Thr Arg Gly Leu Asp Phe Ala Cys Asp Ile Ile Ile Ala
290 295 300

Ile Ala Val Val Gly Ala Leu Leu Leu Val Ala Leu Ile Phe Gly Thr
305 310 315 320

Ala Ser Tyr Leu Ile Arg Ser Lys Arg Ser Arg Leu Leu His Ser Asp
325 330 335

Tyr Met Asn Met Thr Pro Arg Arg Pro Gly Pro Thr Arg Lys His Tyr
340 345 350

Gln Pro Tyr Ala Pro Pro Arg Asp Phe Ala Ala Tyr Arg Ser Arg Arg
355 360 365

Val Lys Phe Ser Arg Ser Ala Asp Ala Pro Ala Tyr Gln Gln Gly Gln
370 375 380

Asn Gln Leu Tyr Asn Glu Leu Asn Leu Gly Arg Arg Glu Glu Tyr Asp
385 390 395 400

Val Leu Asp Lys Arg Arg Gly Arg Asp Pro Glu Met Gly Gly Lys Pro
405 410 415

Arg Arg Lys Asn Pro Gln Glu Gly Leu Tyr Asn Glu Leu Gln Lys Asp
420 425 430

Lys Met Ala Glu Ala Tyr Ser Glu Ile Gly Met Lys Gly Glu Arg Arg
435 440 445

Arg Gly Lys Gly His Asp Gly Leu Tyr Gln Gly Leu Ser Thr Ala Thr
450 455 460

Lys Asp Thr Tyr Asp Ala Leu His Met Gln Ala Leu Pro Pro Arg
465 470 475

<210> SEQ ID NO 33
<211> LENGTH: 453
<212> TYPE: PRT
<213> ORGANISM: Artificial Sequence
<220> FEATURE:
<223> OTHER INFORMATION: CAR comprising T28K, Y32F, A100N mutations in the VH domain, IgG1 hinge spacer, TYRP-1 transmembrane domain, and CD28 and CD3zeta endodomains

<400> SEQUENCE: 33

Gln Val Gln Leu Val Gln Ser Gly Ala Glu Val Lys Lys Pro Gly Ala
1 5 10 15

Ser Val Lys Val Ser Cys Lys Ala Ser Gly Tyr Lys Phe Thr Gly Phe
20 25 30

Val Met His Trp Val Arg Gln Ala Pro Gly Gln Gly Leu Glu Trp Met
35 40 45

Gly Phe Ile Asn Pro Tyr Asn Asp Asp Ile Gln Ser Asn Glu Arg Phe
50 55 60

Arg Gly Arg Val Thr Met Thr Arg Asp Thr Ser Ile Ser Thr Ala Tyr

```
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Asn Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Asn Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Ala
                245                 250                 255

Glu Pro Lys Ser Pro Asp Lys Thr His Thr Cys Pro Pro Cys Pro Lys
            260                 265                 270

Asp Pro Lys Ile Ile Ala Ile Ala Val Val Gly Ala Leu Leu Leu Val
        275                 280                 285

Ala Leu Ile Phe Gly Thr Ala Ser Tyr Leu Ile Arg Ser Lys Arg Ser
    290                 295                 300

Arg Leu Leu His Ser Asp Tyr Met Asn Met Thr Pro Arg Arg Pro Gly
305                 310                 315                 320

Pro Thr Arg Lys His Tyr Gln Pro Tyr Ala Pro Pro Arg Asp Phe Ala
                325                 330                 335

Ala Tyr Arg Ser Arg Arg Val Lys Phe Ser Arg Ser Ala Asp Ala Pro
            340                 345                 350

Ala Tyr Gln Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
        435                 440                 445

Ala Leu Pro Pro Arg
    450
```

<210> SEQ ID NO 34
<211> LENGTH: 453
<212> TYPE: PRT
<213> ORGANISM: Artificial Sequence -continued
<220> FEATURE:
<223> OTHER INFORMATION: CAR comprising T28K, Y32F, A100N mutations in the VH domain, N35K mutation in the VL domain, IgG1 hinge spacer, TYRP-1 transmembrane domain, and CD28 and CD3zeta endodomains

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Asn Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Lys Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Ala
                245                 250                 255

Glu Pro Lys Ser Pro Asp Lys Thr His Thr Cys Pro Pro Cys Pro Lys
            260                 265                 270

Asp Pro Lys Ile Ile Ala Ile Ala Val Val Gly Ala Leu Leu Leu Val
        275                 280                 285

Ala Leu Ile Phe Gly Thr Ala Ser Tyr Leu Ile Arg Ser Lys Arg Ser
    290                 295                 300

Arg Leu Leu His Ser Asp Tyr Met Asn Met Thr Pro Arg Arg Pro Gly
305                 310                 315                 320

Pro Thr Arg Lys His Tyr Gln Pro Tyr Ala Pro Pro Arg Asp Phe Ala
                325                 330                 335

Ala Tyr Arg Ser Arg Arg Val Lys Phe Ser Arg Ser Ala Asp Ala Pro
            340                 345                 350

Ala Tyr Gln Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380
```

```
Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
        435                 440                 445

Ala Leu Pro Pro Arg
    450


<210> SEQ ID NO 35
<211> LENGTH: 480
<212> TYPE: PRT
<213> ORGANISM: Artificial Sequence
<220> FEATURE:
<223> OTHER INFORMATION: CAR comprising T28K, Y32F, A100N mutations in
      the VH domain, N35K mutation in the VL domain, CD8 stalk spacer,
      TYRP-1 transmembrane domain, and 4-1BB and CD3zeta endodomains

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Asn Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160

Ser Cys Arg Ser Ser Gln Arg Leu Val His Ser Asn Gly Lys Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
```

```
        275                 280                 285

Ala Val His Thr Arg Gly Leu Asp Phe Ala Cys Asp Ile Ile Ile Ala
    290                 295                 300

Ile Ala Val Val Gly Ala Leu Leu Leu Val Ala Leu Ile Phe Gly Thr
305                 310                 315                 320

Ala Ser Tyr Leu Ile Lys Arg Gly Arg Lys Lys Leu Leu Tyr Ile Phe
                325                 330                 335

Lys Gln Pro Phe Met Arg Pro Val Gln Thr Thr Gln Glu Glu Asp Gly
            340                 345                 350

Cys Ser Cys Arg Phe Pro Glu Glu Glu Glu Gly Gly Cys Glu Leu Arg
        355                 360                 365

Arg Val Lys Phe Ser Arg Ser Ala Asp Ala Pro Ala Tyr Gln Gln Gly
    370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
            420                 425                 430

Asp Lys Met Ala Glu Ala Tyr Ser Glu Ile Gly Met Lys Gly Glu Arg
        435                 440                 445

Arg Arg Gly Lys Gly His Asp Gly Leu Tyr Gln Gly Leu Ser Thr Ala
    450                 455                 460

Thr Lys Asp Thr Tyr Asp Ala Leu His Met Gln Ala Leu Pro Pro Arg
465                 470                 475                 480


<210> SEQ ID NO 36
<211> LENGTH: 479
<212> TYPE: PRT
<213> ORGANISM: Artificial Sequence
<220> FEATURE:
<223> OTHER INFORMATION: CAR comprising T28K, Y32F, A100N mutations in
      the VH domain, N35K mutation in the VL domain, CD8 stalk spacer,
      TYRP-1 transmembrane domain, and CD28 and CD3zeta endodomains

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Gly Phe
            20                  25                  30

Val Met His Trp Val Arg Gln Ala Pro Gly Gln Gly Leu Glu Trp Met
        35                  40                  45

Gly Phe Ile Asn Pro Tyr Asn Asp Asp Ile Gln Ser Asn Glu Arg Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asn Gly Tyr Asn Phe Asp Gly Ala Tyr Arg Phe Phe Asp
            100                 105                 110

Phe Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Val Met Thr
    130                 135                 140

Gln Ser Pro Leu Ser Leu Pro Val Thr Pro Gly Glu Pro Ala Ser Ile
145                 150                 155                 160
```

-continued

```
Ser Cys Arg Ser Ser Gln Arg Leu Val His Ser Asn Gly Lys Thr Tyr
                165                 170                 175

Leu His Trp Tyr Leu Gln Lys Pro Gly Gln Ser Pro Arg Leu Leu Ile
            180                 185                 190

Tyr Arg Val Ser Asn Arg Phe Pro Gly Val Pro Asp Arg Phe Ser Gly
        195                 200                 205

Ser Gly Ser Gly Thr Asp Phe Thr Leu Lys Ile Ser Arg Val Glu Ala
    210                 215                 220

Glu Asp Val Gly Val Tyr Tyr Cys Ser Gln Ser Thr His Val Pro Tyr
225                 230                 235                 240

Thr Phe Gly Gln Gly Thr Lys Leu Glu Ile Lys Arg Ser Asp Pro Thr
                245                 250                 255

Thr Thr Pro Ala Pro Arg Pro Pro Thr Pro Ala Pro Thr Ile Ala Ser
            260                 265                 270

Gln Pro Leu Ser Leu Arg Pro Glu Ala Cys Arg Pro Ala Ala Gly Gly
        275                 280                 285

Ala Val His Thr Arg Gly Leu Asp Phe Ala Cys Asp Ile Ile Ile Ala
    290                 295                 300

Ile Ala Val Val Gly Ala Leu Leu Leu Val Ala Leu Ile Phe Gly Thr
305                 310                 315                 320

Ala Ser Tyr Leu Ile Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475
```

BINDING DOMAIN

CROSS-REFERENCE TO RELATED APPLICATIONS

This is a U.S. National Phase of International Application No. PCT/GB2019/053100, filed Oct. 31, 2019, which claims priority to Great Britain Application No. 1817822.8 filed Oct. 31, 2018.

FIELD OF THE INVENTION

The present invention relates to variant antigen-binding domains which bind specifically to TRBC2. It also relates to cells and agents useful in the treatment and diagnosis of T-cell malignancies.

BACKGROUND TO THE INVENTION

Lymphoid malignancies can largely be divided into those which are derived from either T-cells or B-cells. T-cell malignancies are a clinically and biologically heterogeneous group of disorders, together comprising 10-20% of non-Hodgkin's lymphomas and 20% of acute leukaemias. The most commonly identified histological subtypes are peripheral T-cell lymphoma, not otherwise specified (PTCL-NOS); angio-immunoblastic T-cell lymphoma (AITL) and anaplastic large cell lymphoma (ALCL). Of all acute Lymphoblastic Leukaemias (ALL), some 20% are of a T-cell phenotype.

These conditions typically behave aggressively, compared for instance with B-cell malignancies, with estimated 5-year survival of only 30%. In the case of T-cell lymphoma, they are associated with a high proportion of patients presenting with disseminated disease, unfavourable International Prognostic Indicator (IPI) score and prevalence of extra-nodal disease. Chemotherapy alone is not usually effective and less than 30% of patients are cured with current treatments.

Further, unlike in B-cell malignancies, where immunotherapies such as the anti-CD20 monoclonal antibody rituximab have dramatically improved outcomes, there is currently no equivalently effective, minimally toxic immunotherapeutic available for the treatment of T-cell malignancies. An important difficulty in the development of immunotherapy for T-cell disorders is the considerable overlap in marker expression of clonal and normal T-cells, with no single antigen clearly able to identify clonal (malignant) cells.

Chimeric antigen receptors (CARs) T-cells have shown promise in the treatment of refractory B-cell malignancies. Targeting T cell malignancies is likely to be equally efficacious, but the application of CARs in diseases such as T-cell lymphoma has been hampered by a paucity of suitable target antigens. Unlike B cell lymphomas in which ablation of the B cell compartment is a manageable toxicity and can be treated with the administration of intravenous immunoglobulin, destroying the T cell compartment will not be well tolerated and will lead to complications associated with suppression of cell mediated immunity.

A method for treating T cell lymphomas and leukaemias consisting in targeting the constant region of the TCR beta chain (TRBC) has been previously described in WO2015/132598. This approach is based on a unique feature of the T cell receptor, i.e. that each TCR encodes either TRBC1 or TRBC2 in a mutually exclusive fashion. Because T-cell lymphomas and leukaemias are a clonal population of cells, each lymphoma will express one TCR, with either TRBC1 or TRBC2, on the surface.

The monoclonal antibody Jovi-1 specifically binds to TRBC1 and has been used as the CAR binding domain for a therapy treating T cell lymphomas (Maciocia et al., 2017, Nat Med 23:1416-23; WO2015/132598). This proposed therapy allows the treatment of a subset of patients that express a TCR with the TRBC1 constant region.

In order to treat the entire patient population a binder/CAR targeting TRBC2 is necessary. One method for obtaining antibodies which are specific to TRBC2 is by phage selections on a human phage display library. Another method consists in immunising animals with TRBC2-derived peptides and subsequently selecting specific antibodies. Both these approaches have been carried out with success and various TRBC2-specific binders were generated, as disclosed in WO2015/132598.

The present invention provides alternative binders that are specific for TRBC2 and which are potential therapeutic agents for the treatment of TRBC2+ lymphomas or leukaemias.

SUMMARY OF ASPECTS OF THE INVENTION

The present inventors have solved the crystal structure of JOVI-1 (Viney et al., 1992, Hybridoma 11:701-13), a TRBC1 specific monoclonal antibody, in complex with a TRBC1-TCR to 2.4 Å (FIG. 3). From the crystal structure it has been possible to engineer the original Jovi-1 antibody to bind to TRBC2. This method is particularly attractive as a number of amino acids within the antibody form the paratope which provide shape complementarity to enable engagement of the TCR, while only a few will be required for specificity to TRBC1. Through computational biology and protein engineering, the inventors have rationally designed mutant versions of TRBC1 binders that are specific for TRBC2 and have a decreased affinity towards TRBC1.

Thus, in a first aspect, the present invention provides a variant antigen-binding domain which comprises at least one mutation in the VH domain compared to a reference antibody having a VH domain with the sequence shown in SEQ ID NO: 1 and a VL domain with the sequence shown in SEQ ID NO: 2, in which at least one mutation in the VH domain is selected from T28K, Y32K and A100N, and wherein the variant antigen-binding domain displays an increased affinity for TRBC2 over the reference antibody.

The variant antigen-binding domain may comprise at least two mutations in the VH domain selected from T28K, Y32K and A100N. For example, it may comprise mutations Y32K and A100N. The variant antigen-binding domain may further comprise mutation T28R in the VH domain or, alternatively, mutation G31K in the VH domain.

The variant antigen-binding domain may comprise T28K, Y32K and A100N mutations.

The variant antigen-binding domain may further comprise at least one mutation at a position selected from the group consisting of V2, Y27, G31, R98, Y102, N103, and A107 in the VH domain, N35 in the VL domain, and R55 in the VL domain. The at least one further mutation may be selected from:

a) in the VH domain:
   V2K, V2R,
   Y27F, Y27M, Y27N, Y27W,
   G31K, G31R, G31S,
   R98K,
   Y102F, Y102L, N103A, N103E, N103F, N103H, N103L, N103M, N103Q, N103S, N103W, N103Y,
A107S,
and
b) in the VL domain:
N35M, N35F, N35Y, N35K, N35R, and
R55K.

The variant antigen-binding domain may be selected from a variant antigen-binding domain comprising the following mutation combinations:

T28K, Y32F, A100N in the VH domain and N35K in the VL domain,
T28K, Y32F, A100N in the VH domain,
T28K, Y32F, A100N, Y27N in the VH domain
T28K, Y32F, A100N, G31K in the VH domain
T28K, Y32F, A100N, Y27M in the VH domain
T28K, Y32F, A100N, Y27W in the VH domain
T28K, Y32F, A100N in the VH domain and R55K in the VL domain,
T28K, Y32F, A100N, N103H in the VH domain
T28K, Y32F, A100N, N103A in the VH domain
T28K, Y32F, A100N, N103Y in the VH domain
T28K, Y32F, A100N in the VH domain and N35R in the VL domain,
T28K, Y32F, A100N, N103S in the VH domain and N35M in the VL domain,
T28K, Y32F, A100N, N103M, in the VH domain,
T28K, Y32F, A100N, N103W in the VH domain and N35R in the VL domain,
T28K, Y32F, A100N in the VH domain and N35F in the VL domain,
T28K, Y32F, A100N, N103S in the VH domain and N35K in the VL domain,
T28K, Y32F, A100N, R98K in the VH domain,
T28K, Y32F, A100N, N103S in the VH domain and N35R in the VL domain,
T28K, Y32F, A100N, N103L in the VH domain,
T28K, Y32F, A100N, N103S in the VH domain and N35F in the VL domain,
T28K, Y32F, A100N, N103S in the VH domain and N35Y in the VL domain,
T28K, Y32F, A100N, N103L in the VH domain and N35M in the VL domain,
T28K, Y32F, A100N, N103L in the VH domain and N35R in the VL domain,
T28K, Y32F, A100N, N103W in the VH domain and N35K in the VL domain,
T28K, Y32F, A100N, N103L in the VH domain and N35Y in the VL domain,
T28K, Y32F, A100N, N103F in the VH domain,
T28K, Y32F, A100N, N103W in the VH domain,
T28K, Y32F, A100N, N103L in the VH domain and N35K in the VL domain,
T28K, Y32F, A100N, N103L in the VH domain and N35F in the VL domain,
T28K, Y32F, A100N, N103W in the VH domain and N35M in the VL domain,
T28K, Y32F, A100N, N103F in the VH domain and N35Y in the VL domain,
T28K, Y32F, A100N, Y27F in the VH domain,
T28K, Y32F, A100N, N103Q in the VH domain,
T28K, Y32F, A100N, N103S in the VH domain,
T28K, Y32F, A100N, N103M in the VH domain and N35F in the VL domain,
T28K, Y32F, A100N, N103F in the VH domain and N35M in the VL domain,
T28K, Y32F, A100N, N103F in the VH domain and N35F in the VL domain,
T28K, Y32F, A100N, G31R in the VH domain,
T28K, Y32F, A100N, N103W in the VH domain and N35F in the VL domain,
T28K, Y32F, A100N, V2R in the VH domain,
T28K, Y32F, A100N, G31S in the VH domain,
T28K, Y32F, A100N, A107S in the VH domain,
T28K, Y32F, A100N, N103E in the VH domain and N35M in the VL domain,
T28K, Y32F, A100N, V2K in the VH domain,
T28K, Y32F, A100N, N103E in the VH domain
T28K, Y32F, A100N, Y102F, N103M in the VH domain and N35K in the VL domain,
T28K, Y32F, A100N, Y102F, N103M in the VH domain and N35F in the VL domain,
T28K, Y32F, A100N, Y102F, N103M in the VH domain and N35R in the VL domain,
T28K, Y32F, A100N, Y102F in the VH domain and N35R in the VL domain,
T28K, Y32F, A100N, N103M in the VH domain and N35M in the VL domain,
T28K, Y32F, A100N, N103M in the VH domain and N35Y in the VL domain,
T28K, Y32F, A100N, N103M in the VH domain and N35R in the VL domain,
T28K, Y32F, A100N, N103F in the VH domain and N35K in the VL domain,
T28K, Y32F, A100N, Y102L, N103W in the VH domain and N35R in the VL domain,
T28K, Y32F, A100N, Y102L, N103W in the VH domain and N35K in the VL domain,
T28K, Y32F, A100N, Y102F in the VH domain, and
T28K, Y32F, A100N, Y102L, N103M in the VH domain and N35R in the VL domain.

The variant antigen-binding domain may comprise T28K, Y32F, A100N mutations in the VH domain and N35K mutation in the VL domain.

The variant antigen-binding domain may comprise T28K, Y32F, and A100N mutations in the VH domain.

The variant antigen-binding domain may further display a decreased affinity for TRBC1 over the reference antibody.

The ratio of the affinities of the variant antigen-binding domain for TRBC2 and TRBC1 by be at least 2.

The ratio of the affinities of the variant antigen-binding domain for TRBC2 and TRBC1 by be at least 5.

The ratio of the affinities of the variant antigen-binding domain for TRBC2 and TRBC1 by be at least 10.

The variant antigen-binding domain may further comprise an oligomerisation domain.

In a second aspect, the present invention provides an antibody comprising a variant antigen-binding domain according to the first aspect of the invention.

In a third aspect, the present invention provides a chimeric antigen receptor (CAR) comprising a variant antigen-binding domain according to the first aspect of the invention, a spacer, a transmembrane domain and an endodomain.

The spacer may be selected from a human CD8 stalk as shown in SEQ ID NO: 7 and a COMP spacer as shown in SEQ ID NO: 19

In a fourth aspect, the present invention provides a bispecific T-cell engager (BiTE) comprising a variant antigen-binding domain according to the first aspect of the invention and a T-cell activation domain.

In a fifth aspect, the present invention provides a nucleic acid sequence encoding a variant antigen-binding domain according to the first aspect of the invention, an antibody according to the second aspect of the invention, a CAR according to the third aspect of the invention, or a BiTE according to fourth aspect of the invention.

In a sixth aspect, the present invention provides a vector comprising a nucleic acid sequence according to the fifth aspect of the invention.

In a seventh aspect, the present invention provides a cell which comprises a CAR according to the third aspect of the invention.

In an eighth aspect, the present invention provides a method for making a cell according to the seventh aspect of the invention, which comprises the step of transducing or transfecting a cell with a vector according to sixth aspect of the invention which comprises a nucleic acid sequence encoding the CAR.

In a ninth aspect, the present invention provides a conjugate comprising a variant antigen-binding domain according to the first aspect of the invention, or an antibody according to the second aspect of the invention, and a detectable entity or a chemotherapeutic entity.

The conjugate may comprise a chemotherapeutic entity.

In a tenth aspect, the present invention provides a method for treating a T-cell lymphoma or leukaemia in a subject which comprises the step of administering a cell according to the seventh aspect of the invention, or an antibody according to the second aspect of the invention, or a BiTE according to the fourth aspect of the invention, or a conjugate according to the ninth aspect of the invention to a subject, wherein the malignant T-cells express TRBC2.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

In an eleventh aspect, the present invention provides a cell according to the seventh aspect of the invention, or an antibody according to the second aspect of the invention, or a BiTE according to the fourth aspect of the invention, or a conjugate according to the ninth aspect of the invention for use in medicine.

In a twelfth aspect, the present invention provides a cell according to the seventh aspect of the invention, or an antibody according to the second aspect of the invention, or a BiTE according to the fourth aspect of the invention, or a conjugate according to the ninth aspect of the invention for use in the treatment of a T-cell lymphoma or leukaemia, wherein the malignant T-cells express TRBC2.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

In a thirteenth aspect, the present invention provides the use of a cell according to the seventh aspect of the invention, or an antibody according to the second aspect of the invention, or a BiTE according to the fourth aspect of the invention, or a conjugate according to the ninth aspect of the invention in the manufacture of a medicament for treating a T-cell lymphoma or leukaemia, wherein the malignant T-cells express TRBC2.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

In a fourteenth aspect, the present invention provides a diagnostic agent which comprises a variant antigen-binding domain according to the first aspect of the invention, or an antibody according to the second aspect of the invention.

The diagnostic agent may be for diagnosing a T-cell lymphoma or leukaemia.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

In a fifteenth aspect, the present invention provides a method for diagnosing a T-cell lymphoma or leukaemia in a subject which comprises the step of contacting a variant antigen-binding domain according to the first aspect of the invention, or an antibody according to the second aspect of the invention, to a sample comprising T-cells from the subject.

The method for diagnosing a T-cell lymphoma or leukaemia in a subject may further comprise a step of determining the percentage of TRBC2 positive T-cells in the sample.

A percentage of 70% or more TRBC2 positive T-cells in the sample may be indicative of the presence of a T-cell lymphoma or leukaemia.

The sample may be, or may be derived from, a blood sample.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

In a sixteenth aspect, the present invention provides a method for identifying subjects with a T-cell lymphoma or leukaemia eligible for treatment with a cell according to the seventh aspect of the invention, or an antibody according to the second aspect of the invention, or a BiTE according to the fourth aspect of the invention, or a conjugate according to the ninth aspect of the invention, comprising determining the percentage of TRBC2 positive T-cells in a sample comprising T-cells from the subject.

The subject may be eligible for said treatment with a cell according to the seventh aspect of the invention, or an antibody according to the second aspect of the invention, or a BiTE according to the fourth aspect of the invention, or a conjugate according to the ninth aspect of the invention if the percentage of TRBC2 positive T-cells in the sample is 70% or more.

The sample may be, or may be derived from, a blood sample.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

In a seventeenth aspect, the present invention provides a method for selecting a therapy comprising a cell according to the seventh aspect of the invention, or an antibody according to the second aspect of the invention, or a BiTE according to the fourth aspect of the invention, or a conjugate according to the ninth aspect of the invention for the treatment of a subject, comprising determining the percentage of TRBC2 positive T-cells in a sample comprising T-cells from the subject.

Said therapy may be selected to treat said subject if the percentage of TRBC2 positive T-cells in the sample is 70% or more.

The sample may be, or may be derived from, a blood sample.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

Production of IFN-γ by (A) the anti-TRBC2 triple mutant CAR, and (B) the anti-TRBC1 CAR, incubated in the presence of TRBC1 or TRBC2.

Figure 6:
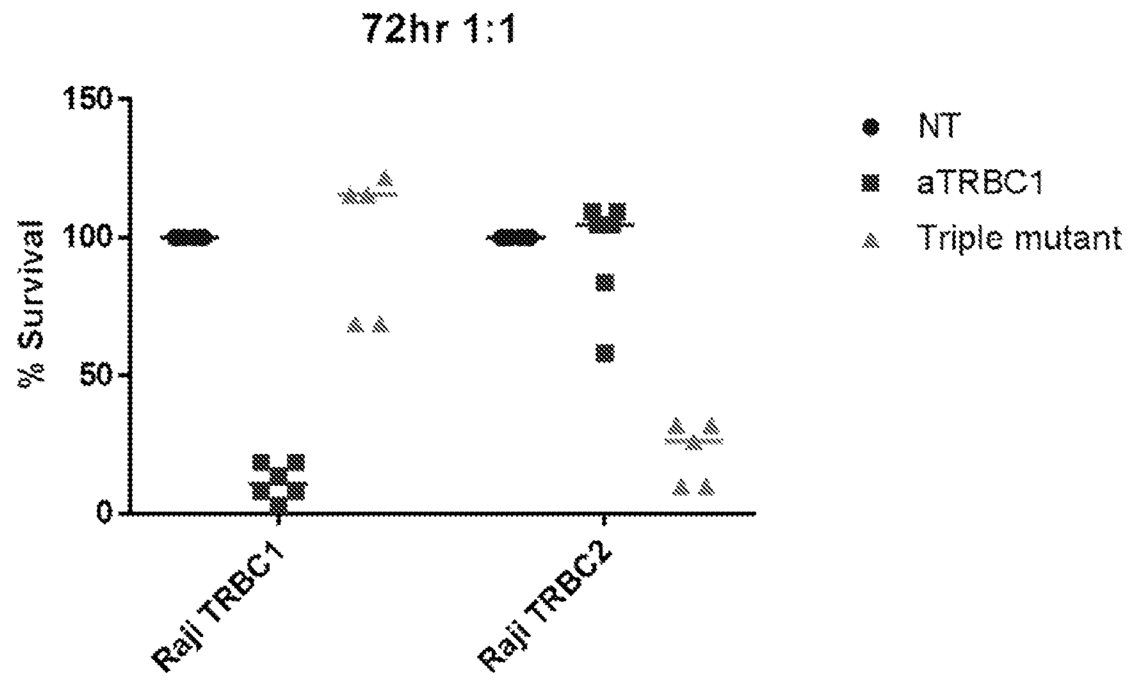

FIG. 6. Cytotoxic activity of (A) the anti-TRBC2 triple mutant CAR-T cells, and (B) the anti-TRBC1 CAR-T cells, co-incubated with Raji WT, Raji $TRBC1^+$ or Raji $TRBC2^+$ cells.

Figure 7:
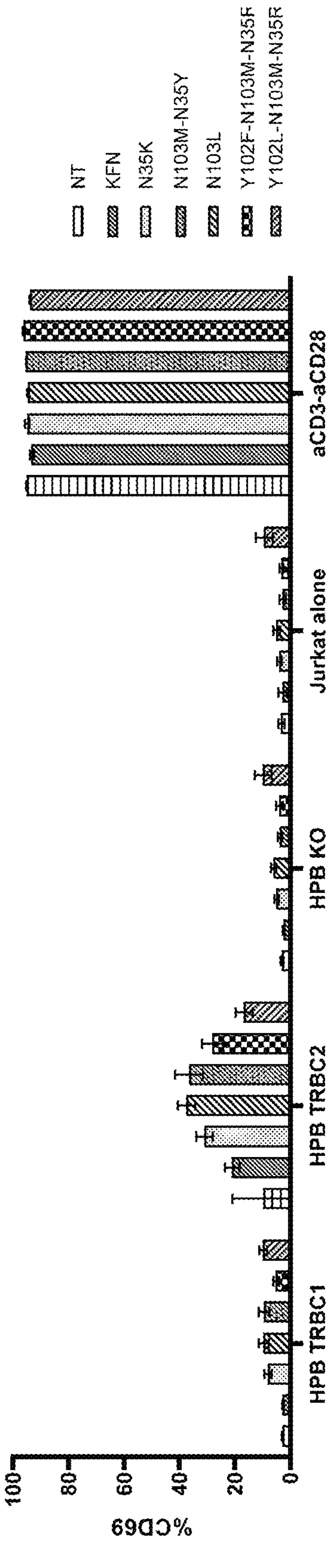

FIG. 7. Antigen-specific activation of Jurkat cells transduced with anti-TRBC2 CARs that were co-incubated with HPB TRBC1 and HPB TRBC2 cells. Jurkat cells (TRBC1+) were transduced with second generation anti-TRBC2 CAR constructs and co-incubated with HPB TRBC1 and HPB TRBC2 cells at a 1:1 E:T ratio. Controls included non-transduced Jurkat cells (NT), HPB-ALL cells having a knocked-out TCR (termed HPB KO) and transduced Jurkat cells plated on their own as negative controls, or with αCD3/αCD28 antibodies as positive assay control, respectively. N35K: binder having T28K, Y32F, A100N mutations in the VH domain and N35K in the VL domain of hJovi-1; N103L: binder having T28K, Y32F, A100N, N103L mutations in the VH domain of hJovi-1; N103M-N35Y: binder having T28K, Y32F, A100N, N103M mutations in the VH domain and N35Y in the VL domain of hJovi-1; Y102F-N103M-N35R: binder having T28K, Y32F, A100N, Y102F, N103M mutations in the VH domain and N35R in the VL domain of hJovi-1; and Y102L-N103M-N35R: binder having T28K, Y32F, A100N, Y102L, N103M mutations in the VH domain and N35R in the VL domain of hJovi-1.

Figure 8:
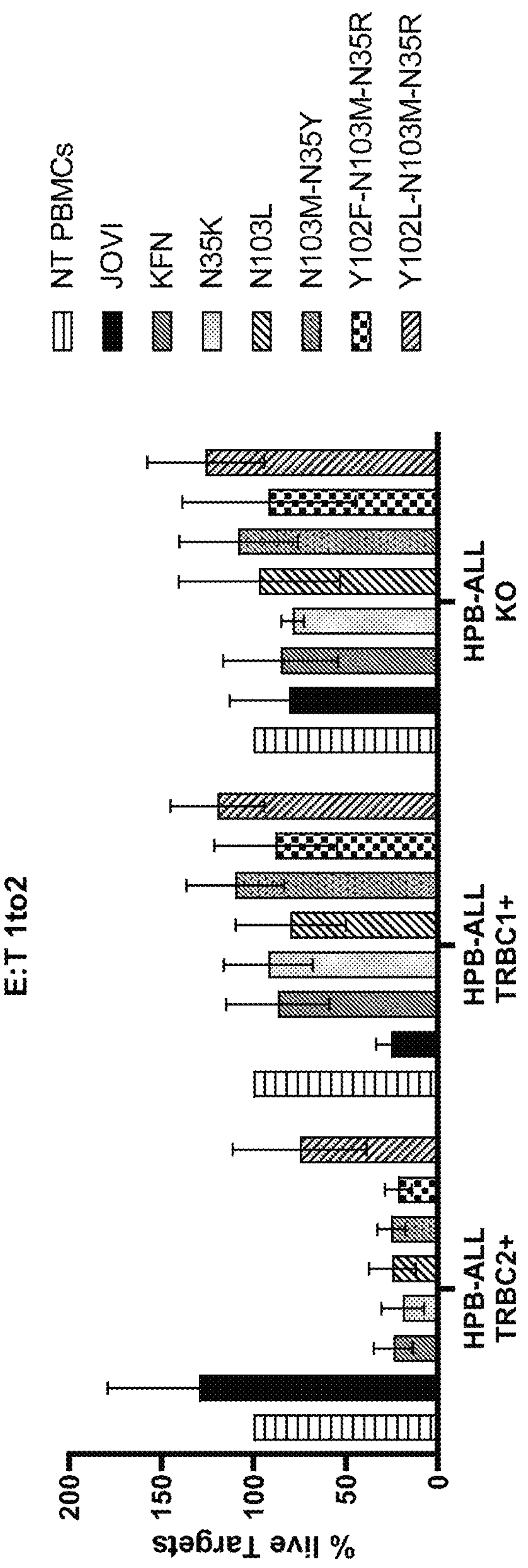

FIG. 8. Cytotoxic activity of anti-TRBC2 CAR-T cells co-incubated with TRBC1+HPB-ALL and TRBC2+HPB-ALL cells. Peripheral blood mononuclear cells (PBMCs) were transduced with second generation anti-TRBC2 CAR constructs. Transduced PBMCs were co-incubated with TRBC1+HPB-ALL and TRBC2+HPB-ALL cells at a 1:2 E:T ratio. Controls included non-transduced cells (NT), cells transduced with anti-TRBC1 hJovi-1 CAR (JOVI), and HPB-ALL cells having a knocked-out TCR (HPB-KO). N35K: binder having T28K, Y32F, A100N mutations in the VH domain and N35K in the VL domain of hJovi-1; N103L: binder having T28K, Y32F, A100N, N103L mutations in the VH domain of hJovi-1; N103M-N35Y: binder having T28K, Y32F, A100N, N103M mutations in the VH domain and N35Y in the VL domain of hJovi-1; Y102F-N103M-N35R: binder having T28K, Y32F, A100N, Y102F, N103M mutations in the VH domain and N35R in the VL domain of hJovi-1; and Y102L-N103M-N35R: binder having T28K, Y32F, A100N, Y102L, N103M mutations in the VH domain and N35R in the VL domain of hJovi-1.

Figure 9:
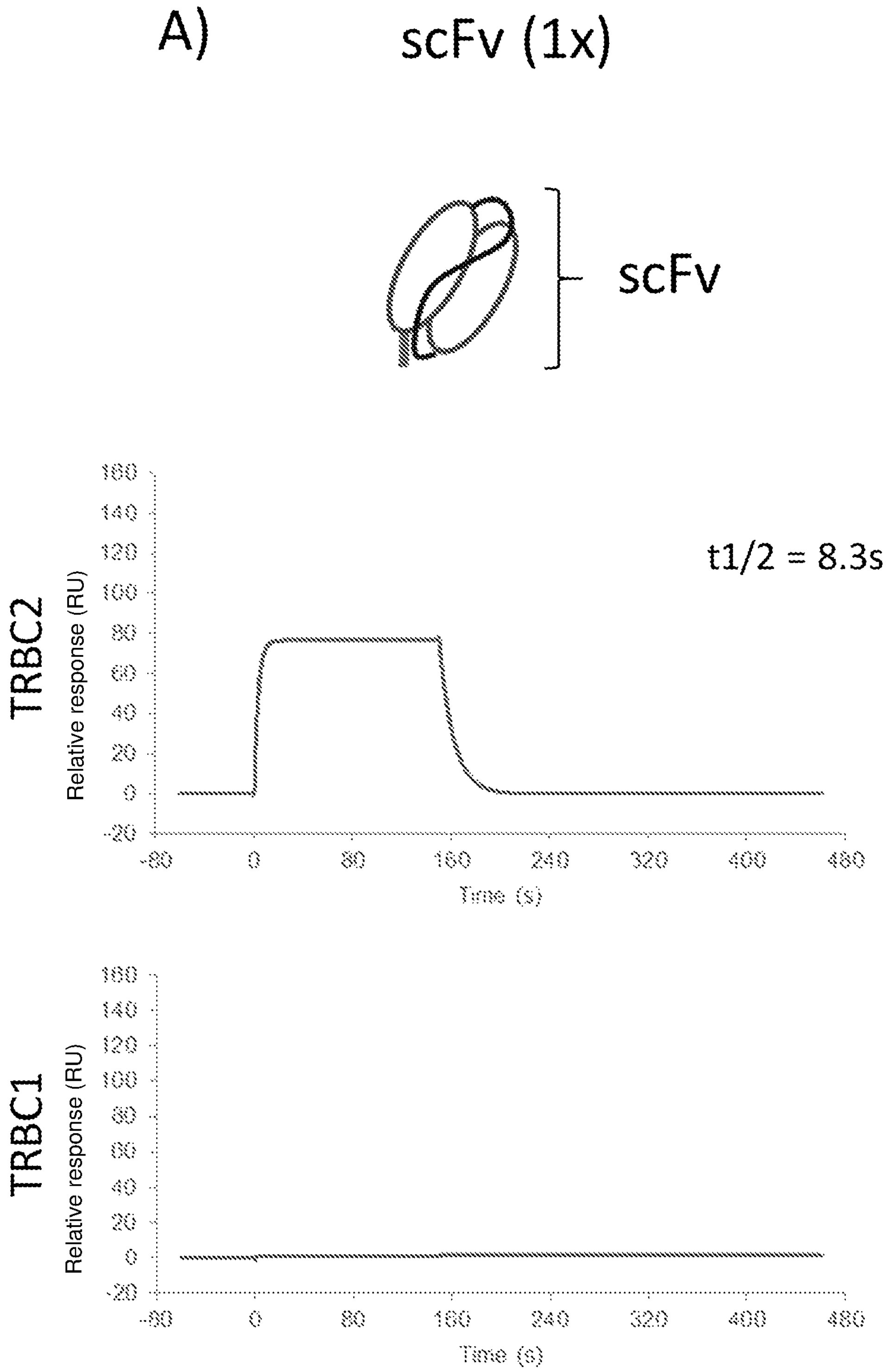
Figure 9:
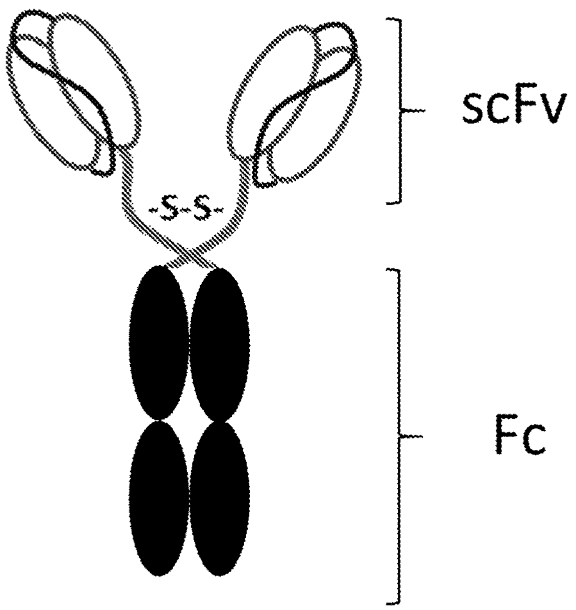
Figure 9:
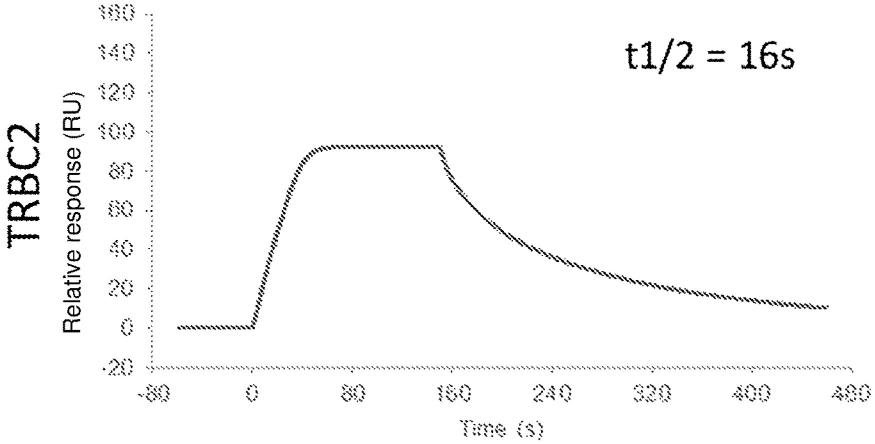
Figure 9:
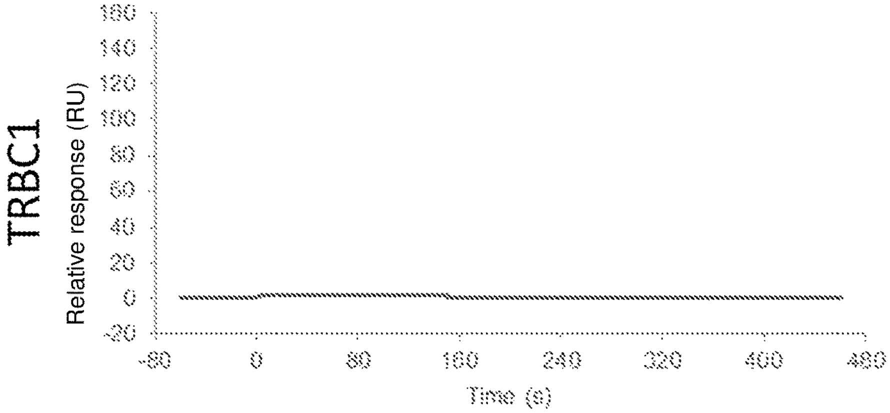
Figure 9:
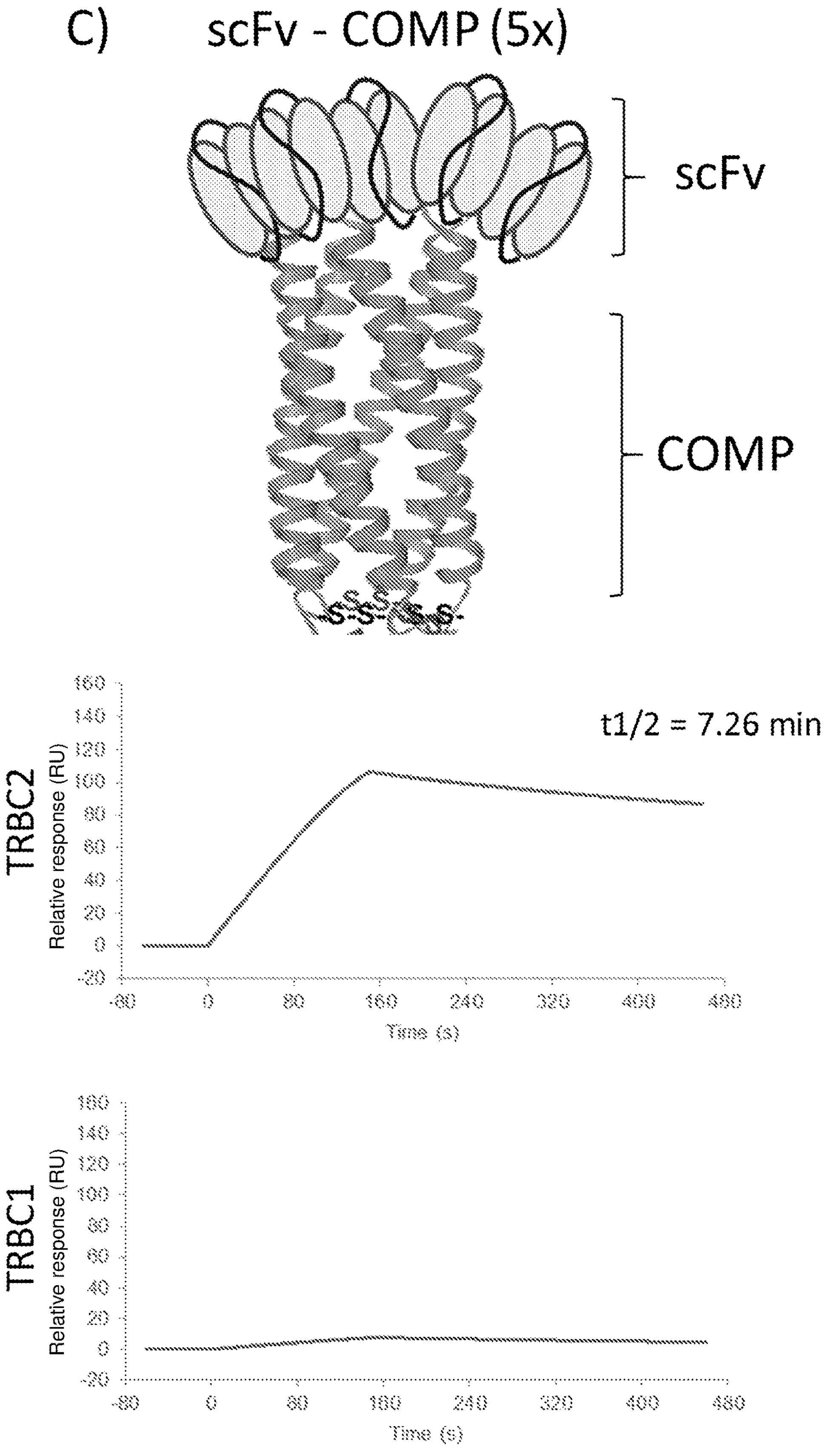

FIG. 9. Analysis of the effect of different antibody formats in the binding of anti-TRBC2 antibodies by surface plasmon resonance (SPR).

DETAILED DESCRIPTION OF THE INVENTION

Figure 1:
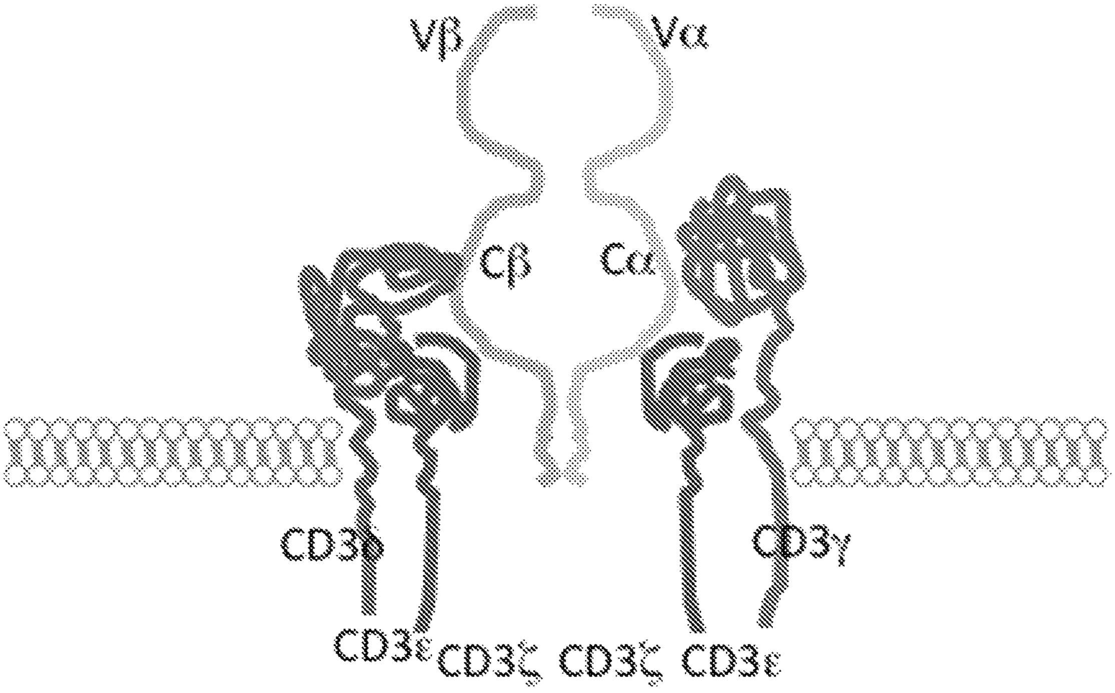
FIG. 1. A diagram of the αβ T-cell Receptor/CD3 Complex. The T-cell receptor is formed from 6 different protein chains which must assemble in the endoplasmic reticulum to be expressed on the cell surface. The four proteins of the CD3 complex (CD3ζ, CD3γ, CD3ε and CD3δ) sheath the T-cell Receptor (TCR). This TCR imbues the complex with specificity of a particular antigen and is composed of two chains: TCRα and TCRβ. Each TCR chain has a variable component distal to the membrane and a constant component proximal to the membrane. Nearly all T-cell lymphomas and many T-cell leukaemias express the TCR/CD3 complex.

The present inventors have solved the crystal structure of Jovi-1, which has served to identify two key residues that are essential for TRBC1 specificity (FIG. 1). Interestingly these residues lie in CDR 1 as opposed to CDR 3, which usually drives antibody specificity. In addition, other residues that lie in close proximity to the TRBC1 epitope will likely be essential to engineer specificity from to TRBC1 to TRBC2. Residues in Jovi-1 that are involved in the binding of TRBC1 or that are of importance to generate TRBC2 specificity are described herein.

The present invention provides variants of the antigen-binding domain of JOVI-1 having an increased affinity for TCR beta constant region 2 (TRBC2) than JOVI-1.

1. TCR β constant region (TRBC)

The T-cell receptor (TCR) is expressed on the surface of T lymphocytes and is responsible for recognizing antigens bound to major histocompatibility complex (MHC) molecules. When the TCR engages with antigenic peptide and MHC (peptide/MHC), the T lymphocyte is activated through a series of biochemical events mediated by associated enzymes, co-receptors, specialized adaptor molecules, and activated or released transcription factors.

The TCR is a disulfide-linked membrane-anchored heterodimer normally consisting of the highly variable alpha (α) and beta (β) chains expressed as part of a complex with the invariant CD3 chain molecules. T-cells expressing this receptor are referred to as α:β (or αβ) T-cells (~95% total T-cells). A minority of T-cells express an alternate receptor, formed by variable gamma (γ) and delta (δ) chains, and are referred to as γδ T-cells (~5% total T cells).

Each α and β chain is composed of two extracellular domains: Variable (V) region and a Constant (C) region, both of Immunoglobulin superfamily (IgSF) domain forming antiparallel β-sheets. The constant region is proximal to the cell membrane, followed by a transmembrane region and a short cytoplasmic tail, while the variable region binds to the peptide/MHC complex. The constant region of the TCR consists of short connecting sequences in which a cysteine residue forms disulfide bonds, which forms a link between the two chains.

The variable domains of both the TCR α-chain and β-chain have three hypervariable or complementarity determining regions (CDRs). The variable region of the β-chain also has an additional area of hypervariability (HV4), however, this does not normally contact antigen and is therefore not considered a CDR.

The TCR also comprises up to five invariant chains γ,δ,ε (collectively termed CD3) and ζ. The CD3 and subunits mediate TCR signalling through specific cytoplasmic domains which interact with second-messenger and adapter molecules following the recognition of the antigen by αβ or γδ. Cell-surface expression of the TCR complex is preceded by the pair-wise assembly of subunits in which both the transmembrane and extracellular domains of TCR α and β and CD3 γ and δ play a role TCRs are therefore commonly composed of the CD3 complex and the TCR α and β chains, which are in turn composed of variable and constant regions (FIG. 1).

Figure 2:
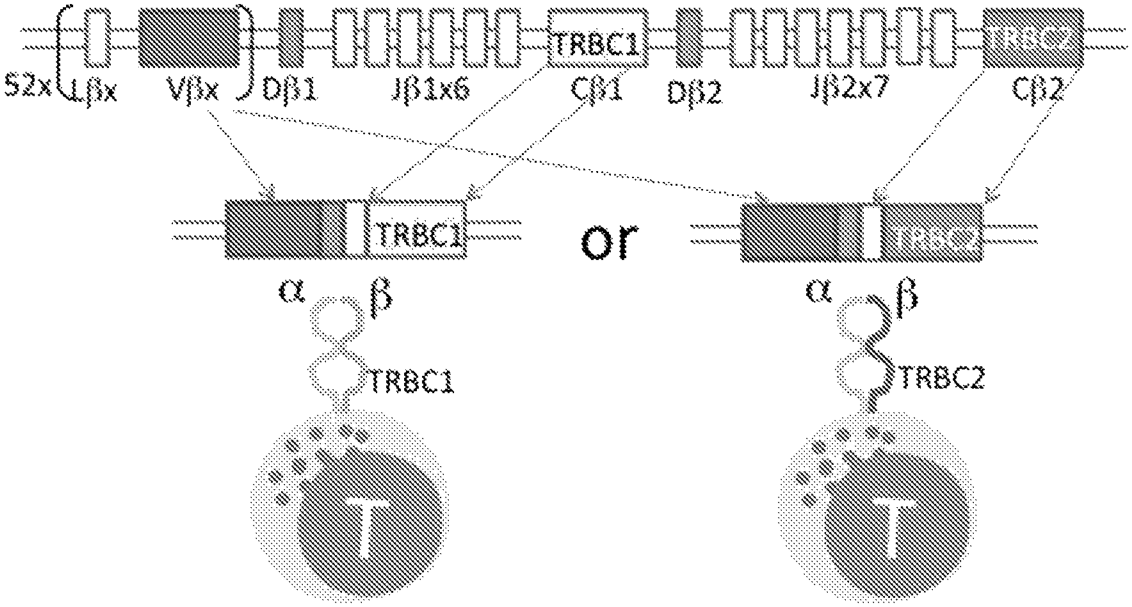
FIG. 2. The segregation of T-cell Receptor β-constant region (TRBC)-1 and TRBC2 during T-cell receptor rearrangement. Each TCR beta chain is formed from genomic recombination of a particular beta variable (V), diversity (D), joining (J) and constant (TRBC) regions. The human genome contains two very similar and functionally equivalent TRBC loci known as TRBC1 and TRBC2. During TCR gene re-arrangement, a J-region recombines with either TRBC1 or TRBC2. This rearrangement is permanent. T-cells express many copies of a single TCR on their surface, hence each T-cell will express a TCR whose β-chain constant region is coded for by either TRBC1 or TRBC2.

The locus (Chr7:q34) which supplies the TCR β-constant region (TRBC) has duplicated in evolutionary history to produce two almost identical and functionally equivalent genes: TRBC1 and TRBC2 (FIG. 2). Each TCR will comprise, in a mutually exclusive fashion, either TRBC1 or TRBC2 and as such, each αβ T-cell will express either TRBC1 or TRBC2, in a mutually exclusive manner.

The present inventors have previously determined that, despite the similarity between the sequence of the TRBC1 and TRBC2, it is possible to discriminate between them. The inventors have also previously determined that amino acid sequences of TRBC1 and TRBC2 can be discriminated whilst in situ on the surface of a cell, for example a T-cell (WO2015/132598).

2. Variant Antigen-Binding Domain

In a first aspect, the present invention provides a variant antigen-binding domain, hereinafter "the variant antigen-binding domain of the invention", which comprises at least one mutation in the VH domain compared to a reference antibody having a VH domain with the sequence shown in SEQ ID NO: 1 and a VL domain with the sequence shown in SEQ ID NO: 2, in which the at least one mutation in the VH domain is selected from T28K, Y32F and A100N, and wherein the variant antigen-binding domain displays an increased affinity for TRBC2 over the reference antibody.

The term "variant" or "mutant", as used herein, refers to a polypeptide differing from a specifically recited polypeptide, i.e. reference or parent polypeptide by amino acid insertions, deletions, and/or substitutions, created using, for example, recombinant DNA techniques or by de novo synthesis. Variant and mutant are used indistinctly in the context of the present invention. Variant antigen-binding domains of the present invention include antigen binding molecules wherein one or several of the amino acid residues are modified by substitution, addition and/or deletion in such manner that affects substantially the antigen binding affinity of the reference or parent antigen-binding domain.

The term "antigen-binding domain", as used herein, refers to the variable regions of each pair of light and heavy chains of the antibody, i.e. the VL and VH domains, respectively, which form its binding site. They are characterised by the same general structure constituted by relatively preserved regions called frameworks (FR) joined by three hypervariable regions called complementarity determining regions (CDR) (Kabat et al., 1991, Sequences of Proteins of Immunological Interest, 5$^{th}$ Ed., NIH Publication No. 91-3242, Bethesda, MD; Chothia & Lesk, 1987, J Mol Biol 196:901-17). The term "complementarity determining region" or "CDR", as used herein, refers to the region within an antibody that complements an antigen's shape. Thus, CDRs determine the protein's affinity (roughly, binding strength) and specificity for specific antigens. The CDRs of the two chains of each pair are aligned by the framework regions, acquiring the function of binding a specific epitope.

The variant antigen-binding domain of the invention comprises at least one mutation in the VH domain compared to a reference antibody. As used herein, the term "reference antibody" refers to a humanised JOVI-1 antibody, i.e. hJOVI-1, which comprises a VH domain with the sequence shown in SEQ ID NO: 1 and a VL domain with the sequence shown in SEQ ID NO: 2. Murine JOVI-1 has been previously disclosed by Viney et al. (1992; as above) and is available commercially (Abcam, ab5465). It has been previously determined that JOVI-1 is able to discriminate cells based on specific expression of TRBC1 or TRBC2 by specifically binding solely to TRBC1 (WO 2015/132598).

```
(VH domain of hJOVI-1):
                                        SEQ ID NO: 1
QVQLVQSGAEVKKPGASVKVSCKASGYTFTGYVMHWVRQAPGQGLEWMGF

INPYNDDIQSNERFRGRVTMTRDTSISTAYMELSRLRSDDTAVYYCARGA

GYNFDGAYRFFDFWGQGTMVTVSS

(VL domain of hJOVI-1):
                                        SEQ ID NO: 2
DIVMTQSPLSLPVTPGEPASISCRSSQRLVHSNGNTYLHWYLQKPGQSPR

LLIYRVSNRFPGVPDRFSGSGSGTDFTLKISRVEAEDVGVYYCSQSTHVP

YTFGQGTKLEIK
```

Hereinafter, any reference to the VH domain means the VH domain of hJOVI-1 shown in SEQ ID NO: 1, unless otherwise stipulated, and any reference to the VL domain means the VL domain of hJOVI-1 shown in SEQ ID NO: 2, unless otherwise stipulated.

The present inventors have determined that the presence of at least one mutation selected from T28K, Y32F and A100N in the VH domain of the reference antibody triggers an increase in affinity for TRBC2 of the variant antigen-binding domain of the invention over the reference antibody (Example 1).

The term "affinity", as used herein, refers to the strength of interaction between an antibody's antigen binding site and an epitope. High-affinity antibodies will bind a greater amount of antigen in a shorter period of time than low-affinity antibodies. Affinity is usually measured as the equilibrium dissociation constant ($K_D$), which is a ratio of $k_{off}/k_{on}$, between the antibody and the antigen. The affinity of an antigen-binding domain for any given antigen may be quantified using any conventional method including, without limitation, labelled-dependent methods, such as direct and indirect ELISA and radioimmunoassay methods, as well as label-free methods which enable a direct detection and measurement of interactions in real-time, such as surface plasmon resonance and bio-layer interference.

The affinity of the variant antigen-binding domain of the invention for TRBC2 is increased over that of the reference antibody. The affinity of the variant antigen-binding domain for TRBC2 may be increased in at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 300%, at least 400%, at least 500%, at least 600%, at least 700%, at least 800%, at least 900%, at least 1,000%, at least 5,000%, or at least 10,000% over the affinity of the reference antibody for TRBC2.

The variant antigen-binding domain of the invention may comprise the T28K mutation in the VH domain. The variant antigen-binding domain of the invention may comprise the Y32F mutation in the VH domain. The variant antigen-binding domain of the invention may comprise the A100N mutation in the VH domain.

The variant antigen-binding domain of the invention may comprise at least two mutations in the VH domain selected from T28K, Y32F and A100N. The at least two mutations may be Y32F and A100N. In an embodiment, the variant antigen-binding domain of the invention may comprise mutations Y32F and A100N and further comprise mutation T28R in the VH domain. In another embodiment, the variant antigen-binding domain of the invention may comprise mutations Y32F and A100N and further comprise mutation G31R in the VH domain.

The variant antigen-binding domain of the invention may comprise mutations T28K, Y32F and A100N in the VH domain.

In another embodiment, the variant antigen-binding domain of the invention comprises mutations T28K, Y32F and A100N in the VH domain and further comprises at least one mutation at a position selected from the group consisting of V2, Y27, G31, R98, Y102, N103, and A107 in the VH domain, and N35 and R55 in the VL domain. The variant antigen-binding domain of the invention may comprise one, two, three, four, five, six or seven mutations at a position selected from the group consisting of V2, Y27, G31, R98, Y102, N103, and A107 in the VH domain, and N35 and R55 in the VL domain.

The variant antigen-binding domain of the invention may comprise mutations T28K, Y32F and A100N in the VH domain and may further comprise a mutation at position V2 in the VH domain, a mutation at position Y27 in the VH domain, a mutation at position G31 in the VH domain, a mutation at position R98 in the VH domain, a mutation at position Y102 in the VH domain, a mutation at position N103 in the VH domain, a mutation at position A107 in the VH domain, a mutation at position N35 in the VL domain, and a mutation at position R55 in the VL domain.

The variant antigen-binding domain of the invention may comprise mutations T28K, Y32F and A100N in the VH domain and further comprises at least one mutation selected from:

a) in the VH domain:
 V2K, V2R,
 Y27F, Y27M, Y27N, Y27W,
 G31K, G31R, G31S,
 R98K,
 Y102F, Y102L,
 N103A, N103E, N103F, N103H, N103L, N103M, N103Q, N103S, N103W, N103Y, and
 A107S, and
b) in the VL domain:
 N35M, N35F, N35Y, N35K, N35R, and
 R55K.

The variant antigen-binding domain of the invention may be selected from a variant antigen-binding domain comprising the following mutation combinations:

T28K, Y32F, A100N, Y27N in the VH domain,
T28K, Y32F, A100N, G31K in the VH domain,
T28K, Y32F, A100N, Y27M in the VH domain,
T28K, Y32F, A100N, Y27W in the VH domain,
T28K, Y32F, A100N in the VH domain,
T28K, Y32F, A100N in the VH domain and R55K in the VL domain,
T28K, Y32F, A100N in the VH domain and N35K in the VL domain,
T28K, Y32F, A100N, N103H in the VH domain,
T28K, Y32F, A100N, N103A in the VH domain,
T28K, Y32F, A100N, N103Y in the VH domain,
T28K, Y32F, A100N in the VH domain and N35R in the VL domain,
T28K, Y32F, A100N, N103S in the VH domain and N35M in the VL domain,
T28K, Y32F, A100N, N103M, in the VH domain,
T28K, Y32F, A100N, N103W in the VH domain and N35R in the VL domain,
T28K, Y32F, A100N in the VH domain and N35F in the VL domain,
T28K, Y32F, A100N, N103S in the VH domain and N35K in the VL domain,
T28K, Y32F, A100N, R98K in the VH domain,
T28K, Y32F, A100N, N103S in the VH domain and N35R in the VL domain,
T28K, Y32F, A100N, N103L in the VH domain,
T28K, Y32F, A100N, N103S in the VH domain and N35F in the VL domain,
T28K, Y32F, A100N, N103S in the VH domain and N35Y in the VL domain,
T28K, Y32F, A100N, N103L in the VH domain and N35M in the VL domain,
T28K, Y32F, A100N, N103L in the VH domain and N35R in the VL domain,
T28K, Y32F, A100N, N103W in the VH domain and N35K in the VL domain,
T28K, Y32F, A100N, N103L in the VH domain and N35Y in the VL domain,
T28K, Y32F, A100N, N103F in the VH domain,
T28K, Y32F, A100N, N103W in the VH domain, T28K, Y32F, A100N, N103L in the VH domain and N35K in the VL domain, T28K, Y32F, A100N, N103L in the VH domain and N35F in the VL domain, T28K, Y32F, A100N, N103W in the VH domain and N35M in the VL domain, T28K, Y32F, A100N, N103F in the VH domain and N35Y in the VL domain, T28K, Y32F, A100N, Y27F in the VH domain, T28K, Y32F, A100N, N103Q in the VH domain, T28K, Y32F, A100N, N103S in the VH domain, T28K, Y32F, A100N, N103M in the VH domain and N35F in the VL domain, T28K, Y32F, A100N, N103F in the VH domain and N35M in the VL domain, T28K, Y32F, A100N, N103F in the VH domain and N35F in the VL domain, T28K, Y32F, A100N, G31R in the VH domain, T28K, Y32F, A100N, N103W in the VH domain and N35F in the VL domain, T28K, Y32F, A100N, V2R in the VH domain, T28K, Y32F, A100N, G31S in the VH domain, T28K, Y32F, A100N, A107S in the VH domain, T28K, Y32F, A100N, N103E in the VH domain and N35M in the VL domain, T28K, Y32F, A100N, V2K in the VH domain, T28K, Y32F, A100N, N103E in the VH domain, T28K, Y32F, A100N, Y102F, N103M in the VH domain and N35K in the VL domain, T28K, Y32F, A100N, Y102F, N103M in the VH domain and N35F in the VL domain, T28K, Y32F, A100N, Y102F, N103M in the VH domain and N35R in the VL domain, T28K, Y32F, A100N, Y102F in the VH domain and N35R in the VL domain, T28K, Y32F, A100N, N103M in the VH domain and N35M in the VL domain, T28K, Y32F, A100N, N103M in the VH domain and N35Y in the VL domain, T28K, Y32F, A100N, N103M in the VH domain and N35R in the VL domain, T28K, Y32F, A100N, N103F in the VH domain and N35K in the VL domain, T28K, Y32F, A100N, Y102L, N103W in the VH domain and N35R in the VL domain, T28K, Y32F, A100N, Y102L, N103W in the VH domain and N35K in the VL domain, T28K, Y32F, A100N, Y102F in the VH domain, and T28K, Y32F, A100N, Y102L, N103M in the VH domain and N35R in the VL domain.

These specific combined mutations have been shown to alter binding to TRBC2 and TRBC1 in a manner which is useful to TRBC2 targeting (see Table 1).

TABLE 1

Affinities of variant antigen-binding domains of the invention for TRBC2 and TRBC1.

| KD TRBC1 (M) | Ratio KD TRBC2:KD TRBC1 | KD TRBC2 (M) | Mutation(s) in VH domain | Mutation(s) in VL domain |
|---|---|---|---|---|
| N/A | — | 2.61E−06 | T28K, Y32F, A100N, Y102F | — |
| N/A | — | 1.90E−06 | T28K, Y32F, A100N, Y102L, N103M | N35R |
| N/A | — | 1.72E−06 | T28K, Y32F, A100N, Y102L, N103W | N35K |
| N/A | — | 1.51E−06 | T28K, Y32F, A100N, Y102L, N103W | N35R |
| 2.93E−06 | 2.255778 | 1.30E−06 | T28K, Y32F, A100N, N103E | — |
| 3.14E−06 | 2.310066 | 1.36E−06 | G31R, Y32F, A100N | — |
| 1.44E−06 | 2.483233 | 5.82E−07 | T28R, Y32F, A100N | — |
| 2.40E−06 | 2.718831 | 8.83E−07 | V2K, T28K, Y32F, A100N | — |
| 5.83E−06 | 2.735336 | 2.13E−06 | N103E, T28K, Y32F, A100N | N35M |
| 8.81E−07 | 2.994222 | 2.94E−07 | T28K, Y32F, A100N, N103F | N35K |
| 3.59E−06 | 3.094047 | 1.16E−06 | T28K, Y32F, A100N, A107S | — |
| 3.68E−06 | 3.149100 | 1.17E−06 | G31S, T28K, Y32F, A100N | — |
| 5.11E−06 | 3.193125 | 1.60E−06 | V2R, T28K, Y32F, A100N | — |
| 2.902E−07 | 3.213376 | 9.031E−08 | T28K, Y32F, A100N, N103M | N35R |
| 1.68E−06 | 3.301942 | 5.10E−07 | N103W, T28K, Y32F, A100N | N35F |
| 1.74E−05 | 3.506467 | 4.95E−06 | T28K, G31R, Y32F, A100N | — |
| 1.61E−06 | 3.513396 | 4.59E−07 | N103F, T28K, Y32F, A100N | N35F |
| 4.59E−07 | 3.524942 | 1.30E−07 | N103F, T28K, Y32F, A100N | N35M |
| 4.59E−07 | 3.524942 | 1.30E−07 | N103M, T28K, Y32F, A100N | N35F |
| 3.54E−06 | 3.596054 | 9.83E−07 | T28K, Y32F, A100N, N103S | — |
| 1.77E−06 | 3.664737 | 4.84E−07 | T28K, Y32F, A100N, N103Q | — |
| 4.48E−06 | 3.690025 | 1.21E−06 | Y27F, T28K, Y32F, A100N | — |
| 1.86E−06 | 3.715825 | 5.01E−07 | N103F, T28K, Y32F, A100N | N35Y |
| 2.28E−06 | 3.733421 | 6.11E−07 | N103W, T28K, Y32F, A100N | N35M |
| 1.38E−06 | 3.743229 | 3.69E−07 | N103L, T28K, Y32F, A100N | N35F |
| 7.07E−07 | 3.775107 | 1.87E−07 | N103L, T28K, Y32F, A100N | N35K |
| 1.65E−06 | 3.884706 | 4.25E−07 | T28K, Y32F, A100N, N103W | — |
| 1.06E−06 | 3.920770 | 2.70E−07 | T28K, Y32F, A100N, N103F | — |
| 1.93E−06 | 4.012925 | 4.80E−07 | N103L, T28K, Y32F, A100N | N35Y |
| 1.68E−06 | 4.031175 | 4.17E−07 | N103W, T28K, Y32F, A100N | N35K |
| 8.10E−07 | 4.038404 | 2.01E−07 | N103L, T28K, Y32F, A100N | N35R |
| 1.50E−06 | 4.114898 | 3.64E−07 | N103L, T28K, Y32F, A100N | N35M |
| 7.83E−06 | 4.167642 | 1.88E−06 | N103S, T28K, Y32F, A100N | N35Y |
| 6.58E−06 | 4.227506 | 1.56E−06 | N103S, T28K, Y32F, A100N | N35F |
| 1.28E−06 | 4.227966 | 3.02E−07 | T28K, Y32F, A100N, N103L | — |
| 7.328E−07 | 4.248116 | 1.725E−07 | T28K, Y32F, A100N, N103M | N35Y |
| 3.93E−06 | 4.289299 | 9.17E−07 | N103S, T28K, Y32F, A100N | N35R |
| 4.66E−06 | 4.317593 | 1.08E−06 | T28K, Y32F, R98K, A100N | — |
| 3.68E−06 | 4.321147 | 8.51E−07 | N103S, T28K, Y32F, A100N | N35K |
| 2.81E−06 | 4.355638 | 6.46E−07 | T28K, Y32F, A100N | N35F |

TABLE 1-continued

Affinities of variant antigen-binding domains of the invention for TRBC2 and TRBC1.

| KD TRBC1 (M) | Ratio KD TRBC2:KD TRBC1 | KD TRBC2 (M) | Mutation(s) in VH domain | Mutation(s) in VL domain |
|---|---|---|---|---|
| 1.73E−06 | 4.428205 | 3.90E−07 | N103W, T28K, Y32F, A100N | N35R |
| 3.76E−07 | 4.498924 | 8.36E−08 | T28K, Y32F, A100N, N103M | — |
| 8.22E−06 | 4.503834 | 1.83E−06 | N103S, T28K, Y32F, A100N | N35M |
| 9.29E−07 | 4.596239 | 2.02E−07 | T28K, Y32F, A100N | N35R |
| 1.58E−06 | 4.655835 | 3.39E−07 | T28K, Y32F, A100N, N103Y | — |
| 3.39E−06 | 4.746499 | 7.14E−07 | T28K, Y32F, A100N, N103A | — |
| 2.02E−06 | 4.847246 | 4.16E−07 | T28K, Y32F, A100N, N103H | — |
| 6.48E−07 | 4.963247 | 1.31E−07 | T28K, Y32F, A100N, N103M | N35M |
| 1.00E−06 | 5.231892 | 1.92E−07 | T28K, Y32F, A100N | N35K |
| 9.62E−07 | 5.835558 | 1.65E−07 | T28K Y32F A100N | R55K |
| 2.73E−06 | 6.317740 | 4.32E−07 | T28K, Y32F, A100N | — |
| 2.10E−05 | 6.850702 | 3.06E−06 | Y27W, T28K, Y32F, A100N | — |
| 1.89E−05 | 6.973733 | 2.70E−06 | T28K, Y32F, A100N, Y102F | N35R |
| 7.91E−06 | 8.171210 | 9.68E−07 | T28K, Y32F, A100N, Y102F, N103M | N35R |
| 1.13E−05 | 8.580106 | 1.32E−06 | T28K, Y32F, A100N, Y102F, N103M | N35F |
| 1.81E−05 | 8.672100 | 2.09E−06 | Y27M, T28K, Y32F, A100N | — |
| 3.11E−05 | 9.620019 | 3.24E−06 | T28K, G31K, Y32F, A100N | — |
| 9.31E−06 | 10.244171 | 9.09E−07 | T28K, Y32F, A100N, Y102F, N103M | N35K |
| 7.43E−05 | 10.702664 | 6.95E−06 | Y27N, T28K, Y32F, A100N | — |

N/A: not available; binding to TRBC1 is practically zero and is out of the detection limits of the apparatus.

In a particular embodiment, the variant antigen-binding domain of the invention comprises T28K, Y32F, A100N mutations in the VH domain.

In another particular embodiment, the variant antigen-binding domain of the invention comprises T28K, Y32F, A100N, and Y27N mutations in the VH domain.

In another particular embodiment, the variant antigen-binding domain of the invention comprises T28K, Y32F, A100N, and N103M mutations in the VH domain.

In another particular embodiment, the variant antigen-binding domain of the invention comprises T28K, Y32F, A100N mutations in the VH domain and N35K in the VL domain.

In another particular embodiment, the variant antigen-binding domain of the invention comprises T28K, Y32F, A100N, N103L mutations in the VH domain.

In another particular embodiment, the variant antigen-binding domain of the invention comprises T28K, Y32F, A100N, N103M mutations in the VH domain and N35Y mutation in the VL domain.

In another particular embodiment, the variant antigen-binding domain of the invention comprises T28K, Y32F, A100N, Y102F, N103M mutations in the VH domain and N35R mutation in the VL domain.

In another particular embodiment, the variant antigen-binding domain of the invention comprises T28K, Y32F, A100N, Y102L, N103M mutations in the VH domain and N35R mutation in the VL domain.

It would be particularly advantageous that the variant antigen-binding domain of the invention not only displays an increased affinity for TRBC2 over the reference antibody, but also that its affinity for TRBC1 is decreased compared to that of the reference antibody. This change in antigen specificity would allow the variant antigen-binding domain to discriminate between TRBC2 and TRBC1 by showing preferential binding to TRBC2. Thus, in another embodiment, the variant antigen-binding domain further displays a decreased affinity for TRBC1 over the reference antibody.

The affinity of the variant antigen-binding domain of the invention for TRBC1 is decreased over that of the reference antibody. The affinity of the variant antigen-binding domain for TRBC2 may be increased in at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 150%, at least 200%, at least 300%, at least 400%, at least 500%, at least 600%, at least 700%, at least 800%, at least 900%, at least 1,000%, at least 5,000%, or at least 10,000% over the affinity of the reference antibody for TRBC1.

The ratio of the affinities of the variant antigen-binding domain of the invention for TRBC2 and for TRBC1 may be at least 2, or at least 3, or at least 4, or at least 5, or at least 6, or at least 7, or at least 8, or at least 9, or at least 10, or at least 15, or at least 20, or at least 25, or at least 50, or at least 100, or at least 500, or at least 1,000, or more.

By increasing the avidity of the variant-antigen binding domain of the invention in Example 6, the present inventors unexpectedly discovered that not only the avidity of the variant-antigen binding domain of the invention for TRBC2 was increased, but also that its low affinity for TRBC1 was maintained and, consequently, that the specificity of the variant-antigen binding domain of the invention for TRBC2 was dramatically improved.

The avidity of the variant-antigen binding domain of the invention for TRBC2 may be increased using a domain having the capacity to form oligomers or multimers. Thus, the variant-antigen binding domain of the invention may further comprise an oligomerisation domain. The term "oligomerisation domain", as used herein, refers to a domain that self-associates to form an oligomer, such as a dimer or trimer, or a multimer. Thus, as used herein, the term oligomerisation domain also refers to a multimerisation domain. Oligomerisation domains are well known to the skilled person and any oligomerisation domain may be used with the variant antigen-binding domain of the invention provided the resulting oligomer maintains or improves the affinity of the monomer variant antigen-binding domain for TRBC2. Examples of oligomerisation domains include, without limitation, the Fc region, COMP spacer of SEQ ID NO: 18 or a truncated COMP as described below in the context of the chimeric antigen receptor (CAR) of the invention.

The present invention also contemplates different formats for the variant antigen-binding domain of the invention including, without limitation, a scFv, diabody, trimerbody, minibody, F(ab) and $F(ab')_2$ fragments, and whole antibody, i.e. IgG, IgM, IgA, IgD, IgE.

Thus, another aspect of the invention relates to an antibody, hereinafter "the antibody of the invention", comprising a variant antigen-binding domain of the invention.

3. Chimeric Antigen Receptors

In another aspect, the present invention provides a chimeric antigen receptor (CAR), hereinafter "the CAR of the invention", comprising a variant antigen-binding domain of the invention, a transmembrane domain and an endodomain.

The term "variant antigen-binding domain of the invention" has been described in detail in the context of the first aspect of the invention and its features and embodiments apply equally to this aspect of the invention.

The term "chimeric antigen receptor" or "CAR" or "chimeric T cell receptor" or "artificial T cell receptors" or "chimeric immunoreceptors", as used herein, refers to a chimeric type I trans-membrane protein which connects an extracellular antigen-recognising domain (binder) to an intracellular signalling domain (endodomain). The binder is typically a single-chain variable fragment (scFv) derived from a monoclonal antibody (mAb), but it can be based on other formats which comprise an antigen binding site. A spacer domain is usually necessary to separate the binder from the membrane and to allow it a suitable orientation. A common spacer domain used is the Fc of IgG1. More compact spacers can suffice e.g. the stalk from CD8a and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 4-1BB which transmit survival signals. Even more potent third generation CARs have now been described which have endodomains capable of transmitting activation, proliferation and survival signals.

When the CAR binds the target-antigen, this results in the transmission of an activating signal to the T-cell it is expressed on. Thus the CAR directs the specificity and cytotoxicity of the T cell towards tumour cells expressing the targeted antigen.

CARs typically therefore comprise: (i) an antigen-binding domain; (ii) a spacer; (iii) a transmembrane domain; and (iii) an intracellular domain which comprises or associates with a signalling domain (see FIG. 4).

A CAR may have the general structure:

Antigen-binding domain—spacer domain—transmembrane domain—intracellular signalling domain (endodomain).

3.1. Signal Peptide

The CAR of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognised and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID NO: 3 to 5 or a variant thereof having 5, 4, 3, 2 or 1 amino acid mutations (insertions, substitutions or additions) provided that the signal peptide still functions to cause cell surface expression of the protein.

```
SEQ ID NO: 3:
MGTSLLCWMALCLLGADHADG
```

The signal peptide of SEQ ID NO: 3 is compact and highly efficient. It is predicted to give about 95% cleavage after the terminal glycine, giving efficient removal by signal peptidase.

```
SEQ ID NO: 4:
MSLPVTALLLPLALLLHAARP
```

The signal peptide of SEQ ID NO: 4 is derived from IgG1.

```
SEQ ID NO: 5:
MAVPTQVLGLLLLWLTDARC
```

The signal peptide of SEQ ID NO: 5 is derived from CD8.

3.2. Spacer Domain

CARs comprise a spacer sequence to connect the antigen-binding domain with the transmembrane domain and spatially separate the antigen-binding domain from the endodomain. A flexible spacer allows the antigen-binding domain to orient in different directions to facilitate binding.

In the CAR of the present invention, the spacer sequence may, for example, comprise an IgG1 Fc region, an IgG1 hinge or a human CD8 stalk or the mouse CD8 stalk. The spacer may alternatively comprise an alternative linker sequence which has similar length and/or domain spacing properties as an IgG1 Fc region, an IgG1 hinge or a CD8 stalk. A human IgG1 spacer may be altered to remove Fc binding motifs. The spacer may comprise a coiled-coil domain, for example as described in WO2016/151315.

The CAR of the present invention may comprise a sequence selected from the sequences shown as SEQ ID NOs: 6 to 10 or a variant thereof having at least 80% sequence identity.

```
(hinge-CH2CH3 of human IgG1)
                                    SEQ ID NO: 6
AEPKSPDKTHTCPPCPAPPVAGPSVFLFPPKPKDTLMIARTPEVTCVVVD
```

-continued

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKD (human CD8 stalk):

SEQ ID NO: 7

TTTPAPRPPTPAPTIASQPLSLRPEACRPAAGGAVHTRGLDFACDI (human IgG1 hinge):

SEQ ID NO: 8

AEPKSPDKTHTCPPCPKDPK (CD2 ectodomain)

SEQ ID NO: 9

KEITNALETWGALGQDINLDIPSFQMSDDIDDIKWEKTSDKKKIAQFRKE

KETFKEKDTYKLFKNGTLKIKHLKTDDQDIYKVSIYDTKGKNVLEKIFDL

KIQERVSKPKISWTCINTTLTCEVMNGTDPELNLYQDGKHLKLSQRVITH

KWTTSLSAKFKCTAGNKVSKESSVEPVSCP

EKGLD (CD34 ectodomain)

SEQ ID NO: 10

SLDNNGTATPELPTQGTFSNVSTNVSYQETTTPSTLGSTSLHPVSQHGNE

ATTNITETTVKFTSTSVITSVYGNTNSSVQSQTSVISTVFTTPANVSTPE

TTLKPSLSPGNVSDLSTTSTSLATSPTKPYTSSSPILSDIKAEIKCSGIR

EVKLTQGICLEQNKTSSCAEFKKDRGEGLARVLCGEEQADADAGAQVCSL

LLAQSEVRPQCLLLVLANRTEISSKLQLMKKHQSDLKKLGILDFTEQDVA

SHQSYSQKT (COMP)

SEQ ID NO: 19

DLGPQMLRELQETNAALQDVRELLRQQVREITFLKNTVMECDACG

It is possible to truncate the COMP coiled-coil domain at the N-terminus and retain surface expression. The coiled-coil COMP spacer may therefore comprise or consist of a truncated version of SEQ ID NO: 19, which is truncated at the N-terminus. The truncated COMP may comprise the 5 C-terminal amino acids of SEQ ID NO: 19, i.e. the sequence CDACG (SEQ ID NO: 20). The truncated COMP may comprise 5 to 44 amino acids, for example, at least 5, 10, 15, 20, 25, 30, 35 or 40 amino acids. The truncated COMP may correspond to the C-terminus of SEQ ID NO: 19. For example a truncated COMP comprising 20 amino acids may comprise the sequence QQVREITFLKNTVMECDACG (SEQ ID NO: 21). Truncated COMP may retain the cysteine residue(s) involved in multimerisation.

Truncated COMP may retain the capacity to form multimers.

3.3. Transmembrane Domain

The transmembrane domain is the sequence of the CAR that spans the membrane.

A transmembrane domain may be any protein structure which is thermodynamically stable in a membrane. This is typically an alpha helix comprising of several hydrophobic residues. The transmembrane domain of any transmembrane protein can be used to supply the transmembrane portion of the invention. The presence and span of a transmembrane domain of a protein can be determined by those skilled in the art using the TMHMM algorithm (http://www.cbs.dtu.dk/services/TMHMM-2.0/). Further, given that the transmembrane domain of a protein is a relatively simple structure, i.e. a polypeptide sequence predicted to form a hydrophobic alpha helix of sufficient length to span the membrane, an artificially designed TM domain may also be used (U.S. Pat. No. 7,052,906 B1 describes synthetic transmembrane components).

The transmembrane domain may be derived from CD28, CD8a or TYRP-1, which give good receptor stability.

In an embodiment, the transmembrane domain is derived from CD8a.

SEQ ID NO: 11: CD8a transmembrane domain
IYIWAPLAGTCGVLLLSLVIT

In another embodiment, the transmembrane domain is derived from TYRP-1.

SEQ ID NO: 12: TYRP-1 transmembrane domain
IIAIAVVGALLLVALIFGTASYLI 3.4. Endodomain The endodomain is the signal-transmission portion of the CAR. After antigen recognition, receptors cluster, native CD45 and CD148 are excluded from the synapse and a signal is transmitted to the cell. The most commonly used endodomain component is that of CD3t which contains 3 ITAMs. This transmits an activation signal to the T cell after antigen is bound. CD3t may not provide a fully competent activation signal and additional co-stimulatory signalling may be needed. Examples of co-stimulatory domains include the endodomains from CD28, OX40, 4-1BB, CD27, and ICOS, which can be used with CD3t to transmit a proliferative/survival signal.

In an embodiment, at least one co-stimulatory endodomain is used with CD3. In a particular embodiment, the co-stimulatory endodomain is selected from the group consisting of the endodomains from CD28, OX40, 4-1BB, CD27, and ICOS.

In another embodiment, at least two co-stimulatory endodomains are used with CD3. In a particular embodiment, the two co-stimulatory endodomain are selected from the group consisting of the endodomains from CD28, OX40, 4-1BB, CD27, and ICOS, in any combination and order. Particularly suitable combinations include the endodomains from CD28 and CD3, the endodomains of OX40 and CD3, the endodomains of 4-1BB and CD3, the endodomains from CD28, OX40 and CD3, and the endodomains from CD28, 4-1BB and CDK The transmembrane and intracellular T-cell signalling domain (endodomain) of a CAR with an activating endodomain may comprise the sequence shown as SEQ ID NO: 13 to 18 or a variant thereof having at least 80% sequence identity.

comprising CD28 transmembrane domain and CD3ζ endodomain

SEQ ID NO: 13

FWVLVVVGGVLACYSLLVTVAFIIFWVRRVKFSRSADAPAYQQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR comprising CD28 transmembrane domain and CD28 and CD3ζ endodomains

SEQ ID NO: 14

FWVLVVVGGVLACYSLLVTVAFIIFWVRSKRSRLLHSDYMNMTPRRPGPT

-continued

RKHYQPYAPPRDFAAYRSRVKFSRSADAPAYQQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPR comprising CD28 transmembrane domain and CD28, OX40 and CD3ζ endodomains

SEQ ID NO: 15

FWVLVVVGGVLACYSLLVTVAFIIFWVRSKRSRLLHSDYMNMTPRRPGPT

RKHYQPYAPPRDFAAYRSRDQRLPPDAHKPPGGGSFRTPIQEEQADAHST

LAKIRVKFSRSADAPAYQQGQNQLYNELNLGRREEYDVLDKRRGRDPEMG

GKPRRKNPQEGLYNELQKDKMAEAYSEIGMKGERRRGKGHDGLYQGLSTA

TKDTYDALHMQALPPR comprising CD8a transmembrane domain and CD3ζ endodomain

SEQ ID NO: 16

IYIWAPLAGTCGVLLLSLVITRVLYCKFSRSADAPAYQQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPR comprising CD8a transmembrane domain and 4-1BB and CD3ζ endodomains

SEQ ID NO: 17

IYIWAPLAGTCGVLLLSLVITLYCKRGRKKLLYIFKQPFMRPVQTTQEED

GCSCRFPEEEEGGCELRVKFSRSADAPAYQQGQNQLYNELNLGRREEYDV

LDKRRGRDPEMGGKPRRKNPQEGLYNELQKDKMAEAYSEIGMKGERRRGK

GHDGLYQGLSTATKDTYDALHMQALPPR comprising TYRP-1 transmembrane domain and 4-1BB and CD3ζ endodomains

SEQ ID NO: 18

IIAIAVVGALLLVALIFGTASYLIKRGRKKLLYIFKQPFMRPVQTTQEED

GCSCRFPEEEEGGCELRVKFSRSADAPAYQQGQNQLYNELNLGRREEYDV

LDKRRGRDPEMGGKPRRKNPQEGLYNELQKDKMAEAYSEIGMKGERRRGK

GHDGLYQGLSTATKDTYDALHMQALPPR

A variant sequence may have at least 80%, 85%, 90%, 95%, 98% or 99% sequence identity to SEQ ID NO: 13 to 18, provided that the sequence provides an effective transmembrane domain and an effective intracellular T cell signalling domain.

The CAR of the invention may comprise a sequence from the group of sequences shown as SEQ ID NO: 25 to 36.

SEQ ID NO: 25: CAR comprising T28K, Y32F, A100N mutations in the VH domain, N35K mutation in the VL domain, IgG1 hinge spacer, TYRP-1 transmembrane domain, and 4-1BB and CD3ζ endodomains

QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GYNFDGAYRFFDFWGQGTMVTVSSGGGGSGGGGSGGGGSDIVMTQSPLSL

PVTPGEPASISCRSSQRLVHSNGKTYLHWYLQKPGQSPRLLIYRVSNRFP

GVPDRFSGSGSGTDFTLKISRVEAEDVGVYYCSQSTHVPYTFGQGTKLEI

KRSDPAEPKSPDKTHTCPPCPKDPKIIAIAVVGALLLVALIFGTASYLIK

RGRKKLLYIFKQPFMRPVQTTQEEDGCSCRFPEEEEGGCELRRVKFSRSA

DAPAYQQGQNQLYNELNLGRREEYDVLDKRRGRDPEMGGKPRRKNPQEGL

-continued

YNELQKDKMAEAYSEIGMKGERRRGKGHDGLYQGLSTATKDTYDALHMQA

LPPR

SEQ ID NO: 26: CAR comprising T28K, Y32F, A100N mutations in the VH domain, IgG1 hinge spacer, TYRP-1 transmembrane domain, and 4-1BB and CD3ζ endodomains

QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GYNFDGAYRFFDFWGQGTMVTVSSGGGGSGGGGSGGGGSDIVMTQSPLSL

PVTPGEPASISCRSSQRLVHSNGNTYLHWYLQKPGQSPRLLIYRVSNRFP

GVPDRFSGSGSGTDFTLKISRVEAEDVGVYYCSQSTHVPYTFGQGTKLEI

KRSDPAEPKSPDKTHTCPPCPKDPKIIAIAVVGALLLVALIFGTASYLIK

RGRKKLLYIFKQPFMRPVQTTQEEDGCSCRFPEEEEGGCELRRVKFSRSA

DAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQA

LPPR

SEQ ID NO: 27: CAR comprising T28K, Y32F, A100N, N103L mutations in the VH domain, IgG1 hinge spacer, TYRP-1 transmembrane domain, and 4-1BB and CD3ζ endodomains

QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GYLFDGAYRFFDFWGQGTMVTVSSGGGGSGGGGSGGGGSDIVMTQSPLSL

PVTPGEPASISCRSSQRLVHSNGNTYLHWYLQKPGQSPRLLIYRVSNRFP

GVPDRFSGSGSGTDFTLKISRVEAEDVGVYYCSQSTHVPYTFGQGTKLEI

KRSDPAEPKSPDKTHTCPPCPKDPKIIAIAVVGALLLVALIFGTASYLIK

RGRKKLLYIFKQPFMRPVQTTQEEDGCSCRFPEEEEGGCELRRVKFSRSA

DAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQA

LPPR

SEQ ID NO: 28: CAR comprising T28K, Y32F, A100N, N103M mutations in the VH domain, N35Y mutation in the VL domain, IgG1 hinge spacer, TYRP-1 transmembrane domain, and 4-1BB and CD3ζ endodomains

QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GYMFDGAYRFFDFWGQGTMVTVSSGGGGSGGGGSGGGGSDIVMTQSPLSL

PVTPGEPASISCRSSQRLVHSNGYTYLHWYLQKPGQSPRLLIYRVSNRFP

GVPDRFSGSGSGTDFTLKISRVEAEDVGVYYCSQSTHVPYTFGQGTKLEI

KRSDPAEPKSPDKTHTCPPCPKDPKIIAIAVVGALLLVALIFGTASYLIK

RGRKKLLYIFKQPFMRPVQTTQEEDGCSCRFPEEEEGGCELRRVKFSRSA

DAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQA

LPPR

SEQ ID NO: 29: CAR comprising T28K, Y32F, A100N, N103M mutations in the VH domain, N35R mutation in the VL domain, IgG1 hinge spacer, TYRP-1 transmembrane domain, and 4-1BB and CD3ζ

-continued endodomains

QVQLVQSGAEVKKPGASVKVSCKASGYKFTGFVMHWVRQAPGQGLEWMGF
INPYNDDIQSNERFRGRVTMTRDTSISTAYMELSRLRSDDTAVYYCARGN
GFMFDGAYRFFDFWGQGTMVTVSSGGGGSGGGGSGGGGSDIVMTQSPLSL
PVTPGEPASISCRSSQRLVHSNGRTYLHWYLQKPGQSPRLLIYRVSNRFP
GVPDRFSGSGSGTDFTLKISRVEAEDVGVYYCSQSTHVPYTFGQGTKLEI
KRSDPAEPKSPDKTHTCPPCPKDPKIIAIAVVGALLLVALIFGTASYLIK
RGRKKLLYIFKQPFMRPVQTTQEEDGCSCRFPEEEEGGCELRRVKFSRSA
DAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQA
LPPR

SEQ ID NO: 30: CAR comprising T28K, Y32F, A100N, Y102L, N103M mutations in the VH domain, N35R mutation in the VL domain, IgG1 hinge spacer, TYRP-1 transmembrane domain, and 4-1BB and CD3ζ endodomains QVQLVQSGAEVKKPGASVKVSCKASGYKFTGFVMHWVRQAPGQGLEWMGF
INPYNDDIQSNERFRGRVTMTRDTSISTAYMELSRLRSDDTAVYYCARGN
GLMFDGAYRFFDFWGQGTMVTVSSGGGGSGGGGSGGGGSDIVMTQSPLSL
PVTPGEPASISCRSSQRLVHSNGRTYLHWYLQKPGQSPRLLIYRVSNRFP
GVPDRFSGSGSGTDFTLKISRVEAEDVGVYYCSQSTHVPYTFGQGTKLEI
KRSDPAEPKSPDKTHTCPPCPKDPKIIAIAVVGALLLVALIFGTASYLIK
RGRKKLLYIFKQPFMRPVQTTQEEDGCSCRFPEEEEGGCELRRVKFSRSA
DAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQA
LPPR SEQ ID NO: 31: CAR comprising T28K, Y32F, A100N mutations in the VH domain, CD8 stalk spacer, TYRP-1 transmembrane domain, and 4-1BB and CD3ζ endodomains QVQLVQSGAEVKKPGASVKVSCKASGYKFTGFVMHWVRQAPGQGLEWMGF
INPYNDDIQSNERFRGRVTMTRDTSISTAYMELSRLRSDDTAVYYCARGN
GYNFDGAYRFFDFWGQGTMVTVSSGGGGSGGGGSGGGGSDIVMTQSPLSL
PVTPGEPASISCRSSQRLVHSNGNTYLHWYLQKPGQSPRLLIYRVSNRFP
GVPDRFSGSGSGTDFTLKISRVEAEDVGVYYCSQSTHVPYTFGQGTKLEI
KRSDPTTTPAPRPPTPAPTIASQPLSLRPEACRPAAGGAVHTRGLDFACD
IIIAIAVVGALLLVALIFGTASYLIKRGRKKLLYIFKQPFMRPVQTTQEE
DGCSCRFPEEEEGGCELRRVKFSRSADAPAYQQGQNQLYNELNLGRREEY
DVLDKRRGRDPEMGGKPRRKNPQEGLYNELQKDKMAEAYSEIGMKGERRR
GKGHDGLYQGLSTATKDTYDALHMQALPPR SEQ ID NO: 32: CAR comprising T28K, Y32F, A100N mutations in the VH domain, CD8 stalk spacer, TYRP-1 transmembrane domain, and CD28 and CD3ζ endodomains QVQLVQSGAEVKKPGASVKVSCKASGYKFTGFVMHWVRQAPGQGLEWMGF
INPYNDDIQSNERFRGRVTMTRDTSISTAYMELSRLRSDDTAVYYCARGN
GYNFDGAYRFFDFWGQGTMVTVSSGGGGSGGGGSGGGGSDIVMTQSPLSL
PVTPGEPASISCRSSQRLVHSNGNTYLHWYLQKPGQSPRLLIYRVSNRFP
GVPDRFSGSGSGTDFTLKISRVEAEDVGVYYCSQSTHVPYTFGQGTKLEI
KRSDPTTTPAPRPPTPAPTIASQPLSLRPEACRPAAGGAVHTRGLDFACD
IIIAIAVVGALLLVALIFGTASYLIRSKRSRLLHSDYMNMTPRRPGPTRK
HYQPYAPPRDFAAYRSRRVKFSRSADAPAYQQGQNQLYNELNLGRREEYD
VLDKRRGRDPEMGGKPRRKNPQEGLYNELQKDKMAEAYSEIGMKGERRRG
KGHDGLYQGLSTATKDTYDALHMQALPPR SEQ ID NO: 33: CAR comprising T28K, Y32F, A100N mutations in the VH domain, IgG1 hinge spacer, TYRP-1 transmembrane domain, and CD28 and CD3ζ endodomains QVQLVQSGAEVKKPGASVKVSCKASGYKFTGFVMHWVRQAPGQGLEWMGF
INPYNDDIQSNERFRGRVTMTRDTSISTAYMELSRLRSDDTAVYYCARGN
GYNFDGAYRFFDFWGQGTMVTVSSGGGGSGGGGSGGGGSDIVMTQSPLSL
PVTPGEPASISCRSSQRLVHSNGNTYLHWYLQKPGQSPRLLIYRVSNRFP
GVPDRFSGSGSGTDFTLKISRVEAEDVGVYYCSQSTHVPYTFGQGTKLEI
KRSDPAEPKSPDKTHTCPPCPKDPKIIAIAVVGALLLVALIFGTASYLIR
SKRSRLLHSDYMNMTPRRPGPTRKHYQPYAPPRDFAAYRSRRVKFSRSAD
APAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQAL
PPR SEQ ID NO: 34: CAR comprising T28K, Y32F, A100N mutations in the VH domain, N35K mutation in the VL domain, IgG1 hinge spacer, TYRP-1 transmembrane domain, and CD28 and CD3ζ endodomains QVQLVQSGAEVKKPGASVKVSCKASGYKFTGFVMHWVRQAPGQGLEWMGF
INPYNDDIQSNERFRGRVTMTRDTSISTAYMELSRLRSDDTAVYYCARGN
GYNFDGAYRFFDFWGQGTMVTVSSGGGGSGGGGSGGGGSDIVMTQSPLSL
PVTPGEPASISCRSSQRLVHSNGKTYLHWYLQKPGQSPRLLIYRVSNRFP
GVPDRFSGSGSGTDFTLKISRVEAEDVGVYYCSQSTHVPYTFGQGTKLEI
KRSDPAEPKSPDKTHTCPPCPKDPKIIAIAVVGALLLVALIFGTASYLIR
SKRSRLLHSDYMNMTPRRPGPTRKHYQPYAPPRDFAAYRSRRVKFSRSAD
APAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQAL
PPR SEQ ID NO: 35: CAR comprising T28K, Y32F, A100N mutations in the VH domain, N35K mutation in the VL domain, CD8 stalk spacer, TYRP-1 transmembrane domain, and 4-1BB and CD3ζ endodomains QVQLVQSGAEVKKPGASVKVSCKASGYKFTGFVMHWVRQAPGQGLEWMGF
INPYNDDIQSNERFRGRVTMTRDTSISTAYMELSRLRSDDTAVYYCARGN
GYNFDGAYRFFDFWGQGTMVTVSSGGGGSGGGGSGGGGSDIVMTQSPLSL
PVTPGEPASISCRSSQRLVHSNGKTYLHWYLQKPGQSPRLLIYRVSNRFP
GVPDRFSGSGSGTDFTLKISRVEAEDVGVYYCSQSTHVPYTFGQGTKLEI
KRSDPTTTPAPRPPTPAPTIASQPLSLRPEACRPAAGGAVHTRGLDFACD
IIIAIAVVGALLLVALIFGTASYLIKRGRKKLLYIFKQPFMRPVQTTQEE
DGCSCRFPEEEEGGCELRRVKFSRSADAPAYQQGQNQLYNELNLGRREEY -continued

```
DVLDKRRGRDPEMGGKPRRKNPQEGLYNELQKDKMAEAYSEIGMKGERRR

GKGHDGLYQGLSTATKDTYDALHMQALPPR
```

SEQ ID NO: 36: CAR comprising T28K, Y32F, A100N mutations in the VH domain, N35K mutation in the VL domain, CD8 stalk spacer, TYRP-1 transmembrane domain, and CD28 and CD3ζ endodomains

```
QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GYNFDGAYRFFDFWGQGTMVTVSSGGGGSGGGGSGGGGSDIVMTQSPLSL

PVTPGEPASISCRSSQRLVHSNGKTYLHWYLQKPGQSPRLLIYRVSNRFP

GVPDRFSGSGSGTDFTLKISRVEAEDVGVYYCSQSTHVPYTFGQGTKLEI

KRSDPTTTPAPRPPTPAPTIASQPLSLRPEACRPAAGGAVHTRGLDFACD

IIIAIAVVGALLLVALIFGTASYLIRSKRSRLLHSDYMNMTPRRPGPTRK

HYQPYAPPRDFAAYRSRRVKFSRSADAPAYQQGQNQLYNELNLGRREEYD

VLDKRRGRDPEMGGKPRRKNPQEGLYNELQKDKMAEAYSEIGMKGERRRG

KGHDGLYQGLSTATKDTYDALHMQALPPR
```

4. Bispecific T-Cell Engager

A wide variety of molecules have been developed which are based on the basic concept of having two antibody-like binding domains.

Bispecific T-cell engaging molecules are a class of bispecific antibody-type molecules that have been developed, primarily for the use as anti-cancer drugs. They direct a host's immune system, more specifically the T cells' cytotoxic activity, against a target cell, such as a cancer cell. In these molecules, one binding domain binds to a T cell via the CD3 receptor, and the other to a target cells such as a tumour cell (via a tumour specific molecule). Since the bispecific molecule binds both the target cell and the T cell, it brings the target cell into proximity with the T cell, so that the T cell can exert its effect, for example, a cytotoxic effect on a cancer cell. The formation of the T cell:bispecific Ab:cancer cell complex induces signalling in the T cell leading to, for example, the release of cytotoxic mediators. Ideally, the agent only induces the desired signalling in the presence of the target cell, leading to selective killing.

Bispecific T-cell engaging molecules have been developed in a number of different formats, but one of the most common is a fusion consisting of two tandemly-arranged single-chain variable fragments (scFvs) of different antibodies. These are sometimes known as BiTEs (Bi-specific T-cell Engagers).

The present invention also contemplates a bi-specific molecule which selectively recognises TRBC2 and is capable of activating a T cell. For example, the molecule may be a BiTE.

Thus, in another aspect, the present invention provides a bispecific T-cell engager (BiTE), "hereinafter the BiTE of the invention", comprising a variant antigen-binding domain of the invention and a T-cell activation domain.

The term "variant antigen-binding domain of the invention" has been described in detail in the context of the first aspect of the invention and its features and embodiments apply equally to this aspect of the invention.

The term "T-cell activation domain", as used herein, refers to a second domain capable of activating a T cell. The T-cell activation domain may be a scFv that binds specifically to CD3. Examples of anti-CD3 scFv that are suitable for the purposes of the present invention are well known in the art and include, without limitation, the scFv derived from OKT3.

The bi-specific molecule may comprise a signal peptide to aid in its production. The signal peptide may cause the bi-specific molecule to be secreted by a host cell, such that the bi-specific molecule can be harvested from the host cell supernatant.

The signal peptide may be at the amino terminus of the molecule. The bi-specific molecule may have the general formula: Signal peptide—variant antigen-binding domain of the invention—T-cell activation domain.

The bi-specific molecule may comprise a spacer sequence to connect the variant antigen-binding domain of the invention and a T-cell activation domain and spatially separate the two domains.

The spacer sequence may, for example, comprise an IgG1 hinge or a CD8 stalk. The linker may alternatively comprise an alternative linker sequence which has similar length and/or domain spacing properties as an IgG1 hinge or a CD8 stalk.

5. Nucleic Acid

In another aspect, the present invention also provides a nucleic acid sequence encoding a variant antigen-binding domain of the invention, hereinafter "the first nucleic acid of the invention".

In another aspect, the present invention also provides a nucleic acid sequence encoding an antibody of the invention, hereinafter "the second nucleic acid of the invention".

In another aspect, the present invention also provides a nucleic acid sequence encoding CAR of the invention, hereinafter "the third nucleic acid of the invention".

In another aspect, the present invention also provides a nucleic acid sequence encoding a BiTE of the invention, hereinafter "the fourth nucleic acid of the invention".

The terms "variant antigen-binding domain of the invention", "antibody of the invention", and "BiTE of the invention" have been described in detail in the context of previous aspects of the invention and their features and embodiments apply equally to these aspects of the invention.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

The nucleic acid sequences and constructs of the invention may contain alternative codons in regions of sequence encoding the same or similar amino acid sequences, in order to avoid homologous recombination.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

6. Vector

The present invention also provides a vector, or kit of vectors, which comprises one or more nucleic acid sequence of the invention. Such a vector may be used to introduce the nucleic acid sequence into a host cell so that it expresses a variant antigen-binding molecule, or an antibody, or a CAR, or a BiTE of the invention.

The terms "variant antigen-binding domain of the invention", "antibody of the invention", and "BiTE of the invention" have been described in detail in the context of previous aspects of the invention and their features and embodiments apply equally to these aspects of the invention.

The vector may, for example, be a plasmid or a viral vector, such as a retroviral vector or a lentiviral vector, or a transposon-based vector or synthetic mRNA.

The vector may be capable of transfecting or transducing a cytolytic immune cell, such as a T cells or NK cell.

7. Cell

Another aspect of the present invention relates to a cell, hereinafter "the cell of the invention", which comprises a CAR of the invention.

The cell may comprise a nucleic acid or a vector of the present invention.

The terms "CAR of the invention", "nucleic acid of the invention", "vector of the invention" have been described in detail in the context of previous aspects of the invention and their features and embodiments apply equally to these aspects of the invention.

The cell may be a cytolytic immune cell, such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumour cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cell of the invention may be any of the cell types mentioned above. In an embodiment, the cell of the invention is a T cell. In another embodiment, the cell of the invention is an NK cell.

Cells according to this aspect of the invention may either be created ex vivo either from a patient's own peripheral blood ($1^{st}$ party), or in the setting of a haematopoietic stem cell transplant from donor peripheral blood ($2^{nd}$ party), or peripheral blood from an unconnected donor ($3^{rd}$ party).

Alternatively, cells according to this aspect of the invention may be derived from ex vivo differentiation of inducible progenitor cells or embryonic progenitor cells to cytolytic cells. Alternatively, an immortalised cytolytic cell line, such as a T or NK cell, which retains its lytic function and could act as a therapeutic may be used.

In all these embodiments, CAR-expressing cells are generated by introducing DNA or RNA coding for the chimeric polypeptide by one of many means including transduction with a viral vector, transfection with DNA or RNA.

The cell of the invention may be an ex vivo cell from a subject. The cell may be from a peripheral blood mononuclear cell (PBMC) sample. The cell, in particular, a cytolytic cell such as a T or NK cell, may be activated and/or expanded prior to being transduced with nucleic acid encoding the molecules providing the CAR of the invention, for example by treatment with an anti-CD3 monoclonal antibody.

The cell of the invention may be made by a method which comprises a step of transducing or transfecting a cell with a vector of the invention which comprises a nucleic acid sequence encoding the CAR.

The method for making a cell of the invention may further comprise a step of isolating the cell from a cell-containing sample from a subject or from other sources listed above, prior to the transduction or transfection step. Where the cell is a cytolytic cell, the sample is a cytolytic cell-containing sample from the subject.

The term "subject" or "individual", as used in the context of the present invention, refers to members of mammalian species, preferably a male or female human being of any age or race.

The cell of the invention may then be purified, for example, by selection on the basis of expression of the antigen-binding domain of the CAR.

8. Conjugate

The variant antigen-binding domain or the antibody of the invention may be a conjugate of the variant antigen-binding domain or the antibody, for example the conjugate may be a detectable entity or a chemotherapeutic entity.

The terms "variant antigen-binding domain of the invention" and "antibody of the invention" have been described in detail in the context of previous aspects of the invention and their features and embodiments apply equally to these aspects of the invention.

The detectable entity may be a fluorescent moiety, for example a fluorescent peptide. The term "fluorescent peptide", as used herein, refers to a polypeptide which, following excitation, emits light at a detectable wavelength. Examples of fluorescent proteins include, but are not limited to, fluorescein isothiocyanate (FITC), phycoerythrin (PE), allophycocyanin (APC), green fluorescent protein (GFP), enhanced GFP, red fluorescent protein (RFP), blue fluorescent protein (BFP) and mCherry.

A variant antigen-binding domain or antibody of the invention conjugated to a detectable entity may be used to determine the TRBC of a malignant T cell.

The term "chemotherapeutic entity", as used herein, refers to an entity which is destructive to a cell, that is the entity reduces the viability of the cell. The resulting conjugates is hereinafter referred to as "the chemotherapeutic conjugate of the invention". The chemotherapeutic entity may be a cytotoxic drug. A chemotherapeutic entity contemplated includes, without limitation, alkylating agents, nitrosoureas, ethylenimines/methylmelamine, alkyl sulfonates, antimetabolites, pyrimidine analogues, epipodophylotoxins, enzymes such as L-asparaginase; biological response modifiers such as IFNα, IL-2, G-CSF and GM-CSF; platinium coordination complexes such as cisplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogues and leuprolide; and non-steroidal antiandrogens such as flutamide.

A variant antigen-biding domain or antibody of the invention conjugated to a chemotherapeutic entity enables the targeted delivery of the chemotherapeutic entity to cells which express TRBC2.

9. Pharmaceutical Composition

The present invention also relates to a pharmaceutical composition containing a cell or a plurality of cells, or an antibody, or a BiTE, or a chemotherapeutic conjugate of the invention, hereinafter "the pharmaceutical composition of the invention".

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

The terms "cell of the invention", "antibody of the invention", "BiTE of the invention", and "chemotherapeutic conjugate of the invention" have been described in detail in the context of previous aspects of the invention and their features and embodiments apply equally to these aspects of the invention.

Administration

The administration of the a cell or a plurality of cells, or an antibody, or a BiTE, or a chemotherapeutic conjugate of the invention can be accomplished using any of a variety of routes that make the active ingredient bioavailable. For example, the agent can be administered by oral and parenteral routes, intraperitoneally, intravenously, subcutaneously, transcutaneously, intramuscularly, via local delivery for example by catheter or stent.

Typically, a physician will determine the actual dosage which will be most suitable for an individual subject and it will vary with the age, weight and response of the particular patient. The dosage is such that it is sufficient to reduce or deplete the number of clonal T-cells expressing either TRBC1 or TRBC2.

10. Method of Treatment

In another aspect, the present invention provides a cell, or an antibody, or a BiTE, or a chemotherapeutic conjugate of the invention for use in medicine.

In another aspect, the present invention provides a method for treating a T-cell lymphoma or leukaemia in a subject, hereinafter "the method of treatment of the invention", which comprises the step of administering a cell, or an antibody, or a BiTE, or a chemotherapeutic conjugate of the invention to a subject, wherein the malignant T-cells express TRBC2. The administration step may be in the form of a pharmaceutical composition as described above.

This aspect of the invention may be alternatively formulated as a cell, or an antibody, or a BiTE, or a chemotherapeutic conjugate of the invention for use in the treatment of a T-cell lymphoma or leukaemia, hereinafter "the cell, antibody, BiTE, or chemotherapeutic conjugate for use of the invention", wherein the malignant T-cells express TRBC2.

This aspect of the invention may be alternatively formulated as the use of a cell, or an antibody, or a BiTE, or a chemotherapeutic conjugate of the invention in the manufacture of a medicament for treating a T-cell lymphoma or leukaemia, wherein the malignant T-cells express TRBC2.

The terms "cell of the invention", "antibody of the invention", "BiTE of the invention", "subject", and "chemotherapeutic conjugate of the invention" have been described in detail in the context of previous aspects of the invention and their features and embodiments apply equally to these aspects of the invention.

A method for treating a T-cell lymphoma and/or leukaemia relates to the therapeutic use of the cell, antibody, BiTE, or chemotherapeutic conjugate of the invention. Herein the cell, antibody, BiTE, or chemotherapeutic conjugate of the invention may be administered to a subject having an existing T-cell lymphoma and/or leukaemia in order to lessen, reduce or improve at least one symptom associated with the disease and/or to slow down, reduce or block the progression of the disease.

The method for preventing a T-cell lymphoma and/or leukaemia relates to the prophylactic use of the cell, antibody, BiTE, or chemotherapeutic conjugate of the present invention. Herein such cell, antibody, BiTE, or chemotherapeutic conjugate may be administered to a subject who has not yet contracted the T-cell lymphoma and/or leukaemia and/or who is not showing any symptoms of the T-cell lymphoma and/or leukaemia to prevent or impair the cause of the disease or to reduce or prevent development of at least one symptom associated with the disease. The subject may have a predisposition for, or be thought to be at risk of developing, the T-cell lymphoma and/or leukaemia.

The method may involve the steps of:

(i) isolating a cytotoxic cell-containing sample;

(ii) transducing or transfecting such cell with a nucleic acid sequence or vector provided by the present invention; and (iii) administering the cell from (ii) to a subject.

The cytotoxic cell-containing sample may be isolated from the subject or from other sources, for example as described above. The cytotoxic cell, such as a T or NK may be isolated from a subject's own peripheral blood ($1^{st}$ party), or in the setting of a haematopoietic stem cell transplant from donor peripheral blood ($2^{nd}$ party), or peripheral blood from an unconnected donor ($3^{rd}$ party).

A method for treating a T-cell lymphoma and/or leukaemia relates to the therapeutic use of an agent. Herein the agent may be administered to a subject having an existing disease of T-cell lymphoma and/or leukaemia in order to lessen, reduce or improve at least one symptom associated with the disease and/or to slow down, reduce or block the progression of the disease.

These therapeutic applications will comprise the administration of a therapeutically effective amount of the cell, antibody, BiTE, or chemotherapeutic conjugate of the present invention.

The term "therapeutically effective amount", as used herein, refers to the amount of the cell, antibody, BiTE, or chemotherapeutic conjugate of the present invention which is required to achieve an appreciable prevention, cure, delay, reduction of the severity of, or amelioration of one or more symptoms of a TRBC2 positive T-cell lymphoma and/or leukaemia.

The method of the present invention may be used for the treatment of any lymphoma and/or leukaemia associated with the clonal expansion of a cell expressing a T-cell receptor (TCR) comprising TRBC2. As such the present invention relates to a method for treating a disease which involves malignant T cells which express a TCR comprising a TRBC2.

The method of the present invention may be used to treat a T-cell lymphoma in which the malignant T-cell expresses a TCR comprising a TRBC2. "Lymphoma" is used herein according to its standard meaning to refer to a cancer which typically develops in the lymph nodes, but may also affect the spleen, bone marrow, blood and other organs.

Lymphoma typically presents as a solid tumour of lymphoid cells. The primary symptom associated with lymphoma is lymphadenopathy, although secondary (B) symptoms can include fever, night sweats, weight loss, loss of appetite, fatigue, respiratory distress and itching.

The method of the present invention may be used to treat a T-cell leukaemia in which the malignant T-cell expresses a TCR comprising a TRBC2. "Leukaemia" is used herein according to its standard meaning to refer to a cancer of the blood or bone marrow.

The following is an illustrative, non-exhaustive list of diseases which may be treated by the method of the present invention.

Peripheral T-Cell Lymphoma

Peripheral T-cell lymphomas are relatively uncommon lymphomas and account fewer than 10% of all non-Hodgkin lymphomas (NHL). However, they are associated with an aggressive clinical course and the causes and precise cellular origins of most T-cell lymphomas are still not well defined.

Lymphoma usually first presents as swelling in the neck, underarm or groin. Additional swelling may occur where other lymph nodes are located such as in the spleen. In general, enlarged lymph nodes can encroach on the space of blood vessels, nerves, or the stomach, leading to swollen arms and legs, to tingling and numbness, or to feelings of being full, respectively. Lymphoma symptoms also include nonspecific symptoms such as fever, chills, unexplained weight loss, night sweats, lethargy, and itching.

The WHO classification utilizes morphologic and immunophenotypic features in conjunction with clinical aspects and in some instances genetics to delineate a prognostically and therapeutically meaningful categorization for peripheral T-cell lymphomas (Swerdlow et al.; WHO classification of tumours of haematopoietic and lymphoid tissues. 4th ed.; Lyon: IARC Press; 2008). The anatomic localization of neoplastic T-cells parallels in part their proposed normal cellular counterparts and functions and as such T-cell lymphomas are associated with lymph nodes and peripheral blood. This approach allows for better understanding of some of the manifestations of the T-cell lymphomas, including their cellular distribution, some aspects of morphology and even associated clinical findings.

The most common of the T-cell lymphomas is peripheral T-cell lymphoma, not otherwise specified (PTCL-NOS) comprising 25% overall, followed by angioimmunoblastic T-cell lymphoma (AITL) (18.5%)

Peripheral T-Cell Lymphoma, not Otherwise Specified (PTCL-NOS)

PTCL-NOS comprises over 25% of all peripheral T-cell lymphomas and NK/T-cell lymphomas and is the most common subtype. It is determined by a diagnosis of exclusion, not corresponding to any of the specific mature T-cell lymphoma entities listed in the current WHO 2008. As such it is analogous to diffuse large B-cell lymphoma, not otherwise specified (DLBCL-NOS).

Most patients are adults with a median age of 60 and a male to female ratio 2:1. The majority of cases are nodal in origin, however, extranodal presentations occur in approximately 13% of patients and most commonly involve skin and gastrointestinal tract.

The cytologic spectrum is very broad, ranging from polymorphous to monomorphous. Three morphologically defined variants have been described, including lymphoepithelioid (Lennert) variant, T-zone variant and follicular variant. The lymphoepithelioid variant of PTCL contains abundant background epithelioid histiocytes and is commonly positive for CD8. It has been associated with a better prognosis. The follicular variant of PTCL-NOS is emerging as a potentially distinct clinicopathologic entity.

The majority of PTCL-NOS have a mature T-cell phenotype and most cases are CD4-positive. 75% of cases show variable loss of at least one pan T-cell marker (CD3, CD2, CD5 or CD7), with CD7 and CD5 being most often down-regulated. CD30 and rarely CD15 can be expressed, with CD15 being an adverse prognostic feature. CD56 expression, although uncommon, also has negative prognostic impact. Additional adverse pathologic prognostic factors include a proliferation rate greater than 25% based on KI-67 expression, and presence of more than 70% transformed cells. Immunophenotypic analysis of these lymphomas has offered little insight into their biology.

Angioimmunoblastic T-Cell Lymphoma (AITL)

AITL is a systemic disease characterised by a polymorphous infiltrate involving lymph nodes, prominent high endothelial venules (HEV) and peri-vascular expansion of follicular dendritic cell (FDC) meshworks. AITL is considered as a de-novo T-cell lymphoma derived from αβ T-cells of follicular helper type (TFH), normally found in the germinal centres.

AITL is the second most common entity among peripheral T-cell lymphoma and NK/T-cell lymphomas, comprising about 18.5% of cases. It occurs in middle aged to elderly adults, with a median age of 65 years old, and an approximately equal incidence in males and females. Clinically, patients usually have advanced stage disease, with generalised lymphadenopathy, hepatosplenomegaly and prominent constitutional symptoms. Skin rash with associated pruritus is commonly present. There is often polyclonal hypergammaglobulinemia, associated with autoimmune phenomena.

Three different morphologic patterns are described in AITL. The early lesion of AITL (Pattern I) usually shows preserved architecture with characteristic hyperplastic follicles. The neoplastic proliferation is localised to the periphery of the follicles. In Pattern II the nodal architecture is partially effaced with retention of few regressed follicles. The subcapsular sinuses are preserved and even dilated. The paracortex contains arborizing HEV and there is a proliferation of FDC beyond the B-cell follicle. The neoplastic cells are small to medium in size, with minimal cytologic atypia. They often have clear to pale cytoplasm, and may show distincT-cell membranes. A polymorphous inflammatory background is usually evident.

Although AITL is a T-cell malignancy, there is a characteristic expansion of B-cells and plasma cells, which likely reflects the function of the neoplastic cells as TFH cells. Both EBV-positive and EBV-negative B-cells are present. Occasionally, the atypical B-cells may resemble Hodgkin/Reed-Sternberg-like cells morphologically and immunophenotypically, sometimes leading to a diagnostic confusion with that entity. The B-cell proliferation in AITL may be extensive and some patients develop secondary EBV-positive diffuse large B-cell lymphomas (DLBCL) or—more rarely—EBV-negative B-cell tumors, often with plasmacytic differentiation.

The neoplastic CD4-positive T-cells of AITL show strong expression of CD10 and CD279 (PD-1) and are positive for CXCL13. CXCL13 leads to an increased B-cell recruitment to lymph nodes via adherence to the HEV, B-cell activation, plasmacytic differentiation and expansion of the FDC meshworks, all contributing to the morphologic and clinical features of AITL. Intense PD-1-expression in the perifollicular tumor cells is particularly helpful in distinguishing AITL Pattern I from reactive follicular and paracortical hyperplasia.

The follicular variant of PTCL-NOS is another entity with a TFH phenotype. In contradistinction to AITL, it does not have prominent HEV or extra-follicular expansion of FDC meshworks. The neoplastic cells may form intrafollicular aggregates, mimicking B-cell follicular lymphoma, but also can have interfollicular growth pattern or involve expanded mantle zones. Clinically, the follicular variant of PTCL-NOS is distinct from AITL as patients more often present with early stage disease with partial lymph node involvement and may lack the constitutional symptoms associated with AITL.

Anaplastic Large Cell Lymphoma (ALCL)

ALCL may be subdivided as ALCL-anaplastic lymphoma kinase (ALK)+ or ALCL-ALK−.

ALCL-ALK+ is one of the best-defined entities within the peripheral T-cell lymphomas, with characteristic "hallmark cells" bearing horseshoe-shaped nuclei and expressing ALK and CD30. It accounts for about 7% of all peripheral T-cell and NK-cell lymphomas and is most common in the first three decades of life. Patients often present with lymphadenopathy, but the involvement of extranodal sites (skin, bone, soft tissues, lung, liver) and B symptoms is common.

ALCL, ALK+ shows a wide morphologic spectrum, with 5 different patterns described, but all variants contain some hallmark cells. Hallmark cells have eccentric horseshoe- or kidney-shaped nuclei, and a prominent perinuclear eosinophilic Golgi region. The tumour cells grow in a cohesive pattern with predilection for sinus involvement. Smaller tumour cells predominate in the small cell variant, and in the lymphohistiocytic variant abundant histiocytes mask the presence of tumour cells, many of which are small.

By definition, all cases show ALK and CD30 positivity, with expression usually weaker in the smaller tumour cells. There is often loss of pan-T-cell markers, with 75% of cases lacking surface expression of CD3.

ALK expression is a result of a characteristic recurrent genetic alteration consisting of a rearrangement of ALK gene on chromosome 2p23 to one of the many partner genes, resulting in an expression of chimeric protein. The most common partner gene, occurring in 75% of cases, is Nucleophosmin (NPM1) on chromosome 5q35, resulting in t(2;5)(p23;q35). The cellular distribution of ALK in different translocation variants may vary depending on the partner gene.

ALCL-ALK− is included as a provisional category in the 2008 WHO classification. It is defined as a CD30 positive T-cell lymphoma that is morphologically indistinguishable from ALCL-ALK+ with a cohesive growth pattern and presence of hallmark cells, but lacking ALK protein expression.

Patients are usually adults between the ages of 40 and 65, in contrast to ALCL-ALK+, which is more common in children and young adults. ALCL-ALK− can involve both lymph nodes and extranodal tissues, although the latter is seen less commonly than in ALCL-ALK+. Most cases of ALCL-ALK− demonstrate effacement of lymph node architecture by sheets of cohesive neoplastic cells with typical "hallmark" features. In contrast to the ALCL-ALK+, the small cell morphologic variant is not recognised.

Unlike its ALK+ counterpart, ALCL-ALK− shows a greater preservation of surface T-cell marker expression, while the expression of cytotoxic markers and epithelial membrane antigen (EMA) is less likely. Gene expression signatures and recurrent chromosomal imbalances are different in ALCL-ALK− and ALCL-ALK+, confirming that they are distinct entities at a molecular and genetic level.

ALCL-ALK− is clinically distinct from both ALCL-ALK+ and PTCL-NOS, with significant differences in prognosis among these three different entities. The 5 year overall survival of ALCL-ALK− is reported as 49% which is not as good as that of ALCL-ALK+(at 70%), but at the same time it is significantly better than that of PTCL-NOS (32%).

Enteropathy-Associated T-Cell Lymphoma (EATL)

EATL is an aggressive neoplasm which thought to be derived from the intraepithelial T-cells of the intestine. Two morphologically, immunohistochemically and genetically distinct types of EATL are recognised in the 2008 WHO classification: Type I (representing the majority of EATL) and Type II (comprising 10-20% of cases).

Type I EATL is usually associated with overt or clinically silent gluten-sensitive enteropathy, and is more often seen in patients of Northern European extraction due to high prevalence of celiac disease in this population.

Most commonly, the lesions of EATL are found in the jejunum or ileum (90% of cases), with rare presentations in duodenum, colon, stomach, or areas outside of the gastrointestinal tract. The intestinal lesions are usually multifocal with mucosal ulceration. Clinical course of EATL is aggressive with most patients dying of disease or complications of disease within 1 year.

The cytological spectrum of EATL type I is broad, and some cases may contain anaplastic cells. There is a polymorphous inflammatory background, which may obscure the neoplastic component in some cases. The intestinal mucosa in regions adjacent to the tumour often shows features of celiac disease with blunting of the villi and increased numbers of intraepithelial lymphocytes (IEL), which may represent lesional precursor cells.

By immunohistochemistry, the neoplastic cells are often CD3+CD4−CD8−CD7+CD5−CD56−βF1+, and contain cytotoxic granule-associated proteins (TIA-1, granzyme B, perforin). CD30 is partially expressed in almost all cases. CD103, which is a mucosal homing receptor, can be expressed in EATL.

Type II EATL, also referred to as monomorphic CD56+ intestinal T-cell lymphoma, is defined as an intestinal tumour composed of small- to medium-sized monomorphic T-cells that express both CD8 and CD56. There is often a lateral spread of tumour within the mucosa, and absence of an inflammatory background. The majority of cases express the γδ TCR, however there are cases associated with the αβ TCR.

Type II EATL has a more world-wide distribution than Type I EATL and is often seen in Asians or Hispanic populations, in whom celiac disease is rare. In individuals of European descent EATL, II represents about 20% of intestinal T-cell lymphomas, with a history of celiac disease in at least a subset of cases. The clinical course is aggressive.

Hepatosplenic T-Cell Lymphoma (HSTL)

HSTL is an aggressive systemic neoplasm generally derived from γδ cytotoxic T-cells of the innate immune system, however, it may also be derived from αβ T-cells in rare cases. It is one of the rarest T-cell lymphomas, and typically affects adolescents and young adults (median age, 35 years) with a strong male predominance.

Extranodal NK/T-Cell Lymphoma Nasal Type

Extranodal NK/T-cell lymphoma, nasal type, is an aggressive disease, often with destructive midline lesions and necrosis. Most cases are of NK-cell derivation, but some cases are derived from cytotoxic T-cells. It is universally associated with Epstein-Barr Virus (EBV).

Cutaneous T-Cell Lymphoma

The method of the present invention may also be used to treat cutaneous T-cell lymphoma.

Cutaneous T-cell lymphoma (CTCL) is characterised by migration of malignant T-cells to the skin, which causes various lesions to appear. These lesions change shape as the disease progresses, typically beginning as what appears to be a rash and eventually forming plaques and tumours before metastasizing to other parts of the body.

Cutaneous T-cell lymphomas include those mentioned in the following illustrative, non-exhaustive list; mycosis fungoides, pagetoid reticulosis, Sézary syndrome, granulomatous slack skin, lymphomatoid papulosis, *pityriasis* lichenoides chronica, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma and angiocentric lymphoma.

The signs and symptoms of CTCL vary depending on the specific disease, of which the two most common types are mycosis fungoides and Sézary syndrome. Classic mycosis fungoides is divided into three stages:

Patch (atrophic or nonatrophic): Nonspecific dermatitis, patches on lower trunk and buttocks; minimal/absent pruritus;

Plaque: Intensely pruritic plaques, lymphadenopathy; and

Tumor: Prone to ulceration

Sézary syndrome is defined by erythroderma and leukemia. Signs and symptoms include edematous skin, lymphadenopathy, palmar and/or plantar hyperkeratosis, alopecia, nail dystrophy, ectropion and hepatosplenomegaly.

Of all primary cutaneous lymphomas, 65% are of the T-cell type. The most common immunophenotype is CD4 positive. There is no common pathophysiology for these diseases, as the term cutaneous T-cell lymphoma encompasses a wide variety of disorders.

The primary etiologic mechanisms for the development of cutaneous T-cell lymphoma (ie, mycosis fungoides) have not been elucidated. Mycosis fungoides may be preceded by a T-cell-mediated chronic inflammatory skin disease, which may occasionally progress to a fatal lymphoma.

Primary Cutaneous ALCL (C-ALCL)

C-ALCL is often indistinguishable from ALC-ALK− by morphology. It is defined as a cutaneous tumour of large cells with anaplastic, pleomorphic or immunoblastic morphology with more than 75% of cells expressing CD30. Together with lymphomatoid papulosis (LyP), C-ALCL belongs to the spectrum of primary cutaneous CD30-positive T-cell lymphoproliferative disorders, which as a group comprise the second most common group of cutaneous T-cell lymphoproliferations after mycosis fungoides.

The immunohistochemical staining profile is quite similar to ALCL-ALK−, with a greater proportion of cases staining positive for cytotoxic markers. At least 75% of the tumour cells should be positive for CD30. CD15 may also be expressed, and when lymph node involvement occurs, the differential with classical Hodgkin lymphoma can be difficult.

Rare cases of ALCL-ALK+ may present with localised cutaneous lesions, and may resemble C-ALCL.

T-Cell Acute Lymphoblastic Leukaemia

T-cell acute lymphoblastic leukaemia (T-ALL) accounts for about 15% and 25% of ALL in paediatric and adult cohorts respectively. Patients usually have high white blood cell counts and may present with organomegaly, particularly mediastinal enlargement and CNS involvement.

The method of the present invention may be used to treat T-ALL which is associated with a malignant T cell which expresses a TCR comprising a TRBC.

T-Cell Prolymphocytic Leukaemia

T-cell-prolymphocytic leukemia (T-PLL) is a mature T-cell leukaemia with aggressive behaviour and predilection for blood, bone marrow, lymph nodes, liver, spleen, and skin involvement. T-PLL primarily affects adults over the age of 30. Other names include T-cell chronic lymphocytic leukaemia, "knobby" type of T-cell leukaemia, and T-prolymphocytic leukaemia/T-cell lymphocytic leukaemia.

In the peripheral blood, T-PLL consists of medium-sized lymphocytes with single nucleoli and basophilic cytoplasm with occasional blebs or projections. The nuclei are usually round to oval in shape, with occasional patients having cells with a more irregular nuclear outline that is similar to the cerebriform nuclear shape seen in Sézary syndrome. A small cell variant comprises 20% of all T-PLL cases, and the Sézary cell-like (cerebriform) variant is seen in 5% of cases.

T-PLL has the immunophenotype of a mature (post-thymic) T-lymphocyte, and the neoplastic cells are typically positive for pan-T antigens CD2, CD3, and CD7 and negative for TdT and CD1a. The immunophenotype CD4+/CD8− is present in 60% of cases, the CD4+/CD8+ immunophenotype is present in 25%, and the CD4−/CD8+ immunophenotype is present in 15% of cases The T-cell lymphoma or leukaemia to be treated or prevented may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

The method of treatment may comprise a step of administering a therapeutic amount of a cell or a plurality of cells, or an antibody, or a BiTE, or a chemotherapeutic conjugate of the invention. The skilled person will be able to determine the amount of a cell or a plurality of cells, or an antibody, or a BiTE, or a chemotherapeutic conjugate of the invention that are able to exert a therapeutic effect on the patient by conventional methods.

11. Diagnostic Agent

It has been previously determined that the proportion of T cells from healthy donors that are $TRBC1^+$ versus $TRBC2^+$ is 35% vs. 65%, i.e. the median percentage of total T cells expressing TRBC1 was 35% (range, 25-47%) (Maciocia et al., 2017, Nat Med 23:1416-23). Since the T-cell lymphomas or leukaemias are clonal cancers (Maciocia et al., 2017; as above), the deregulated proliferation of malignant T cells characteristic of a T-cell lymphoma or leukaemia will result in a proportion of either $TRBC1^+$ or $TRBC2^+$ T-cells (i.e. $TRBC2^-$ or $TRBC1^-$ T-cells) that is significantly skewed. Accordingly, by binding specifically to TRBC2 and thus being capable of discriminating between TRBC1 and TRBC2, the variant antigen-binding domain and the antibody of the invention constitute useful agents for the diagnosis of T-cell lymphomas or leukaemias.

Thus, in another aspect, the present invention provides a diagnostic agent, hereinafter "the first diagnostic agent of the invention", which comprises a variant antigen-binding domain of the invention.

In another aspect, the present invention provides a diagnostic agent, hereinafter "the second diagnostic agent of the invention", which comprises an antibody of the invention. The terms "variant antigen-binding domain of the invention" and "antibody of the invention" have been described in detail in the context of previous aspects of the invention and their features and embodiments apply equally to these aspects of the invention.

The variant antigen-binding domain or antibody of the invention to be used in these assays can be labelled or unlabelled. The term "detectable label" or "labelling agent", as used herein, refers to a molecular label which allows the detection, localisation and/or identification of the molecule to which it is attached, using suitable procedures and equipment for detection, for example by spectroscopic, photochemical, biochemical, immunochemical or chemical means. Labelling agents that are suitable for labelling the antibodies include radionuclides, enzymes, fluorophores, chemiluminescent reagents, enzyme substrates or cofactors, enzyme inhibitors, particles, dyes and derivatives, and the like. As the person skilled in the art will appreciate, variant antigen-binding domains and antibodies that are not labelled need to be detected with an additional reagent, for example, a secondary antibody that is labelled. This is particularly useful in order to increase the sensibility of the detection method, since it allows the signal to be amplified. There is a wide range of conventional assays that can be used in the present invention which use an antibody of the invention that is not labelled (primary antibody) and an antibody of the invention that is labelled (secondary antibody); these techniques include Western blotting or immunoblot, ELISA (Enzyme-Linked Immunosorbent Assay), MA (Radioimmunoassay), competitive EIA (Competitive Enzyme Immunoassay), DAS-ELISA (Double Antibody Sandwich-ELISA), immunocytochemical and immunohistochemical techniques, flow cytometry or multiplex detection techniques based on using protein microspheres, biochips or microarrays which include the antibody of the invention. Other ways of detecting and quantifying TRBC2 using the variant antigen-binding domain or antibody of the invention include affinity chromatography techniques or ligand binding assays.

The diagnostic agent may be used for diagnosing a T-cell lymphoma or leukaemia.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

12. Method of Diagnosis

In another aspect, the present invention provides a method for diagnosing a T-cell lymphoma or leukaemia in a subject, hereinafter "the diagnostic method of the invention", which comprises the step of contacting a variant antigen-binding domain or an antibody of the invention to a sample comprising T-cells from the subject.

The terms "variant antigen-binding domain of the invention", "antibody of the invention", and "subject" have been described in detail in the context of previous aspects of the invention and their features and embodiments apply equally to this aspect of the invention.

The diagnostic method of the invention may further comprise a step of determining the percentage of TRBC2 positive T-cells in the sample.

To put the first method of the invention into practice, a sample comprising T-cells, such as a biological sample, is obtained from the subject to be studied. The term "sample" or "biological sample", as used herein, includes different types of biological fluids or sections of tissues of the affected organs which comprise T-cells. Illustrative, non-limiting examples of samples useful in the diagnostic method of the invention include different types of biological fluids comprising T-cells, such as blood, lymph and spinal fluids. These biological fluid samples can be obtained by any conventional method known the skilled person. Alternatively, said sample can also be a section of an affected organ tissue sample, for example from a lymph gland, spleen, tonsil, or thymus, which can be obtained by any conventional method, for example by means of biopsy or surgical resection as well as from frozen sections taken for histologic purposes.

According to the first step of the diagnostic method of the invention, variant antigen-binding domain or antibody of the invention is contacted with a sample from the subject under study under suitable conditions known by the person in the art.

The person skilled in the art can use a number of conventional methods to detect TRBC2 in the sample, which are suitable for carrying out the second step of the diagnostic method of the invention. Particularly useful are immunological methods. Thus, the use of the first or the second diagnostic agents of the invention may be particularly useful to perform the diagnostic method according to the invention. The features and particular embodiments of the diagnostic agents of the invention have been previously defined and apply equally to the diagnostic method of the invention.

In the diagnostic method of the invention, a percentage of 70%, or 75%, or 80%, or 85%, or 90%, or 95%, or 96%, or 97%, or 98%, or 99%, or more TRBC2 positive T-cells in the sample may be indicative of the presence of a T-cell lymphoma or leukaemia.

As it will be understood by those skilled in the art, the prediction, although preferred to be, need not be correct for 100% of the subjects to be diagnosed or evaluated. The term, however, requires that a statistically significant portion of subjects can be identified as having an increased probability of having a given outcome. Whether the data obtained from a subject is statistically significant can be determined without further ado by the person skilled in the art using various well-known statistic evaluation tools, e.g., determination of confidence intervals, p-value determination, cross-validated classification rates and the like etc. Details are found in Dowdy and Wearden, Statistics for Research, John Wiley & Sons, New York 1983. Preferred confidence intervals are at least 50%, at least 60%, at least 70%, at least 80%, at least 90% or at least 95%. The p-values are, preferably, 0.01, or 0.005 or lower.

Additionally, the variant antigen-binding domain or antibody of the invention, in view of their ability to specifically bind TRBC2 positive T-cells, can also be used for in vivo diagnosis a T-cell lymphoma or leukaemia. For example, they can be used in medical imaging, i.e. a set of techniques and processes used to create images of a body (or parts and function thereof), e.g., a human body, for clinical purposes, such as medical procedures seeking to reveal, diagnose or examine a disease.

To this end, the variant antigen-binding domain or antibody of the invention are labelled by suitable methods known in the art, and are provided as agents for diagnostic imaging methods, such as radioimmunodiagnostics, positron emission tomography (PET), endoscopy immunofluorescent methods, etc., for example by means of coupling and/or loading with appropriate molecules, for example radioactive isotopes or fluorescent dyes. The variant antigen-binding domain and antibody of the invention may be coupled to gamma-emitting isotopesand used in radioimmunoscintigraphy using gamma cameras or single-photon emission computed tomography. The variant antigen-binding domain and antibody of the invention may be coupled to positron emitters and used in PET. The variant antigen-binding domain and antibody of the invention may be coupled to fluorescent dyes, such as Cy3, Cy2, Cy5 or FITC, and used in endoscopy immunofluorescent methods. The variant antigen-binding domain and antibody of the invention that are modified as described are administered by any suitable route, for example, intravenously, at an appropriate dose for the individual and the location of TRBC2 positive T-cells is detected, determined or measured by processes well known in the art. The methods and technologies used herein, including diagnostic imaging, are known to the skilled artisan, who can also provide suitable dose formulations.

The T-cell lymphoma or leukaemia to be diagnosed may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

The sample may be, or may be derived from, a blood sample.

13. Methods of Personalised Medicine

In another aspect, the present invention provides a method for identifying subjects with a T-cell lymphoma or leukaemia eligible for treatment with a cell, antibody, BiTE, or chemotherapeutic conjugate of the invention, hereinafter "the first method of personalised medicine of the invention", comprising determining the percentage of TRBC2 positive T-cells in a sample comprising T-cells from the subject.

The terms "cell of the invention", "antibody of the invention", "BiTE of the invention", "chemotherapeutic agent of the invention", "subject", and "sample comprising T-cells" have been described in detail in the context of previous aspects of the invention and their features and embodiments apply equally to this aspect of the invention.

In the first method of personalised medicine of the invention, the subject is eligible for said treatment with a cell, antibody, BiTE, or chemotherapeutic conjugate of the invention if the percentage of TRBC2 positive T-cells in the sample is 70%, or 75%, or 80%, or 85%, or 90%, or 95%, or 96%, or 97%, or 98%, or 99%, or more.

In another aspect, the present invention provides a method for selecting a therapy comprising a cell, antibody, BiTE, or chemotherapeutic conjugate of the invention for the treatment of a subject, hereinafter "the second method of personalised medicine of the invention", comprising determining the percentage of TRBC2 positive T-cells in a sample comprising T-cells from the subject.

The terms "cell of the invention", "antibody of the invention", "BiTE of the invention", "chemotherapeutic agent of the invention", "subject", and "sample comprising T-cells" have been described in detail in the context of previous aspects of the invention and their features and embodiments apply equally to this aspect of the invention.

In the second method of personalised medicine of the invention, the therapy comprising a cell, antibody, BiTE, or chemotherapeutic conjugate of the invention is selected to treat said subject if the percentage of TRBC2 positive T-cells in the sample is 70%, or 75%, or 80%, or 85%, or 90%, or 95%, or 96%, or 97%, or 98%, or 99%, or more.

The sample may be, or may be derived from, a blood sample.

The T-cell lymphoma or leukaemia may be selected from peripheral T-cell lymphoma, not otherwise specified (PTCL-NOS); angio-immunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

The invention will now be further described by way of Examples, which are meant to serve to assist one of ordinary skill in the art in carrying out the invention and are not intended in any way to limit the scope of the invention.

EXAMPLES

Example 1: Analysis of the Binding of Anti-TRBC2 Antibodies by Surface Plasmon Resonance (SPR)

Figure 3:
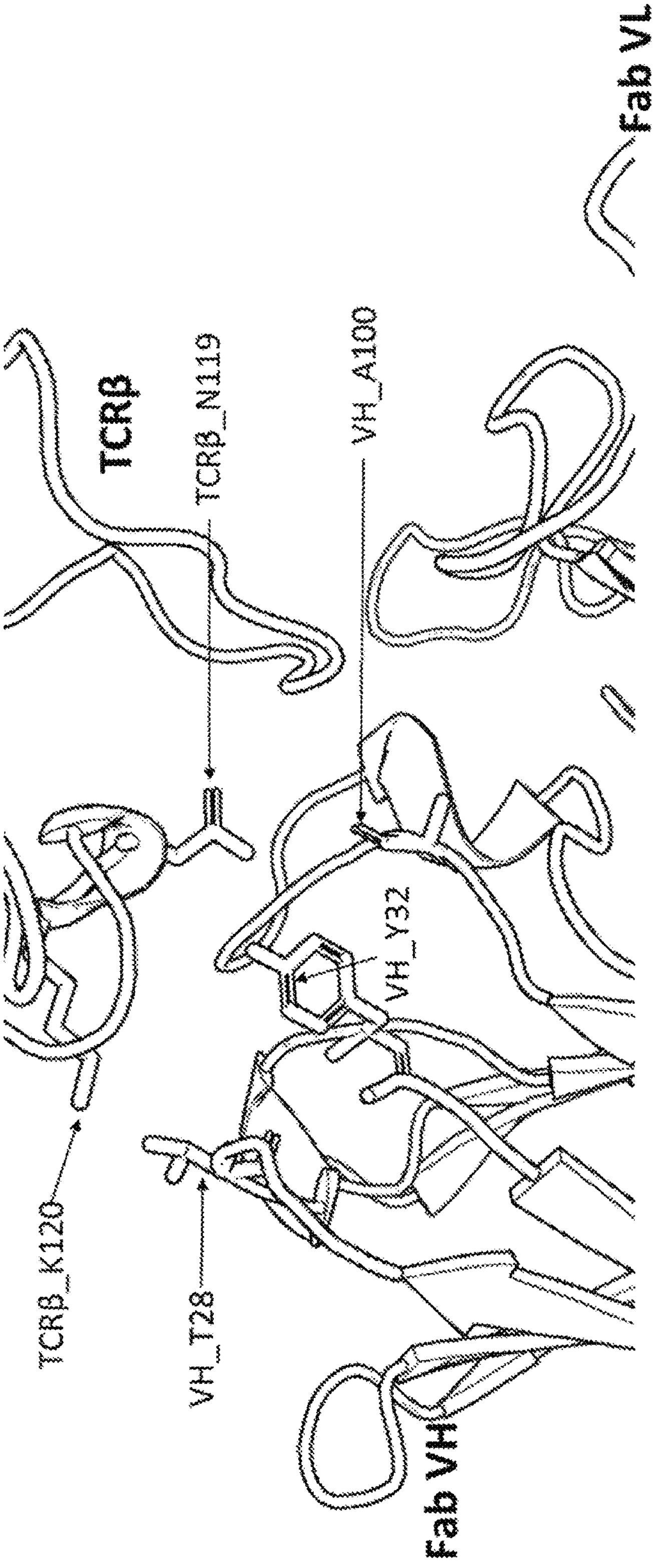
FIG. 3. Structural interface between TCR Beta and Fab fragment of TRBC1 specific antibody Jovi-1.

The crystal structure of the TRBC1 specific monoclonal antibody hJovi-1 was solved in complex with a TRBC1-TCR to 2.4 Å (FIG. 3). Through computational biology and protein engineering, several mutant versions of the anti-TRBC1 binder were rationally designed to switch specificity from TRBC1 to TRBC2. A number of anti-TRBC2 binders were generated in IgG format. Table 1 shows details of the mutations included in the VH and VL domains of hJovi-1.

A series S CM5 sensor chip was immobilised via amine coupling, with an anti-human Fc capture antibody to a density of 9000-10000 RU, using a Biacore T200 instrument. HBS-P+ buffer was used as running buffer in all experimental conditions. The test anti-TRBC2 antibodies (Table 1) were captured on flow cells 2, 3 and 4 to a density of 100-300 RU. Recombinant purified TRBC1 or TRBC2 at known concentrations were used as the ‘analyte’ and injected over the respective flow cells with 150s contact time and 300s dissociation at 30 μl/minute of flow rate. In each experiment, flow cell 1 was unmodified and used for reference subtraction. A ‘0 concentration’ sensorgram of buffer alone was used as a double reference subtraction to factor for drift. Data were fit to a 1:1 Langmuir binding model. Since a capture system was used, a local $R_{max}$ parameter was used for the data fitting in each case.

Results of the affinities for TRBC1 and TRBC2 obtained for each of the anti-TRBC2 antibodies are shown in Table 1. The test anti-TRBC2 antibodies showed a preferential binding to TRBC2, generally in the nM range, with varying ka and kd kinetic properties. Binding to TRBC1 was assessed to be >1 μM in most of the instances, with values approaching the limit of sensitivity for the instrument.

Example 2: Generation of an Anti-TRBC2 CAR Based on the KFN Binder

Figure 4:
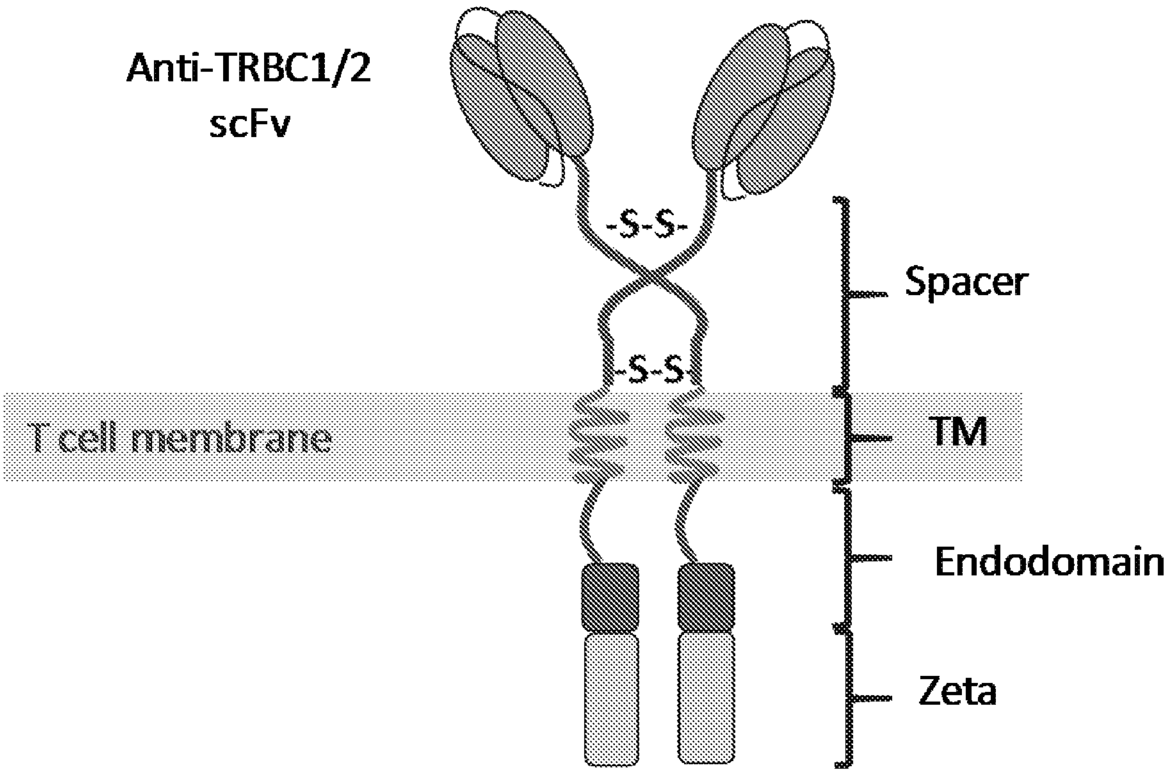
FIG. 4. Diagram of the structure of TRBC1 and TRBC2 specific chimeric antigen receptors (CARs).

Second generation CAR constructs were generated based on an anti-TRBC2 triple mutant (T28K, Y32F, A100N mutations in the VH domain of hJovi-1, SEQ ID NO: 26) and humanised Jovi-1 (hJovi-1) (FIG. 4). These CAR constructs were cloned into a retroviral vector and used to transduce activated PBMCs obtained from healthy donors.

Figure 5:
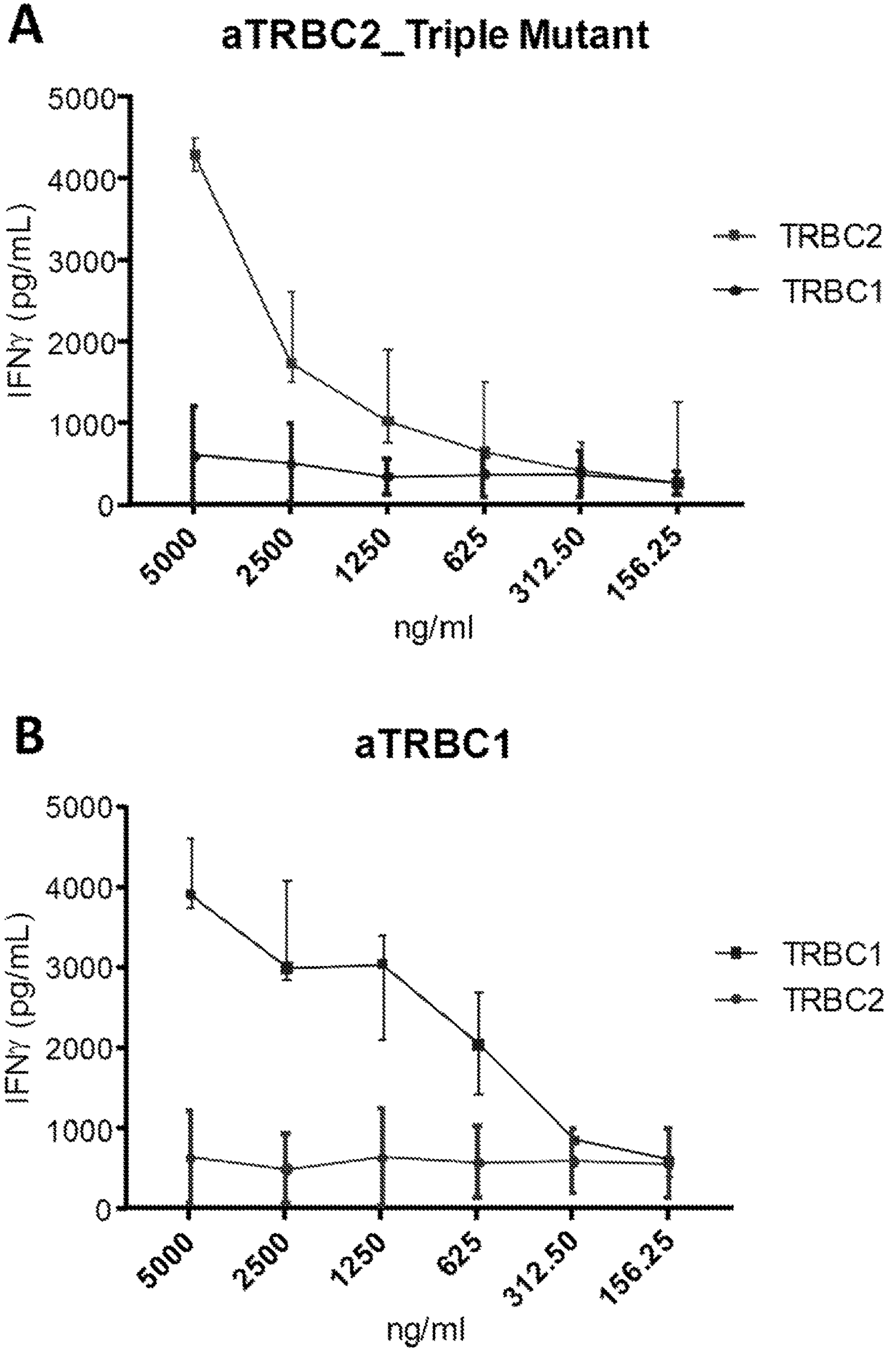
FIG. 5. Functional characterisation of an anti-TRBC2 CAR.

Example 3: Functional Characterisation of an Anti-TRBC2 CAR: Cytokine Production To assess the functional capacity of the anti-TRBC2 triple mutant CAR-T cells towards TRBC2, a plate bound assay was used in which TRBC1 or TRBC2 are immobilised prior to the addition of CAR-T cells. After 72 hours, culture supernatants were collected and IFN-γ production measured by ELISA. In FIG. 5A, anti-TRBC2 triple mutant CAR-T cells showed greater IFN-γ release in the presence of the TRBC2 ligand compared to TRBC1. In contrast, hJovi-1 CAR-T cells showed high IFN-γ production only when cultured with the TRBC1 ligand (FIG. 5B). These results demonstrate that CAR-T cells transduced with the anti-TRBC2 triple mutant have greater activation and cytokine release towards TRBC2 but not when exposed to TRBC1.

Example 4: Functional Characterisation of an Anti-TRBC2 CAR: Cytotoxicity Assay To determine ability of the anti-TRBC2 triple mutant to target TRBC2, cytotoxicity assays were set up using Raji cells transduced to express either TRBC1 or TRBC2 as target cells and co-cultured with CAR-T cells. hJovi-1 CAR-T cells or anti-TRBC2 triple mutant CAR-T cells were cultured in a 1:1 (E:T) ratio with either Raji WT, Raji $TRBC1^{+}$ or Raji $TRBC2^{+}$ cells. Target cell recovery was measured 72 hours post culture by flow cytometry and used to establish cytotoxic capacity of CAR-T cells. Cultures containing anti-TRBC2 triple mutant CAR-T cells showed limited survival of Raji $TRBC2^{+}$ target cells (FIG. 6). In contrast, anti-TRBC2 triple mutant CAR-T cells did not clear Raji $TRBC1^{+}$ target cells indicating their increased proficiency at targeting $TRBC2^{+}$ cells.

We used the engineered monoclonal antibody to generate a 2nd generation anti-TRBC2 CAR. We demonstrated that our anti-TRBC2 CAR showed specificity, cytokine release and cytotoxicity in 72 hr co-cultures against TRBC2+ cell lines but not TRBC1+ cell lines or cell lines that did not express TCR on the surface. Anti-TRBC2 CAR T-cells also demonstrated proliferative capacity in long-term co-culture assays.

Example 5: Functional Characterisation of Anti-TRBC2 CARs: Killing Assay

Additional second generation CAR constructs were generated based on anti-TRBC2 binders from Table 1 having the following mutations:

- T28K, Y32F, A100N mutations in the VH domain and N35K in the VL domain of hJovi-1 (termed N35K, SEQ ID NO: 25),
- T28K, Y32F, A100N, N103L mutations in the VH domain of hJovi-1 (termed N103L, SEQ ID NO: 27),
- T28K, Y32F, A100N, N103M mutations in the VH domain and N35Y in the VL domain of hJovi-1 (termed N103M-N35Y, SEQ ID NO: 28),
- T28K, Y32F, A100N, Y102F, N103M mutations in the VH domain and N35R in the VL domain of hJovi-1 (termed Y102F-N103M-N35R, SEQ ID NO: 29),
- T28K, Y32F, A100N, Y102L, N103M mutations in the VH domain and N35R in the VL domain of hJovi-1 (termed Y102L-N103M-N35R, SEQ ID NO: 30).

These CAR constructs and the anti-TRBC2 triple mutant (T28K, Y32F, A100N mutations in the VH domain of hJovi-1, termed KFN, SEQ ID NO: 26), were cloned into a retroviral vector and used to transduce (a) Jurkat cells, or (b) activated PBMCs obtained from healthy donors. An anti-TRBC1 control CAR, i.e. hJovi-1 CAR, construct was used as control in the killing assay using activated PBMCs.

a) Jurkat Cells

To evaluate whether the binders generated were specific to TRBC2 antigen, Jurkat cells, which are TRBC1+, were transduced with the above anti-TRBC2 CAR constructs. Co-cultures of transduced Jurkat cells were set up at a 1:1 effector to target (E:T) ratio using HPB-ALL cells transduced to express either TRBC1 or TRBC2 only (termed HPB TRBC1 and HPB TRBC2, respectively) as target cells, with HPB-ALL cells having a knocked-out TCR (termed HPB KO) as negative control. Transduced Jurkat cells were plated alone or with αCD3/αCD28 antibodies to be used as negative or positive assay control, respectively. Antigen-specific activation was assessed via staining of CD69 by flow cytometry after 24 h.

Results shown in FIG. 7 revealed that all transduced Jurkat cells were selectively activated after co-incubation with HPB TRBC2 cells. These results demonstrate that all the CARs tested displayed specificity to TRBC2 targets since CD69 upregulation was not observed when Jurkat were co-cultured with TRBC1+ or HPB KO targets.

b) PBMCs

Firstly, PBMCs were separated into TRBC1+ and TRBC2+ cells using magnetic anti-biotin-coated beads after staining with 10 ug/ml biotinylated murine JOVI-1 antibody, which binds to TRBC1 only. The TRBC2+ population was transduced with hJovi-1 CAR (JOVI) and the TRBC1+ population with the above anti-TRBC2 CARs. This differential transduction ensured that antigen activation and target killing were only triggered when the targets were added at controlled cultured conditions (e.g. effector to target ratios and timepoints) rather than in a mixed population where the conditions are different for each PBMC donor.

Secondly, killing assays were setup using HPB-ALL cells transduced to express either TRBC1 or TRBC2 only (termed TRBC1+HPB-ALL and TRBC2+HPB-ALL, respectively) as target cells, with HPB-ALL cells having a knocked-out TCR (termed HPB-KO) as control. Cells were co-cultured at 1:2 E:T ratio 10 days after transduction. Cell killing was assessed by flow cytometry 72 h after assay setup.

Results demonstrated that hJovi-1 CAR-T cells killed TRBC1+HPB-ALL cells only and that all the anti-TRBC2 CAR-T cells killed TRBC2+HPB-ALL cells only (FIG. 8). Similar levels of background killing was observed for all TRBC1- and TRBC2-specific CAR-T cells on HPB-KO control cells, indicating that all the CARs tested were specific to their cognate antigen.

Example 6: Analysis of the Effect of Different Antibody Formats in the Binding of Anti-TRBC2 Antibodies by Surface Plasmon Resonance (SPR)

The effect of multimerisation in the anti-TRBC2 binders was analysed by SPR. To this end, anti-TRBC2 having T28K, Y32F, A100N, Y102L and N103M mutations in the VH domain, and N35R mutation in the VL domain of hJovi-1 antibody was used in three different formats, i.e. scFv (SEQ ID NO: 22), scFv-Fc (SEQ ID NO: 23) and scFv-COMP (SEQ ID NO: 24) antibody formats.

SEQ ID NO: 22

```
QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GLMFDGAYRFFDFWGQGTMVTVSSGGGGSGGGGSGGGGSDIVMTQSPLSL

PVTPGEPASISCRSSQRLVHSNGRTYLHWYLQKPGQSPRLLIYRVSNRFP

GVPDRFSGSGSGTDFTLKISRVEAEDVGVYYCSQSTHVPYTFGQGTKLEI

KR
```

-continued

SEQ ID NO: 23

```
QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GLMFDGAYRFFDFWGQGTMVTVSSGGGGSGGGGSGGGGSDIVMTQSPLSL

PVTPGEPASISCRSSQRLVHSNGRTYLHWYLQKPGQSPRLLIYRVSNRFP

GVPDRFSGSGSGTDFTLKISRVEAEDVGVYYCSQSTHVPYTFGQGTKLEI

KRSDPRGPTIKPCPPCKCPAPNLLGGPSVFIFPPKIKDVLMISLSPIVTC

VVVDVSEDDPDVQISWFVNNVEVHTAQTQTHREDYNSTLRVVSALPIQHQ

DWMSGKEFKCKVNNKDLPAPIERTISKPKGSVRAPQVYVLPPPEEEMTKK

QVTLTCMVTDFMPEDIYVEWTNNGKTELNYKNTEPVLDSDGSYFMYSKLR

VEKKNWVERNSYSCSVVHEGLHNHHTTKSFSRTPGK
```

SEQ ID NO: 24

```
QVQLVQSGAEVKKPGASVKVSCKASGYKFTGFVMHWVRQAPGQGLEWMGF

INPYNDDIQSNERFRGRVTMTRDTSISTAYMELSRLRSDDTAVYYCARGN

GLMFDGAYRFFDFWGQGTMVTVSSGGGGSGGGGSGGGGSDIVMTQSPLSL

PVTPGEPASISCRSSQRLVHSNGRTYLHWYLQKPGQSPRLLIYRVSNRFP

GVPDRFSGSGSGTDFTLKISRVEAEDVGVYYCSQSTHVPYTFGQGTKLEI

KRSGGGGSGGGGSGGGGSAGSDLGPQMLRELQETNAALQDVRELLRQQVR

EITFLKNTVMECDACGSGKKDPKSGGGGSYPYDVPDYA
```

To test 1:1 binding interaction of the anti-TRBC2 scFv, a series S CM5 sensor chip was immobilised via amine coupling, with an anti-human Fc capture antibody to a density of 9000-10000 RU, using a Biacore T200 instrument. HBS-P+ buffer was used as running buffer in all experimental conditions. The test anti-TRBC2 antibody was captured on flow 4 to a density of 200-250 RU. Recombinant purified TRBC1 or TRBC2 at known concentrations were used as the 'analyte' and injected over the respective flow cells with 150s contact time and 300s dissociation at 30 μl/minute of flow rate. Flow cell 1 was unmodified and used for reference subtraction. A '0 concentration' sensorgram of buffer alone was used as a double reference subtraction to factor for drift. Data were fit to a 1:1 Langmuir binding model. Since a capture system was used, a local $R_{max}$ parameter was used for the data fitting in each case. Off-rate value was determined, and half-life calculated according to: t½=ln 2/kd.

Results shown in FIG. 9A revealed that this anti-TRBC2 scFv binder has a half-life of 8 s. Binding affinity of this binder is shown in Table 1.

To test multivalent interaction of scFv-Fc and scFv-COMP antibody formats, a series S CAP chip was immobilised with Biotin capture reagent to 2500-5000 RU. Soluble recombinant biotinylated TRBC1 and TRBC2 were captured on flow cells 3, in independent experimental cycles, to a density of 90-110 RU. Purified anti-TRBC2 scFv-Fc or scFv-COMP antibodies were injected over the flow cell with 150s contact time and 300s dissociation at 30 μl/minute of flow rate. On flow cell 1, biotinylated protein was omitted and used for reference subtraction. A '0 concentration' sensorgram of buffer alone was used as a double reference subtraction to factor for drift. Data were fit to a 1:1 Langmuir binding model. Since a capture system was used, a local Rmax parameter was used for the data fitting in each case. Off-rate value was determined, and half-life calculated according to: t½=ln 2/kd.

Results shown in FIGS. 9B and 9C revealed that the half-lives of the scFv-Fc and scFv-COMP antibody formats are 16.2 s and 7.3 min, respectively.

Therefore, these results demonstrate that multimerisation improves binding of low affinity/high specificity TRBC2 antibodies.

This application claims the benefit of United Kingdom application No. 1817822.8 filed on 31 Oct. 2018. This application is incorporated herein by reference in its entirety.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A variant antigen-binding domain which comprises mutations in the VH domain compared to a reference antibody having a VH domain with the sequence shown in SEQ ID NO: 1 and a VL domain with the sequence shown in SEQ ID NO: 2, wherein the variant antigen-binding domain comprises the following mutation combinations:

T28K, Y32F, A100N, Y102F in the VH domain;

T28K, Y32F, A100N, Y102L, N103M in the VH domain and N35R in the VL domain;

T28K, Y32F, A100N, Y102L, N103W in the VH domain and N35K in the VL domain;

T28K, Y32F, A100N, Y102L, N103W in the VH domain and N35R in the VL domain;

T28K, Y32F, A100N, N103E in the VH domain;

V2K, T28K, Y32F, A100N in the VH domain;

N103E, T28K, T32F, A100N in the VH domain and N35M in the VL domain;

T28K, Y32F, A100N, N103F in the VH domain and N35K in the VL domain;

T28K, Y32F, A100N, A107S in the VH domain;

G31S, T28K, Y32F, A100N in the VH domain;

V2R, T28K, Y32F, A100N in the VH domain;

T28K, Y32F, A100N, N103M in the VH domain and N35R in the VL domain;

N103W, T28K, Y32F, A100N in the VH domain and N35F in the VL domain;

T28K, G31R, Y32F, A100N in the VH domain;

N103F, T28K, T32F, A100N in the VH domain and N35F in the VL domain;
N103F, T28K, T32F, A100N in the VH domain and N35M in the VL domain;
N103M, T28K, T32F, A100N in the VH domain and N32F in the VL domain;
T28K, Y32F, A100N, N103S in the VH domain;
T28K, Y32F, A100N, N103Q in the VH domain;
Y27F, T28K, Y32F, A100N in the VH domain;
N103F, T28K, Y32F, A100N in the VH domain and N35Y in the VL domain;
N103W, T28K, Y32F, A100N in the VH domain and N35M in the VL domain;
N103L, T28K, Y32F, A100N in the VH domain and N35F in the VL domain;
N103L, T28K, Y32F, A100N in the VH domain and N35K in the VL domain;
T28K, Y32F, A100N, N103W in the VH domain;
T28K, Y32F, A100N, N103F in the VH domain;
N103L, T28K, Y32F, A100N in the VH domain and N35Y in the VL domain;
N103W, T28K, Y32F, A100N in the VH domain and N35K in the VL domain;
N103L, T28K, Y32F, A100N in the VH domain and N35R in the VL domain;
N103L, T28K, Y32F, A100N in the VH domain and N35M in the VL domain;
N103S, T28K, Y32F, A100N in the VH domain and N35Y in the VL domain;
N103S, T28K, Y32F, A100N in the VH domain and N35F in the VL domain;
T28K, Y32F, A100N, N103L in the VH domain;
T28K, Y32F, A100N, N103M in the VH domain and N35Y in the VL domain;
N103S, T28K, Y32F, A100N in the VH domain and N35R in the VL domain;
T28K, Y32F, R98K, A100N in the VH domain;
N103S, T28K, Y32F, A100N in the VH domain and N35K in the VL domain;
T28K, Y32F, A100N in the VH domain and N35F in the VL domain;
N103W, T28K, T32F, A100N in the VH domain and N35R in the VL domain;
T28K, Y32F, A100N, N103M in the VH domain;
N103S, T28K, Y32F, A100N in the VH domain and N35M in the VL domain;
T28K, Y32F, A100N in the VH domain and N35R in the VL domain;
T28K, Y32F, A100N, N103Y in the VH domain;
T28K, Y32F, A100N, N103A in the VH domain;
T28K, Y32F, A100N, N103H in the VH domain;
T28K, Y32F, A100N, N103M in the VH domain and N35M in the VL domain;
T28K, Y32F, A100N in the VH domain and N35K in the VL domain;
T28K, Y32F, A100N in the VH domain and R55K in the VL domain;
T28K, Y32F, A100N in the VH domain;
Y27W, T28K, Y32F, A100N in the VH domain;
T28K, Y32F, A100N, Y102F in the VH domain and N35R in the VL domain;
T28K, Y32F, A100N, Y102F, N103M in the VH domain and N35R in the VL domain;
T28K, Y32F, A100N, Y102F, N103M in the VH domain and N35F in the VL domain;
Y27M, T28K, Y32F, A100N in the VH domain;
T28K, G31K, Y32F, A100N in the VH domain;

T28K, Y32F, A100N, Y102F, N103M in the VH domain and N35K in the VL domain; or
Y27N, T28K, V32F, A100N in the VH domain;

and wherein the variant antigen-binding domain displays an increased affinity for TRBC2 over the reference antibody.

2. An antibody comprising a variant antigen-binding domain according to claim 1.

3. A chimeric antigen receptor (CAR) comprising a variant antigen-binding domain according to claim 1, a spacer, a transmembrane domain and an endodomain.

4. A bispecific T-cell engager comprising a variant antigen-binding domain according to claim 1 and a T-cell activation domain.

5. A nucleic acid sequence encoding:

a variant antigen-binding domain, an antibody comprising a variant antigen-binding domain, a CAR comprising a variant antigen-binding domain, or a bispecific T-cell engager comprising a variant antigen-binding domain, wherein the variant binding domain comprises mutations in the VH domain compared to a reference antibody having a VH domain with the sequence shown in SEQ ID NO: 1 and a VL domain with the sequence shown in SEQ ID NO: 2, wherein the mutations comprise the mutation combinations:

T28K, Y32F, A100N, Y102F in the VH domain;
T28K, Y32F, A100N, Y102L, N103M in the VH domain and N35R in the VL domain;
T28K, Y32F, A100N, Y102L, N103W in the VH domain and N35K in the VL domain;
T28K, Y32F, A100N, Y102L, N103W in the VH domain and N35R in the VL domain;
T28K, Y32F, A100N, N103E in the VH domain;
V2K, T28K, Y32F, A100N in the VH domain;
N103E, T28K, T32F, A100N in the VH domain and N35M in the VL domain;
T28K, Y32F, A100N, N103F in the VH domain and N35K in the VL domain;
T28K, Y32F, A100N, A107S in the VH domain;
G31S, T28K, Y32F, A100N in the VH domain;
V2R, T28K, Y32F, A100N in the VH domain;
T28K, Y32F, A100N, N103M in the VH domain and N35R in the VL domain;
N103W, T28K, Y32F, A100N in the VH domain and N35F in the VL domain;
T28K, G31R, Y32F, A100N in the VH domain;
N103F, T28K, T32F, A100N in the VH domain and N35F in the VL domain;
N103F, T28K, T32F, A100N in the VH domain and N35M in the VL domain;
N103M, T28K, T32F, A100N in the VH domain and N32F in the VL domain;
T28K, Y32F, A100N, N103S in the VH domain;
T28K, Y32F, A100N, N103Q in the VH domain;
Y27F, T28K, Y32F, A100N in the VH domain;
N103F, T28K, Y32F, A100N in the VH domain and N35Y in the VL domain;
N103W, T28K, Y32F, A100N in the VH domain and N35M in the VL domain;
N103L, T28K, Y32F, A100N in the VH domain and N35F in the VL domain;
N103L, T28K, Y32F, A100N in the VH domain and N35K in the VL domain;
T28K, Y32F, A100N, N103W in the VH domain;
T28K, Y32F, A100N, N103F in the VH domain;
N103L, T28K, Y32F, A100N in the VH domain and N35Y in the VL domain;

N103W, T28K, Y32F, A100N in the VH domain and N35K in the VL domain;
N103L, T28K, Y32F, A100N in the VH domain and N35R in the VL domain;
N103L, T28K, Y32F, A100N in the VH domain and N35M in the VL domain;
N103S, T28K, Y32F, A100N in the VH domain and N35Y in the VL domain;
N103S, T28K, Y32F, A100N in the VH domain and N35F in the VL domain;
T28K, Y32F, A100N, N103L in the VH domain;
T28K, Y32F, A100N, N103M in the VH domain and N35Y in the VL domain;
N103S, T28K, Y32F, A100N in the VH domain and N35R in the VL domain;
T28K, Y32F, R98K, A100N in the VH domain;
N103S, T28K, Y32F, A100N in the VH domain and N35K in the VL domain;
T28K, Y32F, A100N in the VH domain and N35F in the VL domain;
N103W, T28K, T32F, A100N in the VH domain and N35R in the VL domain;
T28K, Y32F, A100N, N103M in the VH domain;
N103S, T28K, Y32F, A100N in the VH domain and N35M in the VL domain;
T28K, Y32F, A100N in the VH domain and N35R in the VL domain;
T28K, Y32F, A100N, N103Y in the VH domain;
T28K, Y32F, A100N, N103A in the VH domain;
T28K, Y32F, A100N, N103H in the VH domain;
T28K, Y32F, A100N, N103M in the VH domain and N35M in the VL domain;
T28K, Y32F, A100N in the VH domain and N35K in the VL domain;
T28K, Y32F, A100N in the VH domain and R55K in the VL domain;
T28K, Y32F, A100N in the VH domain;
Y27W, T28K, Y32F, A100N in the VH domain;
T28K, Y32F, A100N, Y102F in the VH domain and N35R in the VL domain;
T28K, Y32F, A100N, Y102F, N103M in the VH domain and N35R in the VL domain;
T28K, Y32F, A100N, Y102F, N103M in the VH domain and N35F in the VL domain;
Y27M, T28K, Y32F, A100N in the VH domain;
T28K, G31K, Y32F, A100N in the VH domain;
T28K, Y32F, A100N, Y102F, N103M in the VH domain and N35K in the VL domain; or
Y27N, T28K, V32F, A100N in the VH domain; and
wherein the variant antigen-binding domain displays an increased affinity for TRBC2 over the reference antibody.

6. A vector comprising a nucleic acid sequence according to claim 5.

7. A cell which comprises a CAR according to claim 3.

8. A method for making a cell, which comprises the step of transducing or transfecting a cell with a vector according to claim 6.

9. A conjugate comprising an antibody comprising a variant antigen-binding domain according to claim 1, and a detectable entity or a chemotherapeutic entity.

10. The conjugate according to claim 9, which comprises a chemotherapeutic entity.

11. A method for treating a T-cell lymphoma or leukaemia in a subject which comprises the step of administering:
a cell according to claim 7, or
an antibody comprising a variant antigen-binding domain according to claim 1, a bispecific T-cell engager comprising a variant antigen-binding domain according to claim 1 or a conjugate comprising a variant antigen-binding domain according to claim 1 to a subject,
wherein the malignant T-cells express TRBC2.

12. A method for diagnosing a T-cell lymphoma or leukaemia in a subject which comprises the step of contacting a variant antigen-binding domain according to claim 1, or an antibody comprising the variant antigen-binding domain, to a sample comprising T-cells from the subject and determining the percentage of TRBC2 positive T-cells in the sample, wherein T-cell lymphoma or leukaemia is diagnosed when the percentage is 70%, or 75%, or 80%, or 85%, or 90%, or 95%, or 96%, or 97%, or 98%, or 99%, or more.

13. A method for identifying subjects with a T-cell lymphoma or leukaemia eligible for treatment with a cell comprising a CAR comprising an antigen-binding domain according to claim 1, or an antibody comprising a variant antigen-binding domain according to claim 1, a bispecific T-cell engager comprising a variant antigen-binding domain according to claim 1, or a conjugate comprising a variant antigen-binding domain according to claim 1, comprising determining the percentage of TRBC2 positive T-cells in a sample comprising T-cells from the subject, wherein patients with a T-cell lymphoma or leukaemia are identified when the percentage is 70%, or 75%, or 80%, or 85%, or 90%, or 95%, or 96%, or 97%, or 98%, or 99%, or more.

14. A method for selecting a therapy comprising a cell comprising a CAR comprising an antigen-binding domain according to claim 1, or an antibody comprising a variant antigen-binding domain according to claim 1, a bispecific T-cell engager comprising a variant antigen-binding domain according to claim 1, or a conjugate comprising a variant antigen-binding domain according to claim 1, for the treatment of a subject, comprising determining the percentage of TRBC2 positive T-cells in a sample comprising T-cells from the subject.

15. The method according to claim 11, wherein the T-cell lymphoma or leukaemia is selected from peripheral T-cell lymphoma, not otherwise specified (PTCL-NOS); angioimmunoblastic T-cell lymphoma (AITL), anaplastic large cell lymphoma (ALCL), enteropathy-associated T-cell lymphoma (EATL), hepatosplenic T-cell lymphoma (HSTL), extranodal NK/T-cell lymphoma nasal type, cutaneous T-cell lymphoma, primary cutaneous ALCL, T cell prolymphocytic leukaemia and T-cell acute lymphoblastic leukaemia.

* * * * *